US012029791B2

(12) United States Patent
Dhawan et al.

(10) Patent No.: US 12,029,791 B2
(45) Date of Patent: *Jul. 9, 2024

(54) THERAPEUTIC CONJUGATES

(71) Applicant: Totus Medicines Inc., Cambridge, MA (US)

(72) Inventors: Neil Sonin Dhawan, Somerville, MA (US); James Abellera Blair, Arlington, MA (US); Robert B. Perni, Marlborough, MA (US)

(73) Assignee: Totus Medicines Inc., Cambridge, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/955,182

(22) Filed: Sep. 28, 2022

(65) Prior Publication Data

US 2023/0096658 A1  Mar. 30, 2023

Related U.S. Application Data

(60) Division of application No. 17/694,592, filed on Mar. 14, 2022, now Pat. No. 11,484,597, which is a continuation of application No. PCT/US2020/051491, filed on Sep. 18, 2020.

(60) Provisional application No. 63/078,055, filed on Sep. 14, 2020, provisional application No. 62/902,554, filed on Sep. 19, 2019.

(51) Int. Cl.
*A61K 47/55* (2017.01)
*A61K 31/5377* (2006.01)
*A61K 47/54* (2017.01)
*A61P 35/00* (2006.01)

(52) U.S. Cl.
CPC .......... *A61K 47/55* (2017.08); *A61K 31/5377* (2013.01); *A61K 47/542* (2017.08); *A61K 47/545* (2017.08); *A61P 35/00* (2018.01)

(58) Field of Classification Search
CPC ..................................................... A61K 47/55
See application file for complete search history.

(56) References Cited

U.S. PATENT DOCUMENTS

| | | |
|---|---|---|
| 5,585,245 A | 12/1996 | Johnsson et al. |
| 7,244,733 B2 | 7/2007 | Hunt et al. |
| 9,073,927 B2 | 7/2015 | Pastor et al. |
| 9,440,981 B2 | 9/2016 | Wu et al. |
| 9,447,101 B2 | 9/2016 | Yang et al. |
| 9,724,352 B2 | 8/2017 | Yang et al. |
| 11,484,597 B2 | 11/2022 | Dhawan et al. |
| 2011/0230476 A1 | 9/2011 | Niu et al. |
| 2012/0231963 A1 | 9/2012 | Huang et al. |
| 2013/0053371 A1 | 2/2013 | Pastor Fernandez et al. |
| 2014/0079690 A1 | 3/2014 | Buggy et al. |
| 2014/0323464 A1 | 10/2014 | Taunton, Jr. et al. |
| 2015/0141644 A1 | 5/2015 | Yang et al. |
| 2015/0361100 A1 | 12/2015 | Biagetti et al. |
| 2016/0115166 A1 | 4/2016 | Wu et al. |
| 2017/0000800 A1 | 1/2017 | Yang et al. |
| 2017/0296659 A1 | 10/2017 | Lebwohl et al. |
| 2022/0211855 A1 | 7/2022 | Dhawan et al. |
| 2022/0387603 A1 | 12/2022 | Dhawan et al. |

FOREIGN PATENT DOCUMENTS

| | | |
|---|---|---|
| CA | 3068114 A1 | 12/2018 |
| CN | 109081905 A | 12/2018 |
| EP | 2524918 A1 | 11/2012 |
| EP | 2857403 A1 | 4/2015 |
| WO | WO-9844350 A1 | 10/1998 |
| WO | WO-2005097052 A1 | 10/2005 |
| WO | WO-2007035428 A1 | 3/2007 |
| WO | WO-2009023179 A2 | 2/2009 |
| WO | WO-2010091409 A1 | 8/2010 |
| WO | WO-2011031896 A2 | 3/2011 |
| WO | WO-2011141713 A1 | 11/2011 |
| WO | WO-2011150356 A1 | 12/2011 |
| WO | WO-2013177983 A1 | 12/2013 |
| WO | WO-2013178021 A1 | 12/2013 |
| WO | WO-2017004134 A1 | 1/2017 |
| WO | WO-2019027765 A1 | 2/2019 |
| WO | WO-2019113523 A1 | 6/2019 |
| WO | WO-2020052772 A1 | 3/2020 |
| WO | WO-2020243457 A1 | 12/2020 |
| WO | WO-2021055747 A1 | 3/2021 |
| WO | WO-2021243421 A1 | 12/2021 |
| WO | WO-2022031952 A2 | 2/2022 |
| WO | WO-2022198024 A1 | 9/2022 |
| WO | WO-2023179771 A1 | 9/2023 |
| WO | WO-2023183936 A2 | 9/2023 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Mishra, Int. J. Mol. Sci. 2021, 22, 3464.*
Co-pending U.S. Appl. No. 18/550,878, inventors Dhawan et al., filed on Sep. 15, 2023.
Agard, et al., "A Strain-Promoted [3+2] Azide-Alkyne Cycloaddition for Covalent Modification of Biomolecules in Living Systems". J. Am. Chem. Soc., vol. 126:15046-15047 (Nov. 2, 2004).

(Continued)

*Primary Examiner* — Nizal S Chandrakumar
(74) *Attorney, Agent, or Firm* — COOLEY LLP

(57) ABSTRACT

This disclosure generally relates to therapeutic conjugates that covalently bind to a biological target. Methods of administering the compositions to a subject in need thereof are also provided herein.

8 Claims, No Drawings

(56) References Cited

OTHER PUBLICATIONS

Bliss, C.I., "The toxicity of poisons applied jointly," Annals of Applied Biology, Aug. 1939, 26(3), pp. 585-615.
Cantley et al., "Oncogenes and signal transduction," Cell 64(2), Jan. 1991, pp. 281-302.
Escobedo, J.A. and Williams, L.T., "A PDGF receptor domain essential for mitogenesis but not for many other responses to PDGF," Nature, vol. 335, Sep. 1, 1988, pp. 85-87.
Extended European Search Report for European Application No. EP20865745.2 dated Sep. 29, 2023, 8 pages.
Fantl et al., "Distinct phosphotyrosines on a growth factor receptor bind to specific molecules that mediate different signaling pathways," Cell, May 1992, 69(3), pp. 413-423.
International Preliminary Report on Patentability for International Application No. PCT/US2022/020912 dated Sep. 28, 2023, 11 pages.
International Search Report and Written Opinion for International Application No. PCT/US2023/064954, mailed on Aug. 25, 2023, 13 pages.
Invitation to Pay Additional Fees for International Application No. PCT/US2023/064954 dated Jun. 12, 2023, 3 pages.
Katso et al., "Cellular function of phosphoinositide 3-Kinases: Implications for development, Immunity, Homeostasis, and Cancer," Annual Review of Cell and Development Biology, Nov. 2001, 17(1), pp. 615-675.
Kwan et al., "The path to the clinic: a comprehensive review on direct KRASG12C inhibitors," Journal of Experimental & Clinical Cancer Research, Dec. 2022, 41(1), pp. 1-23.
Loewe, S., "The problem of synergism and antagonism of combined drugs," Arzneimittel-Forschung, Jun. 1953, 3(6), pp. 285-290.
Vanhaesebroeck et al., "Synthesis and Function of 3-Phosphorylated Inositol Lipids," Annual Review of Biochemistry, Jul. 2001, 70(1), pp. 535-602.
Anderson, et al., "Practical Process Research & Development, Chapter 11, Tools for Purifying the Product: col. Chromatography, Crystallization and Reslurrying," Academic Press, San Diego, 2000, pp. 223-224, XP002565895.
Byrn et al., "Pharmaceutical Solids: A strategic Approach to Regulatory Considerations," Pharmaceutical Research, vol. 12, No. 7, Jul. 1995 (Jul. 1995), pp. 945-954, XP000996386, ISSN: 0724-8741, DOI: 10.1023/A:1016241927429.
Caira, M.R., "Crystalline Polymorphism of Organic Compounds," Topics in Current Chemistry 1998, vol. 198, pp. 163-208, XP001156954.
Harwood, et al., "Experimental organic chemistry—Principles and practice," Blackwell Science, Oxford, 1989, pp. 127-132, XP003025361.
International Search Report and Written Opinion for International Application No. PCT/CN2023/083760 dated Jun. 26, 2023, 18 pages.
Blair et al., "Structure-guided development of affinity probes for tyrosine kinases using chemical genetics," Nature Chemical Biology, Apr. 2007, 3:229-238.
Brognard, J. et al., "Protein Kinase Signalling Networks in Cancer," Curr. Opin. Genet. Dev., Feb. 2011, 21(1):4-11.
Cohen, P., "The origins of protein phosphorylation," Nature Cell Biology, vol. 4, May 2002, E127-E130.
Darabedian et al., "Optimization of Chemoenzymatic Mass Tagging by Strain-Promoted Cycloaddition (SPAAC) for the Determination of O-GlcNac Stoichiometry by Western Blotting," Biochemistry, Aug. 2018, 57, pp. 5769-5774.
International Preliminary Report on Patentability for Application No. PCT/US2020/051491, mailed Mar. 15, 2022, 6 pages.
International Search Report and Written Opinion for Application No. PCT/US2020/051491, mailed Dec. 14, 2020, 9 pages.
International Search Report and Written Opinion for International Application No. PCT/US2022/020912 dated Jul. 13, 2022, 21 pages.
Invitation to Pay Fees for Application No. PCT/US2022/020912, mailed May 9, 2022, 3 pages.
Lanman et al., "Discovery of a Covalent Inhibitor of KRASG12C (AMG 510) for the Treatment of Solid Tumors," Journal of Medicinal Chemistry, 2020, 63:52-65.
Liu et al., "Decrease in phosphorylated ERK indicates the therapeutic efficacy of a clinical PI3Kα-selective inhibitor CYH33 in breast cancer," Cancer Letters, Oct. 2018, 433:273-282.
Mucaki et al., "Predicting responses to platin chemotherapy agents with biochemically-inspired machine learning," Signal Transduction and Targeted Therapy, Jan. 2019, 4(1), 1-12.
Niessen et al., "Proteome-wide Map of Targets of T790M-EGFR-Directed Covalent Inhibitors," Cell Chemical Biology, Nov. 2017, 24:1388-1400, e7.
Pubchem, Substance Record for SID 446703929, Available Date: Nov. 10, 2021 [retrieved on Jun. 21, 2022]. Retrieved from the Internet: URL: <url: <a=href=>https://pubchem.ncbi.nlm.nih.gov/substance/446703929.</url:>, 5 pages.
Shi et al., "PI3Kα inhibitors sensitive esophageal squamous cell carcinoma to radiation by abrogating survival signals in tumor cells and tumor microenvironment," Cancer Letters, Sep. 2019, 459:145-155.
Zhang et al., "Covalent targeting or remote cysteine residues to develop CDK12 and 13 inhibitors," Nat. Chem Biol. Oct. 2016, 12(10):876-884.
Maurais et al., "Reactive-Cysteine Profiling for Drug Discovery," Current Opinion in Chemical Biology, Jun. 2019, vol. 50, pp. 29-36.
Nacht M., et al., "Discovery of a Potent and Isoform-Selective Targeted Covalent Inhibitor of the Lipid Kinase PI3Kα," Journal of Medicinal Chemistry, Jan. 29, 2013, vol. 56, No. 3, pp. 712-721.

* cited by examiner

THERAPEUTIC CONJUGATES

CROSS REFERENCE TO RELATED APPLICATIONS

This application is a Divisional of U.S. application Ser. No. 17/694,592, filed Mar. 14, 2022, which is a Continuation of International Application No. PCT/US2020/051491, filed Sep. 18, 2020, which claims priority to U.S. Provisional Patent Application No. 62/902,554 filed Sep. 19, 2019, entitled THERAPEUTIC CONJUGATES and U.S. Provisional Patent Application No. 63/078,055 filed Sep. 14, 2020, entitled THERAPEUTIC CONJUGATES, the contents of each of which are herein incorporated by reference in their entireties.

FIELD OF THE DISCLOSURE

This disclosure generally relates to therapeutic conjugates that covalently bind to a biological target.

BACKGROUND

Covalent inhibitors bind to a receptor in the same way as a classic inhibitor, but instead of disassociating, covalent inhibitors form a covalent, permanent, chemical bond to the receptor. Some examples of covalent inhibitors include penicillin, aspirin, clopidogrel, EGFR kinase inhibitor Afatinib used to treat lung cancer, and Bruton Tyrosine kinase inhibitor Ibrutinib used to treat B-cell malignancies. Furthermore, in the field of oncology, covalent inhibitors are effective against drug-resistant tumors, and in general display more potency at inhibiting tumor growth.

Recently, covalent inhibitors have attracted the attention of major pharmaceutical companies because the use of covalent inhibitors offers an increased potency and extended duration of action when compared to classic reversible inhibitors. Prolonged duration of action translates into lower dosage frequency, i.e., patients have to take fewer pills and take it less frequently.

There is a need to design therapeutic conjugates that can bind to a biological target covalently and to develop high throughput screening methods for the therapeutic conjugates.

SUMMARY

In some embodiments, the present disclosure provides a therapeutic conjugate which may form a covalent bond with a kinase or pseudokinase. The kinase may be PI3-kinase (PI3K). The therapeutic conjugate may have a structure of (FCB)a-(L)b-(CLM)c, wherein a and c are, independently, integers between 1 and 5, b is an integer between 0 and 5, and wherein the FCB moiety comprises a PI3K inhibitor, or a fragment, analog or derivative thereof. In some embodiments, the FCB may comprise

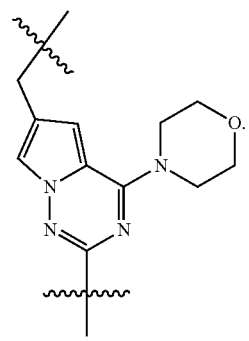 [SMILES: *Cc1cc2c(N3CCOCC3)nc(*)nn2c1]

The therapeutic conjugate may comprise a structure selected from the group consisting of Compound 1-101 to Compound 1-172.

In some embodiments, the therapeutic conjugate may have a structure of

Formula 1-50

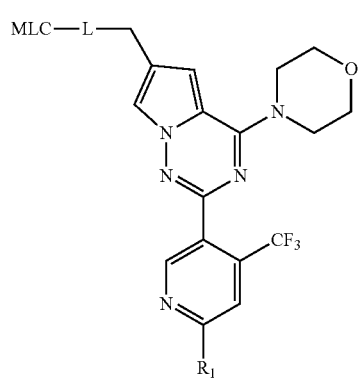

or a pharmaceutically acceptable salt thereof, wherein L is selected from the group consisting of

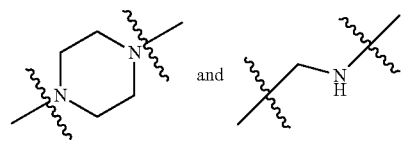

wherein either end can be connected to CLM; R1 is selected from the group consisting of

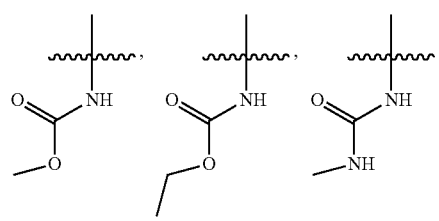

and
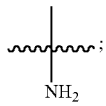
and CLM is selected from the group consisting of
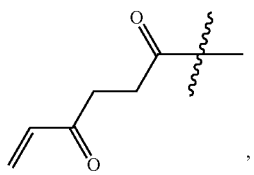,
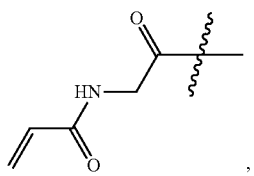,
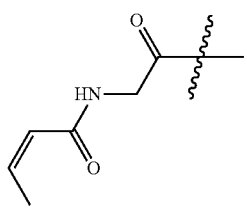,
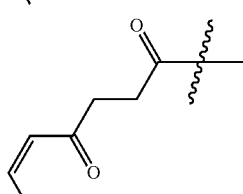,
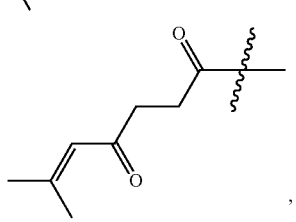,
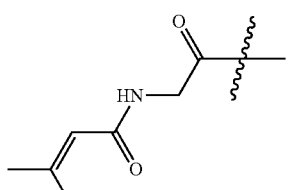,
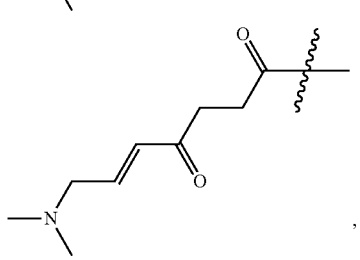,
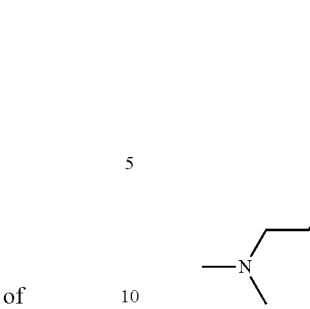,
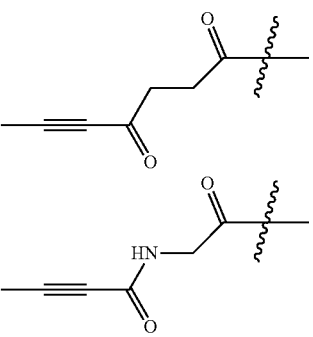,
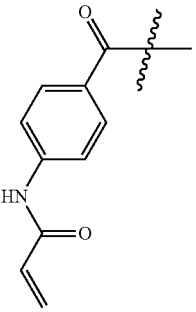
and
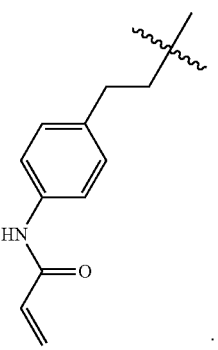.
The therapeutic conjugate may be selected from the group consisting of compounds 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-137, 1-138, 1-145, 1-146, 1-153, 1-154, 1-161, 1-162, 1-169, 1-170, 1-171 and 1-172.

In some embodiments, the therapeutic conjugate may have a structure of

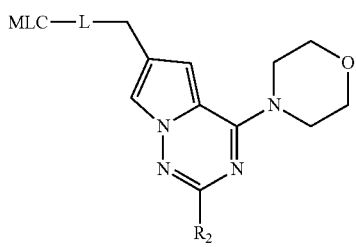
Formula 1-51 or a pharmaceutically acceptable salt thereof, wherein L is

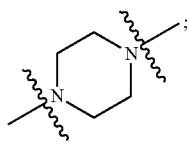

R2 is selected from the group consisting of

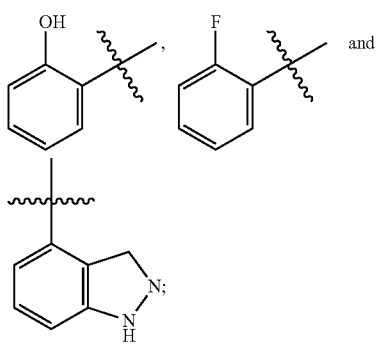

and CLM is selected from the group consisting of

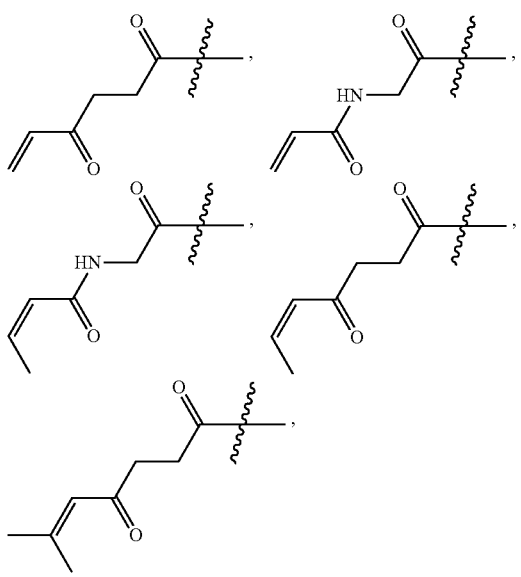

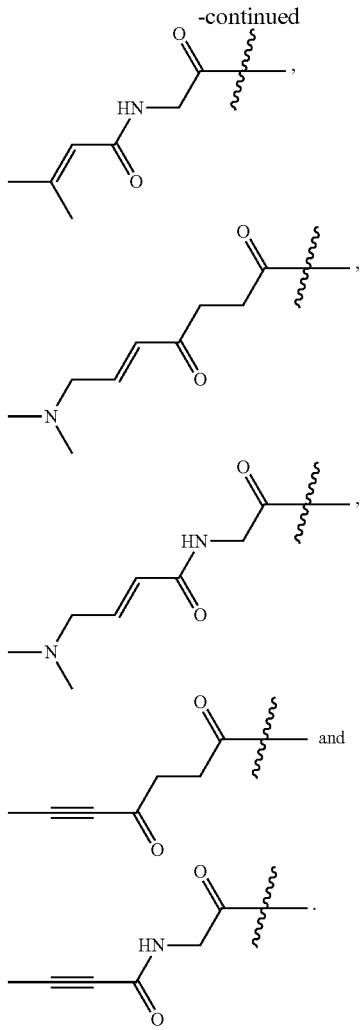

The therapeutic conjugate may be selected from the group consisting of compounds 1-131, 1-132, 1-133, 1-134, 1-135, 1-136, 1-139, 1-140, 1-141, 1-142, 1-143, 1-144, 1-147, 1-148, 1-149, 1-150, 1-151, 1-152, 1-155, 1-156, 1-157, 1-158, 1-159, 1-160, 1-163, 1-164, 1-165, 1-166, 1-167 and 1-168.

In some embodiments, a therapeutic conjugate may comprise a structure selected from Compound 1-101 to Compound 1-172, or a pharmaceutical acceptable salt thereof. In some embodiments, a therapeutic conjugate may comprise a structure selected from Compound 1-1 to Compound 1-11, or a pharmaceutical acceptable salt thereof.

In some embodiments, the present disclosure provides a pharmaceutical composition which may comprise the therapeutic conjugate disclosed herein and at least one pharmaceutically acceptable excipient.

In some embodiments, the present disclosure provides a method of regulating the activity of a kinase or pseudokinase, comprising administering the therapeutic conjugate disclosed herein. In some embodiments, the activity of the kinase or pseudokinase may be inhibited. In some embodiments, the kinase may be PI3-K.

In some embodiments, the present disclosure provides a method of treating a subject in need thereof comprising administering a therapeutically effective amount of the pharmaceutical composition described herein. The subject may have a therapeutic condition selected from the group consisting of cancer, neurodegenerative disease, autoimmune disorder and aging. In some embodiments, the subject may have cancer. In some embodiments, the subject may have a cancer with a mutation in the PIK3CA gene.

DETAILED DESCRIPTION

I. Compostions

The inventors have discovered inter alia, an Anchored Relational Covalent System, hereafter referred to as the ARCS, which comprises a Functionally Competent Binder, hereafter referred to as the FCB; a Covalent Linking Modality, hereafter referred to as the CLM, wherein the CLM is attached directly or indirectly to said therapeutic modality; and optionally a linker positioned between the FCB and the CLM. In some embodiments, a CLM is covalently attached to an FCB directly with a bond. In some embodiments, a CLM is covalently attached to an FCB indirectly with a linker.

The term "ARCS" as used herein, refers to any therapeutic conjugate that is formed by linking an FCB and a CLM with a bond or a linker. In some embodiments, the ARCS can form a covalent bond with one or multiple targets such as nucleotides, oligonucleotides, peptides, or proteins. In some embodiments, the ARCS can form a covalent bond with a biological target. The covalent bond can be detected with any known method in the art. As a non-limiting example, covalent attachment of azido-small molecules to the proteins can be detected by using click chemistry to attach heavy, PEG-containing alkynes to the small molecules. The covalently labeled proteins are detected by a gel shift that occurs because they are now PEG-labeled and have a higher molecular weight (*Biochemistry* 2018, 57:5769-5774). In another non-limiting example, mass spectrometry can be used to detect covalently-labeled, purified protein (*Nature Chemical Biology* 2007, 3:229-238). In yet another non-limiting example, cellular quantitative mass spectrometry-based proteomic methods can be used to analyze covalent bonding (*Cell Chemical Biology* 2017, 24:1388-1400.e7). In yet another non-limiting example, X-ray crystallography is used to confirm covalent bond formation (*Nature Chemical Biology* 2007, 3:229-238; *J. Med. Chem.* 2020, 63:52-65). In yet another non-limiting example, mass spectrometry of in-cell, covalently-labeled, and affinity-enriched samples can be used to reveal the site of covalent modification (*Nat. Chem. Biol.* 2016, 12:876-884).

In some embodiments, the ARCS can form a covalent bond with the biological target to a percent of about 5%-100% of the biological target. In some embodiments, the ARCS can form a covalent bond with the biological target from about 5%, 10%, 15%, 20%, 25%, 30%, 35%, 40%, 45%, 50%, 55%, 60%, 65%, 70%, 75%, 80%, 85%, 90%, 95% or 100%. In some embodiments, the covalent bond is formed in an aqueous solution at a temperature of 0-50° C., within 48 hours, and at a treatment dose of 10 mM.

Not willing to be bound to any theory, the ARCS may first form a non-covalent bond with a biological target (such as a target protein) via an FCB, and then form a covalent bond with the biological target via a CLM. In some embodiments, the efficacy of the ARCS is better than the efficacy of the FCB alone. In some embodiments, the CLM does not substantially interfere with efficacy of the FCB. In some embodiments, the FCB does not substantially interfere with covalent binding of the CLM. In some embodiments, the toxicity of the ARCS is less than the toxicity of the FCB alone.

The term "toxicity" as used herein, refers to the capacity of a substance or composition to be harmful or poisonous to a cell, tissue organism or cellular environment. Low toxicity refers to a reduced capacity of a substance or composition to be harmful or poisonous to a cell, tissue organism or cellular environment. Such reduced or low toxicity may be relative to a standard measure, relative to a treatment or relative to the absence of a treatment.

The term "FCB" as used herein, refers to a therapeutic modality that can be a known drug, a diagnostic compound, a drug candidate and a functional fragment and/or combination of any of the forgoing. The FCB encompasses free acid and free base forms; optical and tautomeric isomers; isotopes including radioisotopes and pharmaceutically acceptable salts of the drug, prodrug or fragment thereof. The FCBs may be small molecules, proteins, peptides, lipids, carbohydrates, sugars, nucleic acids, or combination thereof. In some embodiments, the FCBs are nucleic acids including, but is not limited to DNA or RNA. The FCB may be a therapeutic agent such as, but not limited to, anticancer agents, anti-neurodegenerative agents, autoimmune drugs and anti-aging agents. The FCB may bind to a biological target non-covalently. In some embodiments, the FCB may be a functional fragment of a drug. The term "functional fragment" as used herein, refers to a part of a drug or derivative or analog thereof that is capable of inducing a desired effect of the drug. In some embodiments, the FCB may comprise an alkyne functional group. In some embodiments, the FCB may not comprise an alkyne functional group.

As used herein, the term "peptide", "polypeptide", "protein" refers to a polymer composed of amino acid monomers linked by an amide bond. Amino acids may be D- or L-optical isomer. Peptides may be formed by condensation or coupling reaction with the amino group of one α-carbon carboxyl group and another amino acid. Peptides may be non-linear branched peptides or cyclic peptides. Furthermore, the peptide may be optionally modified or protected with divergent functional group or a protecting group including amino and/or carboxy termini.

Amino acid residues of the peptide are abbreviated as follows. Phenylalanine is Phe or F, leucine is Leu or L, isoleucine is Ile or I, methionine is Met or M, valine is Val or V, serine is Ser or S, proline is Pro or P, threonine is Thr or T, alanine is Ala or a, tyrosine is Tyr or Y, histidine is His or H, glutamine is Gln or Q, asparagine Asn or is N, lysine is Lys or K, aspartic acid is Asp or D, glutamic acid is Glu or E, cysteine is Cys or C, tryptophan is Trp or W, arginine is Arg or R, and glycine is Gly or G.

The term "CLM" as used herein, refers to any covalent binding modality that is capable of forming a covalent bond with the biological target. The CLM may be linked to an FCB by a bond or by a linker. The CLM may comprise one or more chemical moieties which can form a covalent bond with the biological target. The chemical moieties may be an electrophilic or nucleophilic group.

The CLM may be a small molecule having a molecular weight of less than about 1,000 Da, less than about 900 Da, less than about 800 Da, less than about 700 Da, less than about 600 Da or less than about 500 Da. In some cases, the CLM may have a molecular weight of between about 5 Da and about 1,000 Da, between about 10 Da and about 900 Da, in some embodiments between about 20 Da and about 700 Da, in some embodiments bout 20 Da and about 500 Da, between about 50 Da and about 400 Da, in some embodiments between about 100 Da and about 300 Da, and in some embodiments between about 150 Da and about 300 Da. The molecular weight of the CLM may be calculated as the sum of the atomic weight of each atom in the formula of the CLM multiplied by the number of each atom. It may also be measured by mass spectrometry, NMR, chromatography, light scattering, viscosity, and/or any other methods known in the art. It is known in the art that the unit of molecular weight may be g/mol, Dalton (Da), or atomic mass unit (amu), wherein 1 g/mol=1 Da=1 amu.

The term "biological target", as used herein, refers to any target to which an FCB binds non-covalently to product a therapeutic effect. A CLM binds to the biological target covalently. In some embodiments, the biological target is a protein. Non-limiting examples of biological targets include kinase such as, but not limited to phosphoinositide 3-kinases (PI3Ks) and pseudokinase.

In some embodiments, the ARCS can form a covalent bond with PI3-kinase. In some embodiments, the ARCS can form a covalent bond with PI3-kinase from about 5%-100% of PI3-kinase. In some embodiments, the ARCS can form a covalent bond with PI3-kinase from about 5%, 10%, 15%, 20%, 25%, 30%, 35%, 40%, 45%, 50%, 55%, 60%, 65%, 70%, 75%, 80%, 85%, 90%, 95% or 100% of PI3-kinase.

The ARCS includes at least one FCB attached to at least one CLM optionally by a linker. In some embodiments, the ARCS can be a therapeutic conjugate between a single FCB and a single CLM, e.g. having the structure X-L-Y where X is a CLM, L is an optional linker, and Y is an FCB. In some embodiments, the ARCS can be a therapeutic conjugate between a single therapeutic modality and a single covalent binding modality. In some embodiments, X is a covalent binding modality, L is an optional linker, and Y is a therapeutic modality.

In some embodiments, the ARCS contains more than one FCB, more than one linker, more than one CLM, or any combination thereof. The ARCS can have any number of FCBs, linkers, and CLMs. The ARCS can have the structure of, but not limited to, X-L-Y-L-X, $(X-L-Y)_n$, Y-L-X-L-Y, $X-(L-Y)_n$, $(X-L)_n-Y$, $(X)_n-L-Y$ or $X-L-(Y)_n$ where X is a CLM, L is an optional linker, Y is an FCB, and n is an integer between 2 and 100, between 2 and 50, between 2 and 20, for example, between 2 and 5. Each occurrence of X, L, and Y can be the same or different, e.g. the ARCS can contain more than one type of an FCB, more than one type of a linker, and/or more than one type of a CLM.

In some embodiments, the ARCS can contain more than one CLM attached to a single FCB. For example, the ARCS can include one FCB with multiple CLMs each attached via the same or different linkers. The ARCS can have the structure X-L-Y-L-X, wherein each X is the CLM that may be the same or different, each L is a linker that may be the same or different, and Y is the FCB.

In some embodiments, the ARCS can contain more than one FCB attached to a single CLM. For example, the ARCS can include one CLM with multiple FCBs each attached via the same or different linkers. The ARCS can have the structure Y-L-X-L-Y, wherein X is the CLM, each L is a linker that may be the same or different, and each X is an FCB that may be the same or different.

In some embodiments, ARCS is a therapeutic conjugate, wherein the therapeutic conjugate comprises
a. a therapeutic modality, said therapeutic modality selected from the group consisting of one or more of a known drug, a diagnostic compound, a drug candidate and a functional fragment and/or combination of any of the forgoing;

b. a covalent binding modality, said covalent binding modality comprising one or more chemical moieties, one or more of which are capable of forming a covalent bond with a biological target, wherein said covalent binding modality is attached directly or indirectly to said therapeutic modality; and c. optionally, a linker positioned between said therapeutic modality and said covalent binding modality.

In some embodiments, the therapeutic conjugate comprises a formula selected from the group consisting of a) X-L-Y, b) X-L-Y-L-X, c) $(X-L-Y)_n$, d) Y-L-X-L-Y, e) $X-(L-Y)_n$, f) $(X-L)_n-Y$, g) $(X)_n-L-Y$ and h) $X-L-(Y)_n$;

wherein X is the covalent binding modality, L is the optional linker, Y is the therapeutic modality, and n is an integer between 2 and 100.

It is an object of the disclosure to design the ARCS and its compositions, and methods of synthesizing the ARCS and a library of the ARCSs.

It is also an object of the disclosure to provide methods of screening a library of the ARCS to identify candidates for covalent binding to a biological target.

A further object of the disclosure is to provide methods of administering and using the ARCS and its compositions to individuals in need thereof.

A. FCB

The ARCS of the present disclosure contains at least one FCB. The ARCS of the present disclosure can contain more than one FCB, that can be the same or different. FCB can be a therapeutic modality that affects any biological process and is used in the prevention, diagnosis, alleviation, treatment or cure of a disease condition. The FCB can be a therapeutic, prophylactic, diagnostic, or a nutritional agent. The efficacy of FCB or ARCS refers to the effectiveness of FCB or ARCS for its intended purpose, i.e., the ability of a given FCB or ARCS to cause its desired pharmacologic effect. The term "pharmacologic activity" as used herein, means an activity that modulates or alters a biological process to result in a phenotypic change, e.g., cell death, reduced cell proliferation, etc In some embodiments, the FCB is a PI3-kinase inhibitor. In some embodiments, the FCB is a pyrrolo[2,1-F[1,2,4] triazine compound. In some embodiments, the FCB is a PI3-kinase inhibitor having any one of formulas from the U.S. Pat. No. 9,724,352 B2, the contents of which are incorporated herein by reference in their entirety. In some embodiments, the FCB is any of the compounds shown in Table 1 of the U.S. Pat. No. 9,724,352 B2. In some embodiments, the FCB comprises a structure of

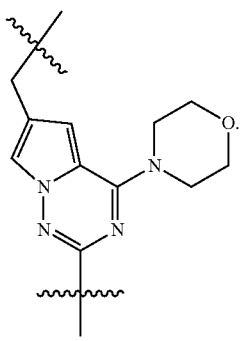 [SMILES: *Cc1cc2c(N3CCOCC3)nc(*)nn2c1]

In some embodiments, the FCB is a compound having the structure,

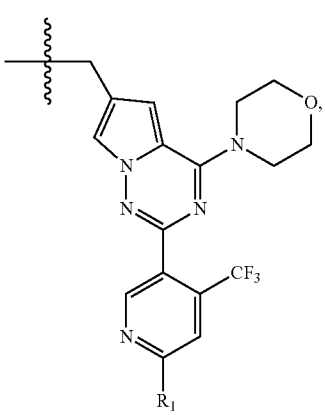

wherein R1 is selected from the group consisting of

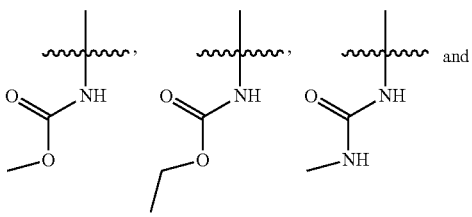

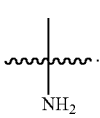

In some embodiments, the FCB is a compound having the structure,

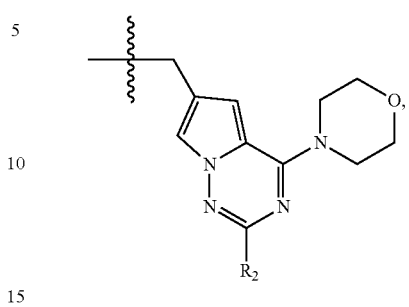

wherein R2 is selected from the group consisting of

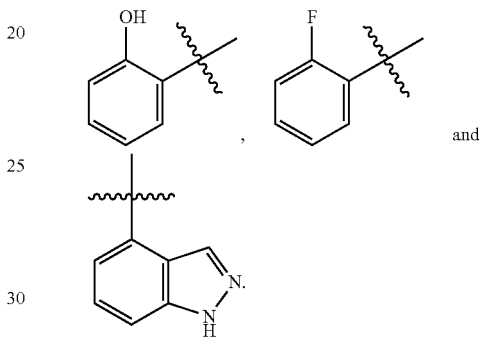

In general, the efficacy of FCB is achieved by non-covalently binding to a biological target. The non-covalent binding is achieved through some degree of specificity and/or affinity for the target. Both specificity and affinity are generally desirable, although in certain cases higher specificity may compensate for lower affinity and higher affinity may compensate for lower specificity. Affinity and specificity requirements will vary depending upon various factors including, but not limited to, absolute concentration of the target, relative concentration of the target (e.g., in cancer vs. normal cells), potency and toxicity, route of administration, and/or diffusion or transport into a target cell. At a molecular or cellular level, an effect of the FCB (in ARCS or alone) can include, but is not limited to, promotion or inhibition of the target's activity, labeling of the target, and/or a change of the target cell (e.g., cell death).

In some embodiments, FCB may be small molecules, proteins, peptides, lipids, carbohydrates, sugars, nucleic acids, or combination thereof. In some embodiments, FCB may be a therapeutic agent such as, but not limited to, anti-cancer agents, anti-neurodegenerative agents, autoimmune drugs and anti-aging agents. A variety of therapeutic agents are known in the art and may be used in the compositions as described herein.

In some embodiments, an FCB is a small molecule. In some embodiments, an FCB can be a protein, peptide or a nucleic acid. In some embodiments, an FCB can be a lipid. In some embodiments, an FCB may be a carbohydrate or sugar. In some embodiments, the FCB has an alkyne group. In some embodiments, the FCB may not have an alkyne group.

In some embodiments, the FCB may be a functional fragment of a drug. The term "functional fragment" or "core of the drug" as used herein, refers to a part of a drug or derivative or analog thereof that is capable of inducing a desired effect of the drug.

In some embodiments, FCB may bind to a biological target non-covalently. In some embodiments, FCB may bind to a biological target with an $IC_{50}$ of <1000 μm, 900 μm, 800 μm, 700 μm, 600 μm, or 500 μm.

In some embodiments, the FCB is an anti-cancer agent. In some embodiments, the FCB is an anti-neurodegenerative agent. In some embodiments, the FCB is an autoimmune drug. In some embodiments, the FCB is an anti-aging agent.

In certain embodiments, the FCB of the ARCS comprises a predetermined molar weight percentage from about 1% to about 10%, or about 10% to about 20%, or about 20% to about 30%, or about 30% to about 40%, or about 40% to about 50%, or about 50% to about 60%, or about 60% to about 70%, or about 70% to about 80%, or about 80% to about 90%, or about 90% to about 99% such that the sum of the molar weight percentages of the components of the ARCS is 100%. The amount of FCB(s) of the ARCS may also be expressed in terms of proportion to the CLM(s). For example, the present teachings provide a ratio of FCB to CLM of about 10:1, 9:1, 8:1, 7:1, 6:1, 5:1, 4:1, 3:1, 2:1, 1:1, 1:2, 1:3, 1:4; 1:5, 1:6, 1:7, 1:8, 1:9, or 1:10.

B. CLM

The ARCS of the present disclosure contains one or more CLM(s). The CLM can be any covalent binding modality that is capable of forming a covalent bond with a biological target. The CLM may comprise one or more chemical moieties, one or more of which are capable of forming a covalent bond with a biological target. In certain embodiments, the CLM may comprise an internal linker or spacer. The internal linker or spacer may combine two parts of the CLM or can be joined to the CLM.

In some embodiments, the CLM is a small molecule. In some embodiments, the CLM has a molecular weight of less than about 1000 Dalton (e.g., less than about 900, 800, 750, 700, 650, 600, 550, 500, 450, 400, 350, 300, 250, 200, 150, 100, etc.).

In certain embodiments, the CLM of the ARCS comprises a predetermined molar weight percentage from about 1% to about 10%, or about 10% to about 20%, or about 20% to about 30%, or about 30% to about 40%, or about 40% to about 50%, or about 50% to about 60%, or about 60% to about 70%, or about 70% to about 80%, or about 80% to about 90%, or about 90% to about 99% such that the sum of the molar weight percentages of the components of the ARCS is 100%. The amount of CLM(s) of the ARCS may also be expressed in terms of proportion to the FCB(s). For example, the present teachings provide a ratio of FCB to CLM of about 10:1, 9:1, 8:1, 7:1, 6:1, 5:1, 4:1, 3:1, 2:1, 1:1, 1:2, 1:3, 1:4; 1:5, 1:6, 1:7, 1:8, 1:9, or 1:10.

In some embodiments, the CLM comprises at least one substituted or unsubstituted alkyne. In some embodiments, the CLM comprises at least one substituted or unsubstituted acrylamide. In some embodiments, the CLM comprises at least one substituted or unsubstituted vinyl sulfonamide. In some embodiments, the CLM comprises at least one substituted or unsubstituted vinyl sulfone. In some embodiments, the CLM comprises at least one substituted or unsubstituted fumaramide. In some embodiments, the CLM comprises at least one substituted or unsubstituted acrylate. In some embodiments, the CLM comprises at least one substituted or unsubstituted isothiocyanate. In some embodiments, the CLM comprises at least one substituted or unsubstituted sulfonyl fluoride. In some embodiments, the CLM comprises at least one substituted or unsubstituted fluorosulfate. In some embodiments, the CLM comprises at least one substituted or unsubstituted formyl phenyl boronic acid. In some embodiments, the CLM comprises at least one substituted or unsubstituted boronic acid. In some embodiments, the CLM comprises at least one activated ester. In some embodiments, the CLM comprises at least one substituted or unsubstituted thioester. In some embodiments, the CLM comprises at least one sulfonyl group. In some embodiments, the CLM comprises at least one nitro group. In some embodiments, the CLM comprises at least one substituted or unsubstituted epoxide. In some embodiments, the CLM comprises at least one substituted or unsubstituted formyl phenyl boronic acid. In some embodiments, the CLM comprises at least one substituted or unsubstituted aryl halide. In some embodiments, the CLM comprises at least one substituted or unsubstituted aldehyde. In some embodiments, the CLM comprises at least one substituted or unsubstituted triazine. In some embodiments, the CLM comprises at least one substituted or unsubstituted cyanoacrylamide. In some embodiments, the CLM comprises at least one substituted or unsubstituted chloroacetamide.

Exemplary CLMs include, but not limited to

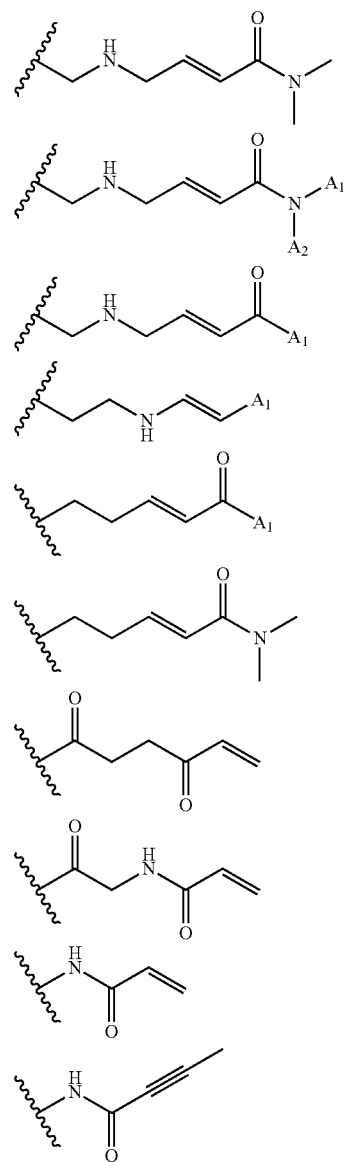

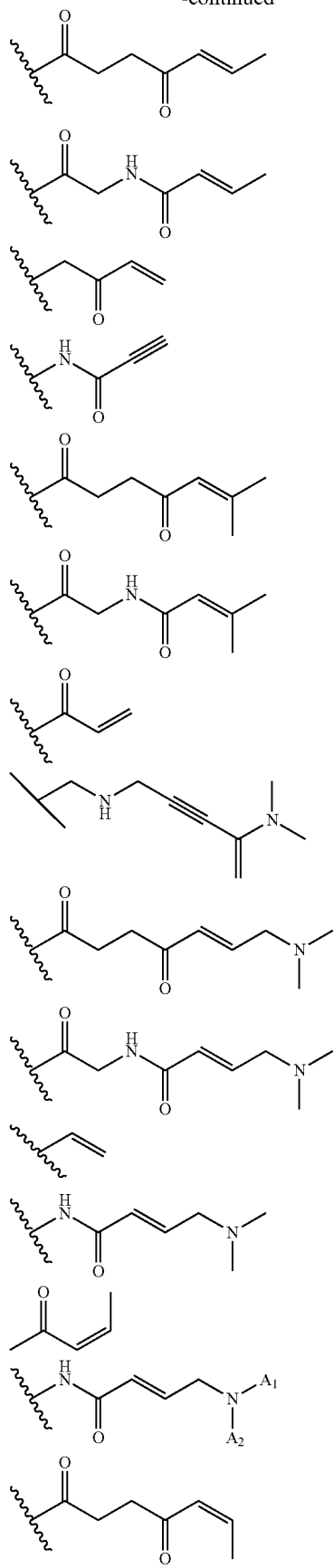
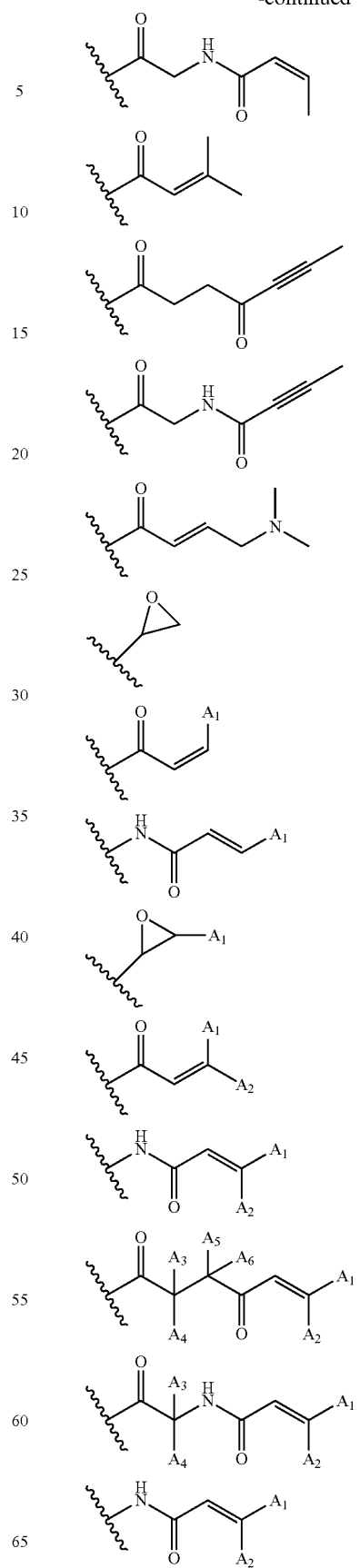

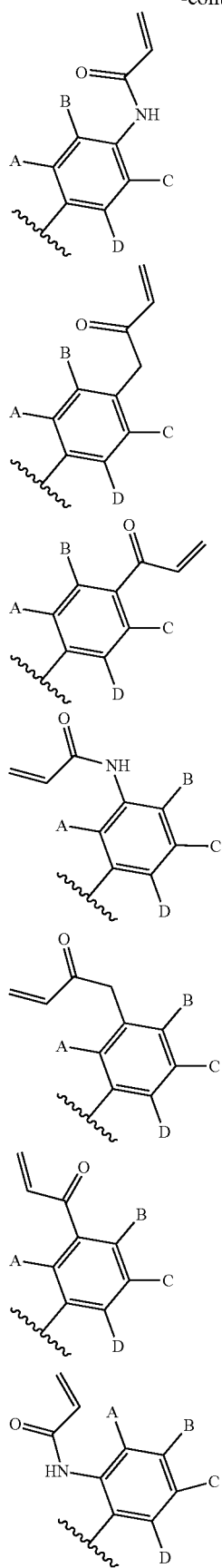
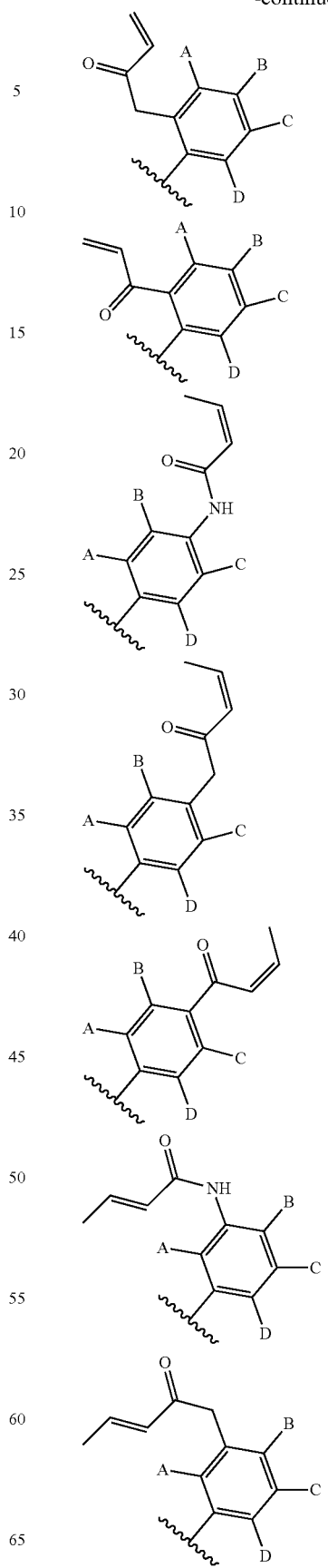

-continued
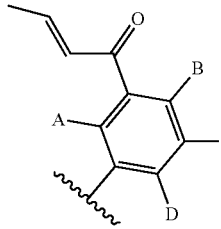
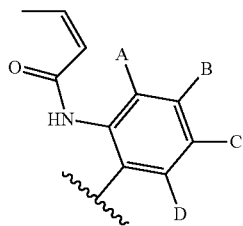
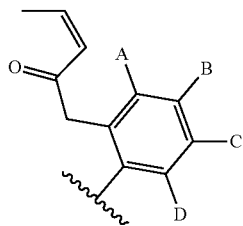
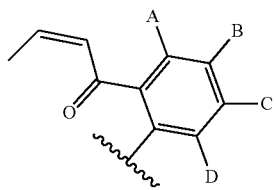
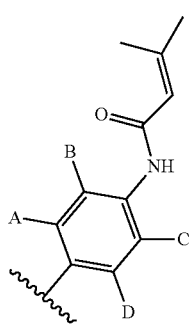
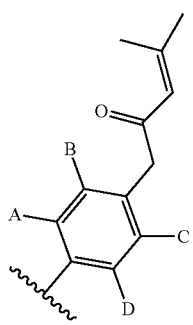
-continued
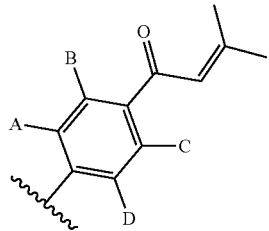
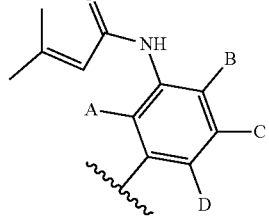
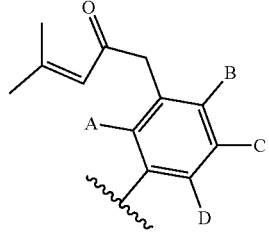
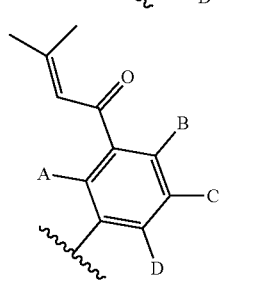
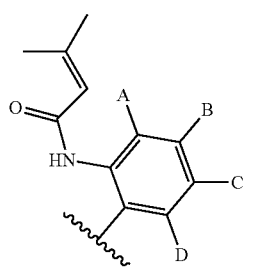
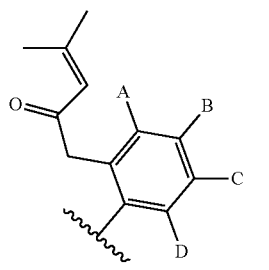
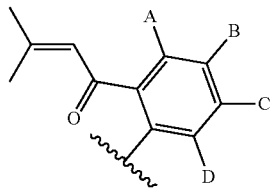

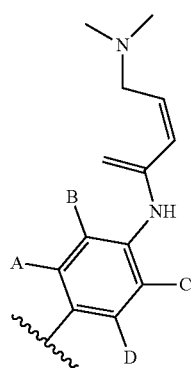
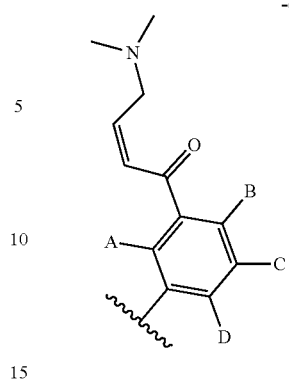
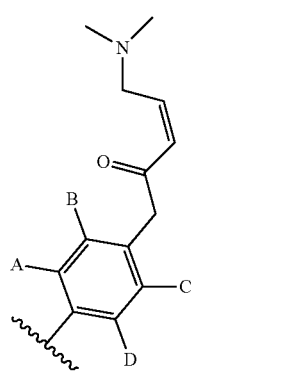
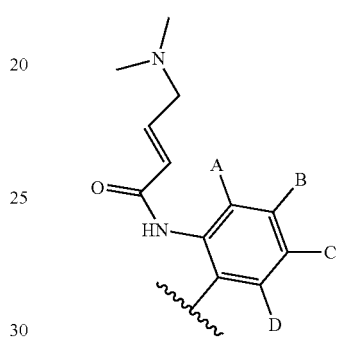
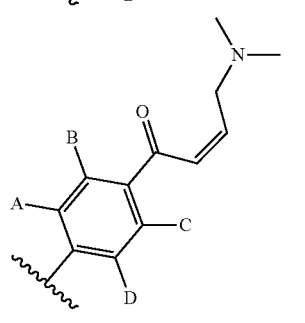
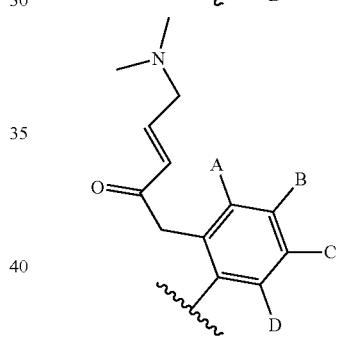
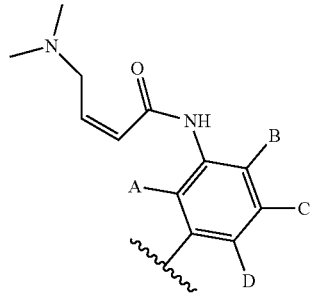
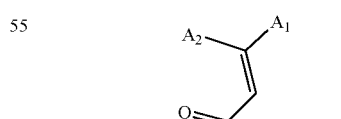
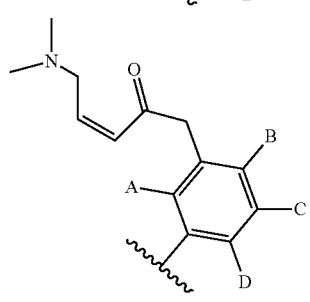
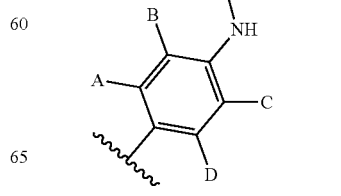

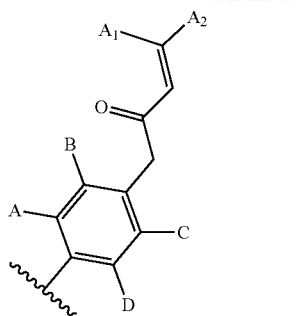
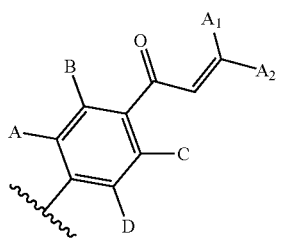
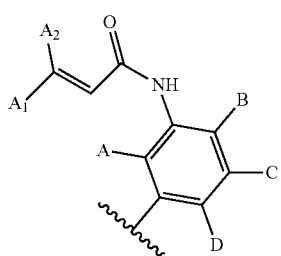
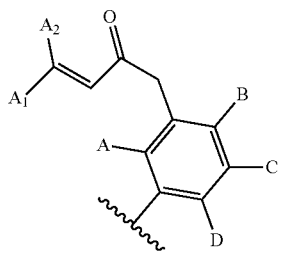
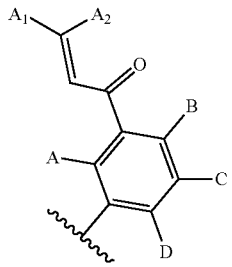
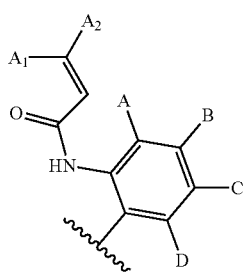
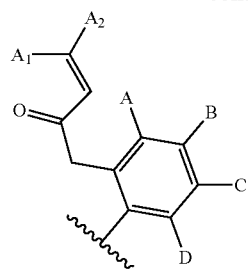
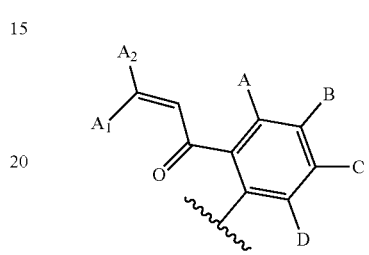
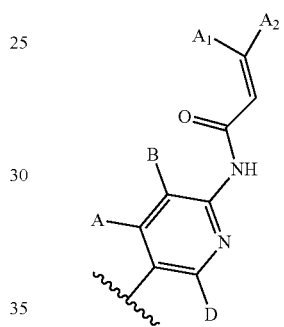
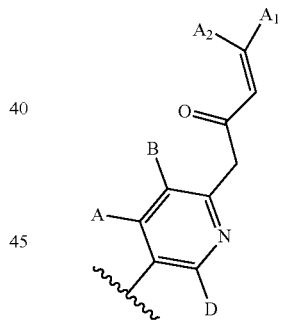
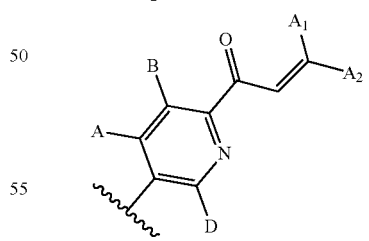
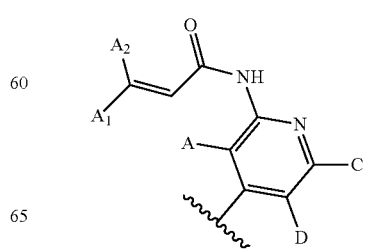

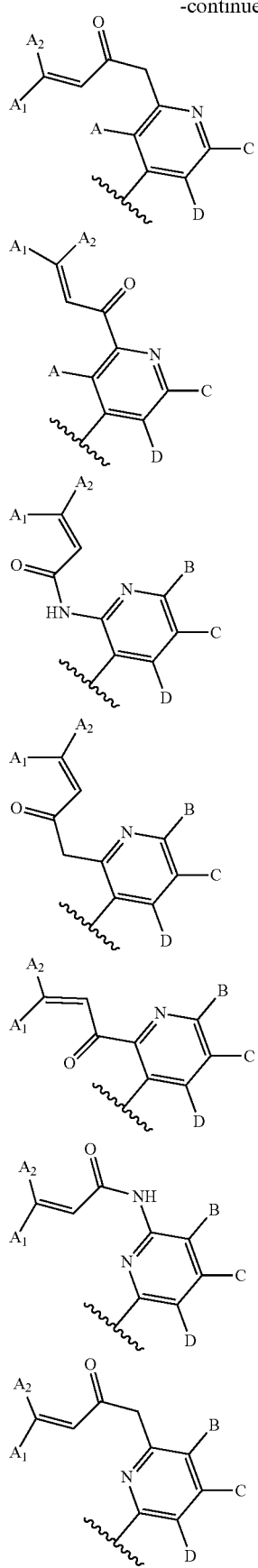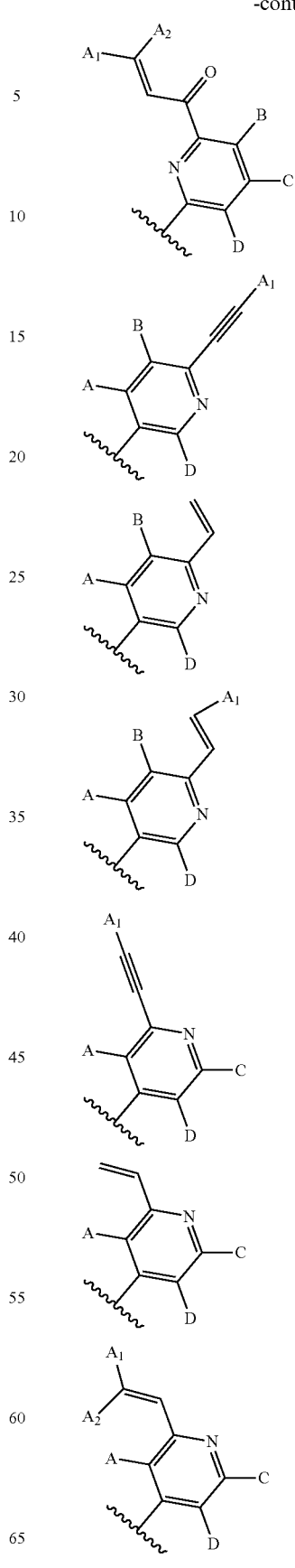

-continued
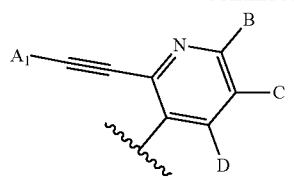
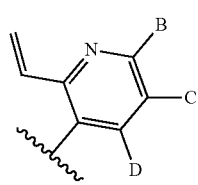
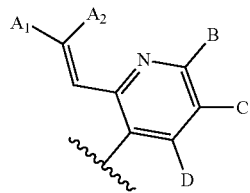
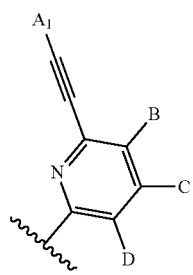
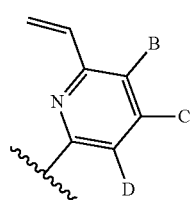
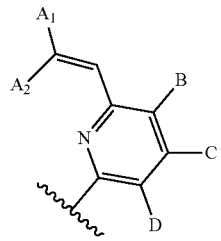
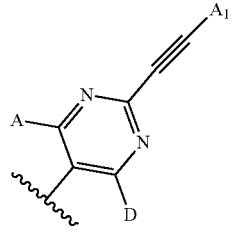
-continued
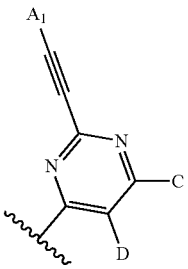
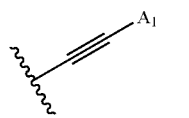
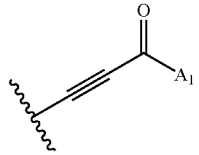
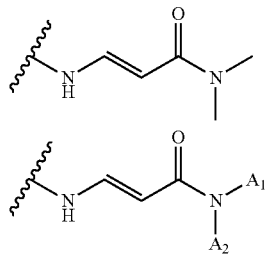
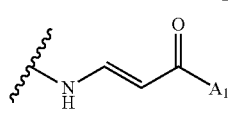
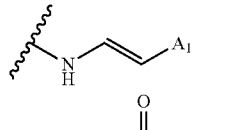
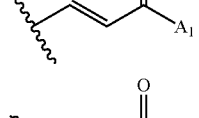
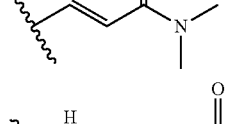
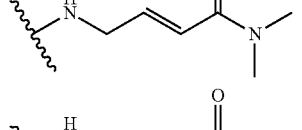
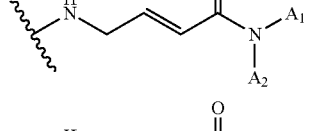
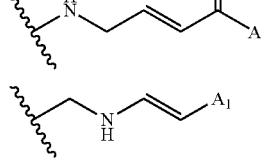
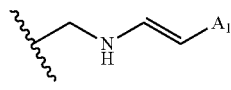

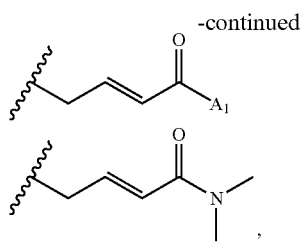

wherein A, B, C and D at each occurrence is independently selected from the group consisting of H, halogen, CF₃, —OH, —NH₂, —SH, —SCH₃, —CN, —NO₂, —CH₂(NH₂), —C(O)OH, —S(O)₂NH₂, —C(O)NH₂, —C(O)CH₃, NHC(O)—C$_{1-6}$ alkyl, N(C$_{1-3}$ alkyl)C(O)—C$_{1-6}$ alkyl, OC(O)NH₂, OC(O)NH(CH₃), OC(O)N(CH₃)₂, imidazolyl, pyrazolyl, methylimidazolyl, methylpyrazolyl, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted 5-10 membered heterocycle, optionally substituted aryl, and optionally substituted 5-10 membered heteroaryl, wherein the optional substituents for A, B, C, and D are 1-3 substituents which are independently selected from the group consisting of halogen, OH, NH₂, CH₃, CF₃, —CN, —NO₂, —C(O)OH, —S(O)₂NH₂, —C(O)NH₂, —CH₂NH₂, —C(O)CH₃, SH, —S—CH₃, optionally substituted C$_{1-3}$ alkyl, and optionally substituted C$_{3-6}$ cycloalkyl.

A₁, A₂, A₃, A₄, A₅, and A₆ at each occurrence are independently selected from the group consisting of H, halogen, CF₃, —OH, —NH₂, —SH, —SCH₃, —CN, —NO₂, —CH₂(NH₂), —C(O)OH, —S(O)₂NH₂, —C(O)NH₂, —C(O)CH₃, NHC(O)—C$_{1-6}$ alkyl, N(C$_{1-3}$ alkyl)C(O)—C$_{1-6}$ alkyl, OC(O)NH₂, OC(O)NH(CH₃), OC(O)N(CH₃)₂, imidazolyl, pyrazolyl, methylimidazolyl, methylpyrazolyl, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted 5-10 membered heterocycle, optionally substituted aryl, and optionally substituted 5-10 membered heteroaryl, wherein the optional substituents for A₁, A₂, A₃, A₄, A₅, and A₆ are 1-3 substituents which are independently selected from the group consisting of halogen, OH, NH₂, CH₃, CF₃, —CN, —NO₂, —C(O)OH, —S(O)₂NH₂, —C(O)NH₂, —CH₂NH₂, —C(O)CH₃, SH, —S—CH₃, optionally substituted C$_{1-3}$ alkyl, and optionally substituted C$_{3-6}$ cycloalkyl, and wherein the C$_{1-3}$ alkyl and C$_{3-6}$ cycloalkyl optional substituents are 1-2 substituents, which are independently selected from the group consisting of halogen, OH, NH₂, CH₃, CF₃, —CN, —NO₂, —C(O)OH, —S(O)₂NH₂, —C(O)NH₂, —CH₂NH₂, —C(O)CH₃, SH, and —S—CH₃, or a fragment, derivative or analog thereof.

In some embodiments, the CLM is selected from the group consisting of

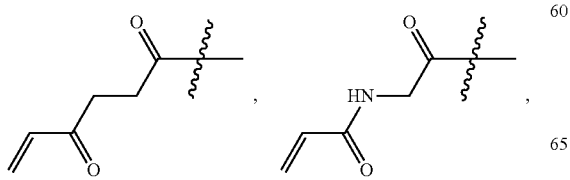

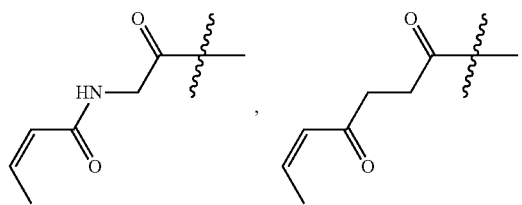

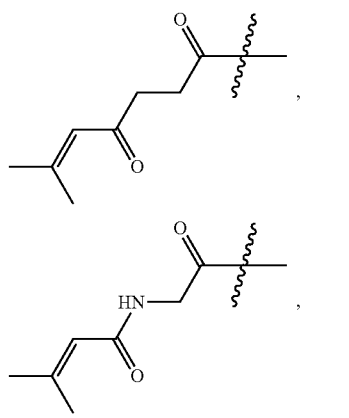

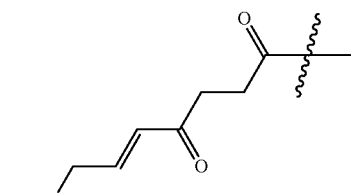

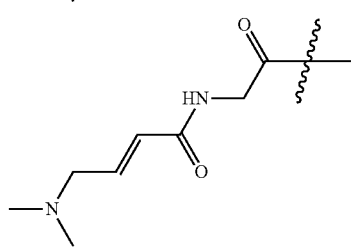

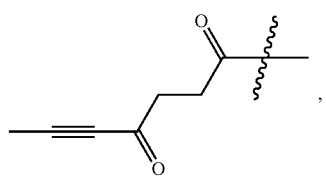

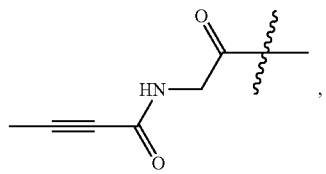

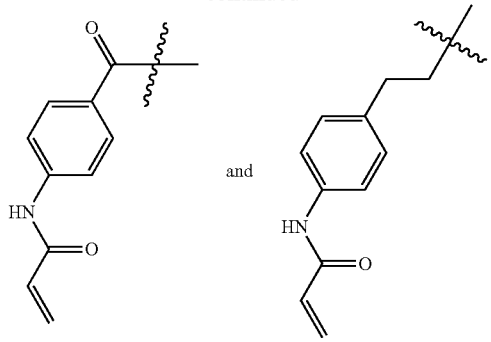

C. Linkers

The ARCS of the present disclosure contains one or more optional linkers connecting the FCB(s) and CLM(s). The linker, L, can be attached to anywhere on FCB and CLM, as long as the efficacy of FCB and the binding of CLM are not significantly affected. In some embodiments, CLM comprises an optional internal linker.

In some embodiments, the linker (including the internal linker of CLM) is a small molecule. In some embodiments, the linker (including the internal linker of CLM) is selected, but not limited to substituted and unsubstituted $C_1$-$C_{30}$ alkyl, substituted and unsubstituted $C_2$-$C_{30}$ alkenyl, substituted and unsubstituted $C_2$-$C_{30}$ alkynyl, substituted and unsubstituted $C_3$-$C_{30}$ cycloalkyl, substituted and unsubstituted $C_1$-$C_{30}$ heterocycloalkyl, substituted and unsubstituted $C_3$-$C_{30}$ cycloalkenyl, substituted and unsubstituted $C_1$-$C_{30}$ heterocycloalkenyl, substituted and unsubstituted aryl, and substituted and unsubstituted heteroaryl.

In some embodiments, the linker (including the internal linker of CLM) can be a $C_1$-$C_{10}$ straight chain alkyl, $C_1$-$C_{10}$ straight chain O-alkyl, $C_1$-$C_{10}$ straight chain substituted alkyl, $C_1$-$C_{10}$ straight chain substituted O-alkyl, $C_4$-$C_{13}$ branched chain alkyl, $C_4$-$C_{13}$ branched chain O-alkyl, $C_2$-$C_{12}$ straight chain alkenyl, $C_2$-$C_{12}$ straight chain O-alkenyl, $C_3$-$C_{12}$ straight chain substituted alkenyl, $C_3$-$C_{12}$ straight chain substituted O-alkenyl, polyethylene glycol, polylactic acid, polyglycolic acid, poly(lactide-co-glycolide), polycarprolactone, polycyanoacrylate, ketone, aryl, heterocyclic, succinic ester, amino acid, aromatic group, ether, crown ether, urea, thiourea, amide, purine, pyrimidine, bipyridine, indole derivative acting as a cross linker, chelator, aldehyde, ketone, bisamine, bis alcohol, heterocyclic ring structure, azirine, disulfide, thioether, hydrazone and combinations thereof. For example, the linker can be a $C_3$ straight chain alkyl or a ketone. The alkyl chain of the linker can be substituted with one or more substituents or heteroatoms. In some embodiments the linker contains one or more atoms or groups selected from —O—, —C(=O)—, —NR, —O—C(=O)—NR—, —S—, —S—S—. The linker may be selected from dicarboxylate derivatives of succinic acid, glutaric acid or diglycolic acid.

In some embodiments the alkyl chain of the linker may optionally be interrupted by one or more atoms or groups selected from —O—, —C(=O)—, —NR, —O—C(=O)—NR—, —S—, —S—S—. The linker may be selected from dicarboxylate derivatives of succinic acid, glutaric acid or diglycolic acid.

In some embodiments, the linker may be non-cleavable. In some embodiments, the linker may be cleavable. In some embodiments, the linker may be cleaved by an enzyme.

Non-limiting examples of linkers include

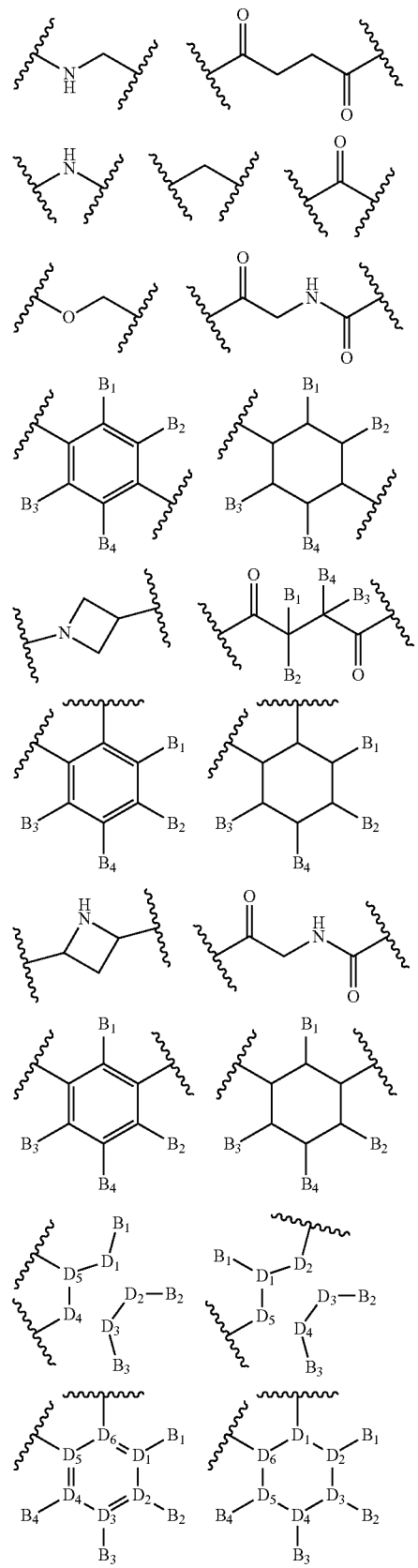

-continued

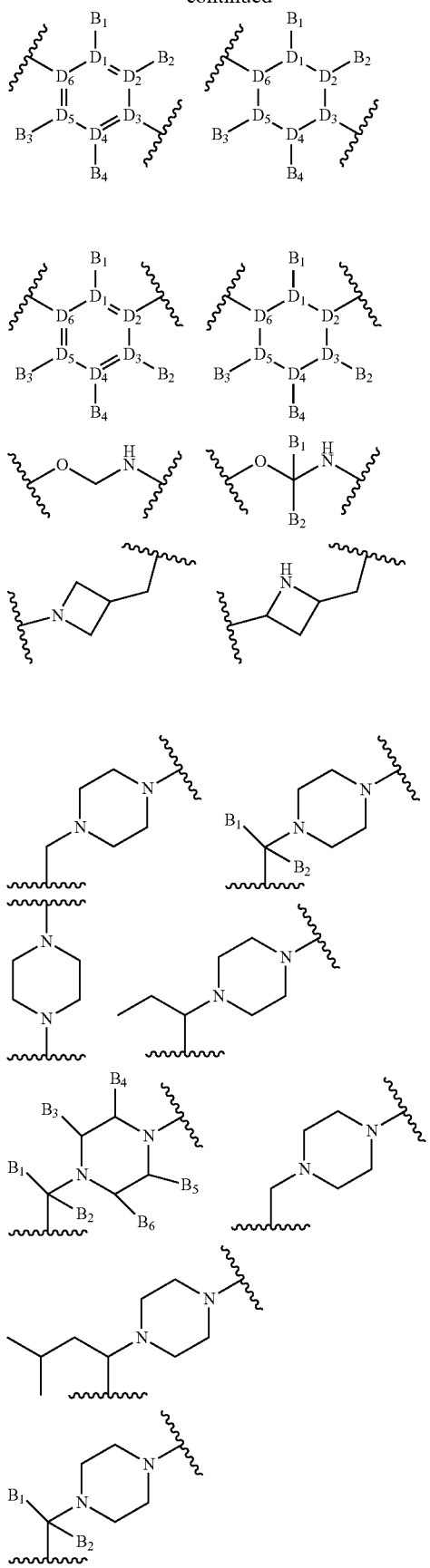

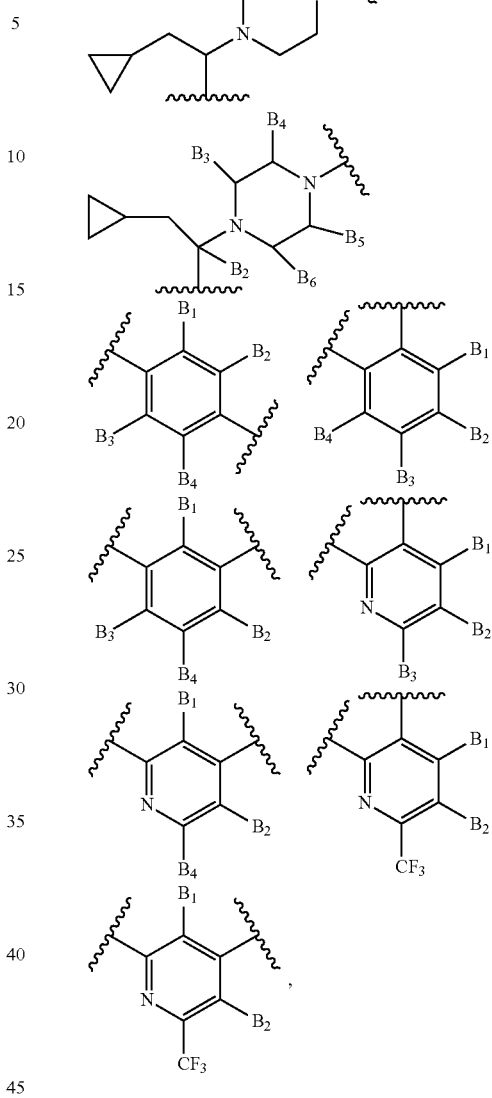

wherein $D_1$, $D_2$, $D_3$, $D_4$, $D_5$ and $D_6$ at each occurrence are independently selected from the group consisting of N, C, O, or S, provided that if $D_{1-6}$ is a N, the corresponding position is trivalent; if $D_{1-6}$ is a O or S, the corresponding position is divalent; wherein $B_1$, $B_2$, $B_3$, $B_4$, $B_5$, and $B_6$ at each occurrence is absent or independently selected from the group consisting of H, halogen, $CF_3$, —OH, —$CH_3$, —$NH_2$, —SH, —$SCH_3$, —CN, —$NO_2$, —$CH_2(NH_2)$, —C(O)OH, —$S(O)_2NH_2$, —$C(O)NH_2$, —$C(O)CH_3$, NHC(O)—$C_{1-6}$ alkyl, $N(C_{1-3}$ alkyl)C(O)—$C_{1-6}$ alkyl, $OC(O)NH_2$, $OC(O)NH(CH_3)$, $OC(O)N(CH_3)_2$, imidazolyl, pyrazolyl, methylimidazolyl, methylpyrazolyl, optionally substituted $C_{1-6}$ alkyl, optionally substituted $C_{2-6}$alkenyl, optionally substituted $C_{2-6}$ alkynyl, optionally substituted $C_{3-6}$cycloalkyl, optionally substituted 5-10 membered heterocycle, optionally substituted aryl, and optionally substituted 5-10 membered heteroaryl, wherein the optional substituents for $B_1$, $B_2$, $B_3$, and $B_4$ are 1-3 substituents independently selected from the group consisting of halogen, OH, $NH_2$, $CH_3$, $CF_3$, —CN, —$NO_2$, —C(O)OH, —$S(O)_2NH_2$, —$C(O)NH_2$, —$CH_2NH_2$, —$C(O)CH_3$, SH, —S—$CH_3$, optionally substituted $C_{1-3}$ alkyl, and optionally substituted $C_{3-6}$ cycloalkyl, and wherein the $C_{1-3}$ alkyl and $C_{3-6}$ cycloalkyl optional substituents are 1-2 substituents independently selected from the group consisting of halogen, OH, $NH_2$, $CH_3$, $CF_3$, —CN, —$NO_2$, —C(O)OH, —$S(O)_2NH_2$, —C(O)$NH_2$, —$CH_2NH_2$, —C(O)$CH_3$, SH, and —S—$CH_3$, or any fragments or analogs thereof.

In some embodiments, the linker is selected from the group consisting of

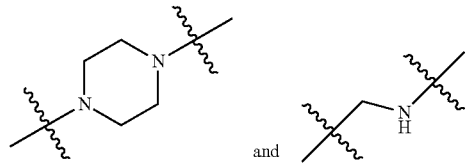

wherein either end can be connected to the CLM. In some embodiments, the linker selected from the group consisting of

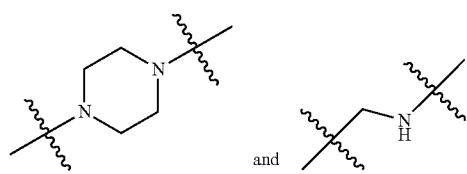

is connected to the CLM selected from the group consisting of

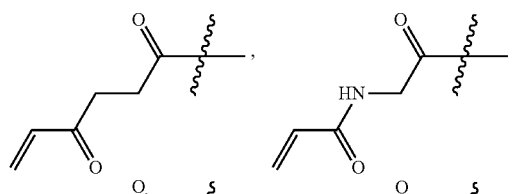

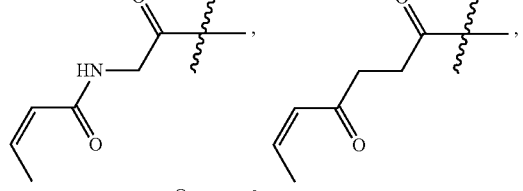

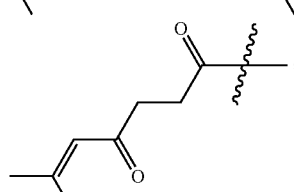

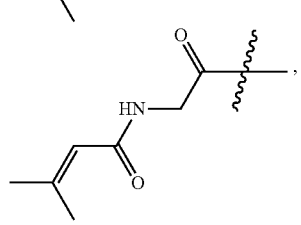

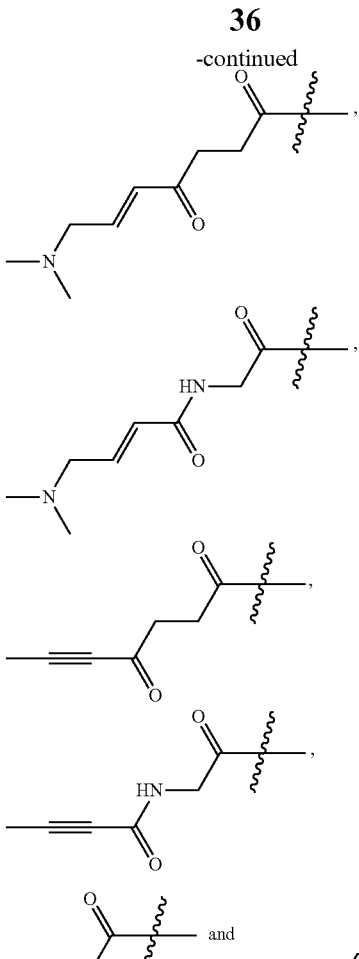

D. ARCS

The ARCS of the present disclosure represents a class of drugs that have many advantages, such as an increased potency and extended duration of action, when compared to the reversible inhibitors. The present disclosure provides therapeutic conjugates that form a covalent bond with a kinase or pseudokinase. In some embodiments, the kinase is PI3-kinase (PI3K). The therapeutic conjugate may have a structure of (FCB)a-(L)b-(CLM)c, wherein a and c are, independently, integers between 1 and 5, b is an integer between 0 and 5, and wherein the FCB moiety comprises a PI3K inhibitor, or a fragment, analog or derivative thereof.

The FCB moiety, L (linker) moiety, and CLM moieties are discussed in the sections above. In one non-limiting example, the FCB comprises

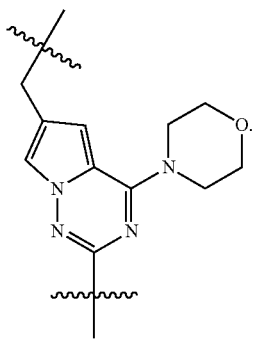 [SMILES: *Cc1cc2c(N3CCOCC3)nc(*)nn2c1]

In some embodiments, the FCB is a compound having the structure,

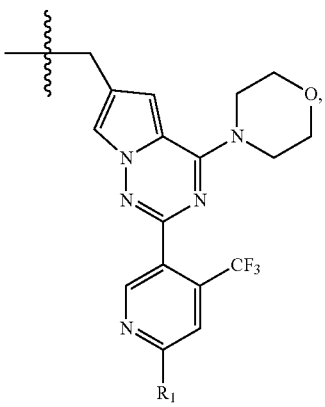

wherein R1 is selected from the group consisting of

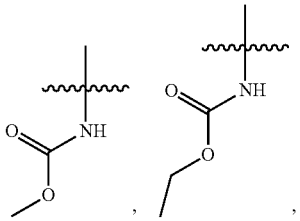

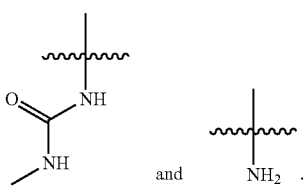

In some embodiments, the FCB is a compound having the structure,

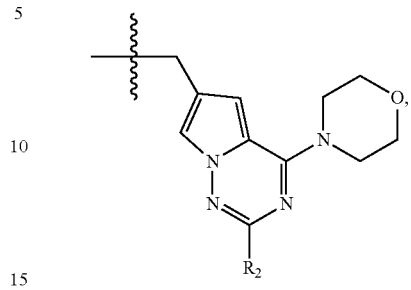

wherein R2 is selected from the group consisting of

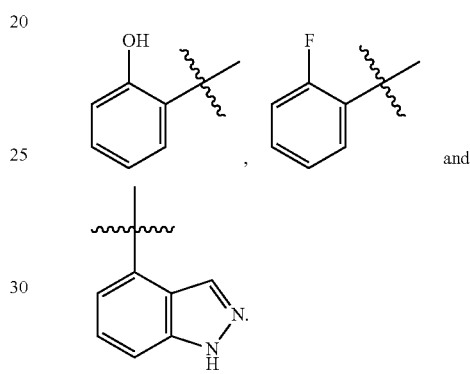

In some embodiments, the linker is selected from the group consisting of

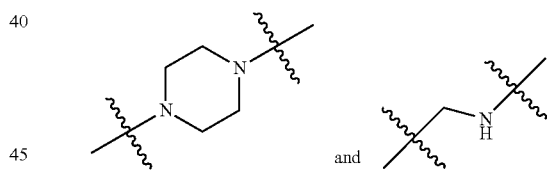

wherein either end can be connected to the CLM. In some embodiments, the CLM is selected from the group consisting of

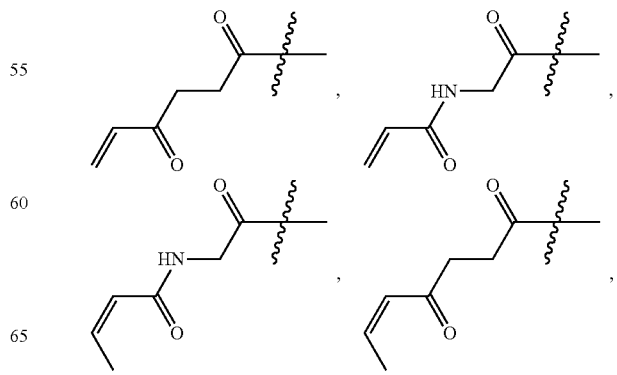

-continued
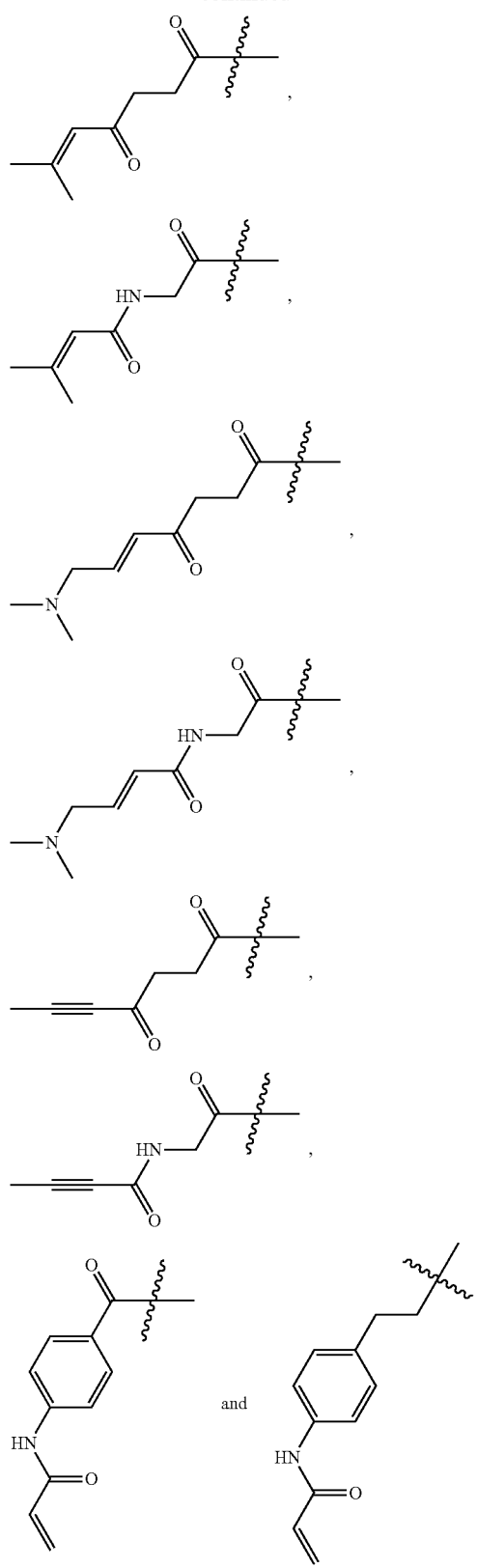
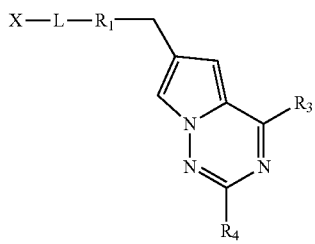
Compound 1-1
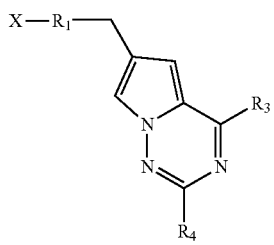
Compound 1-2
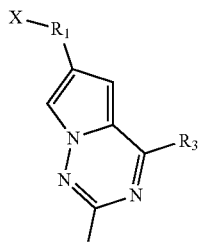
Compound 1-3
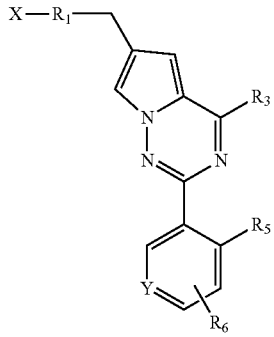
Compound 1-4
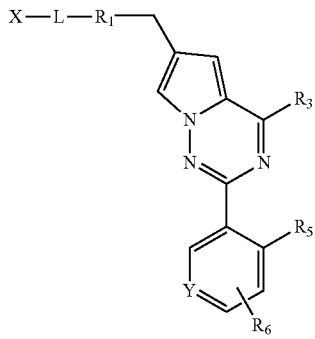
Compound 1-5
In some embodiments, the ARCS is selected from the group consisting of broad generic structures Compound 1-1 to Compound 1-5, or a pharmaceutically acceptable salt thereof, wherein $R_1$ at each occurrence is independently selected from the group

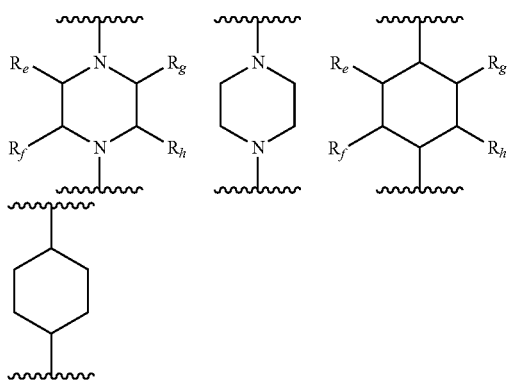

consisting of

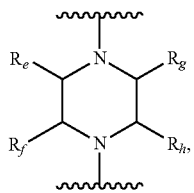

wherein R₁ can be attached to X, L or the functional fragment of the drug in either of the two ends. For example, in

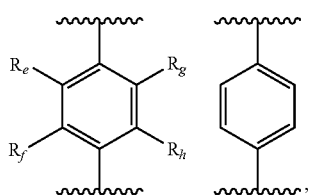

R₁ can be attached to L either from the end adjacent to $R_e$ and $R_g$ and to the functional fragment of the drug from the end adjacent to $R_f$ and $R_h$; or R₁ can be attached to L either from the end adjacent to $R_f$ and $R_h$ and to the functional fragment of the drug from the end adjacent to $R_e$ and $R_g$ in Compound 1-1.

In some embodiments, R₁ at each occurrence is independently selected from the group consisting of unsubstituted or substituted -(alk)$_a$-S-(alk)$_b$-, -(alk)$_a$-O-(alk)$_b$-, -(alk)$_a$-NR$^A$-(alk)$_b$-, -(alk)$_a$-C(O)-(alk)$_b$-, -(alk)$_a$-C(S)-(alk)$_b$-, -(alk)$_a$-S(O)-(alk)$_b$-, -(alk)$_a$-S(O)$_2$-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)NR$^A$-(alk)$_b$-, -(alk)$_a$-C(S)NR$^A$-(alk)$_b$-, -(alk)$_a$-S(O)$_2$NR$^A$-(alk)$_b$-, -(alk)$_a$-NR$^A$C(O)-(alk)$_b$-, -(alk)$_a$-NR$^A$C(S)-(alk)$_b$-, -(alk)$_a$-NR$^A$S(O)$_2$-(alk)$_b$-, -(alk)$_a$-NR$^A$C(O)O-(alk)$_b$-, -(alk)$_a$-NR$^A$C(S)O-(alk)$_b$-, -(alk)$_a$-OC(O)NR$^A$-(alk)$_b$-, -(alk)$_a$-OC(S)NR$^A$-(alk)$_b$-, -(alk)$_a$-NR$^A$C(O)NR$^B$-(alk)$_b$-, -(alk)$_a$-NR$^A$C(S)NR$^B$-(alk)$_b$-, and -(alk)$_a$-NR$^A$S(O)$_2$NR$^B$-(alk)$_b$-;

a and b are independently selected from the group consisting of 0, 1, 2, 3, and 4;

alk is independently selected from the group consisting of $C_{1-5}$ alkylene, $C_{1-5}$ alkenylene, and $C_{1-5}$ alkynylene, each of which is optionally substituted with 1-3 substituents independently selected from the group consisting of H, halogen, —OH, NH₂, CF₃, $C_{1-5}$ alkyl, —CH₂(NH₂), —CN, —NO₂, —C(O)OH, —S(O)₂NH₂, —C(O)NH₂, —C(O)CH₃, —SH, imidazolyl, pyrazolyl, methylimidazolyl, methylpyrazolyl, —O—$C_{1-5}$ alkyl, —S—$C_{1-5}$ alkyl, —NH—$C_{1-5}$ alkyl, and —N($C_{1-5}$ alkyl)₂, wherein the $C_{1-5}$ alkyl groups are independently optionally substituted with 1-3 groups selected from the group consisting of halogen, —OH, —NH₂, $C_{1-4}$ alkyl, CF₃, —CH₂(NH₂), —CN, —NO₂, —C(O)OH, —S(O)₂NH₂, —C(O)NH₂, —C(O)CH₃, —SH, —SCH₃, imidazolyl, pyrazolyl, methylimidazolyl, and methylpyrazolyl;

R$^A$ and R$^B$, at each occurrence, are independently selected from the group consisting of hydrogen, $C_{1-3}$ alkyl, $C_{3-6}$ cycloalkyl, 5-10 membered heterocycle, aryl, and 5-10 membered heteroaryl, wherein the alkyl, cycloalkyl, heterocycle, aryl, and heteroaryl are each independently optionally substituted with 1-3 substituents selected from the group consisting of halogen, $C_{1-3}$ alkyl, OH, NH₂, NH—$C_{1-3}$ alkyl, N($C_{1-3}$ alkyl)₂, CF₃, $C_{1-6}$ alkyl, —CH₂(NH₂), —CN, —NO₂, —C(O)OH, —S(O)₂NH₂, —C(O)NH₂, —C(O)CH₃, —SH, —SCH₃, imidazolyl, pyrazolyl, methylimidazolyl, and methylpyrazolyl;

R₃ at each occurrence is independently selected from the group consisting of:

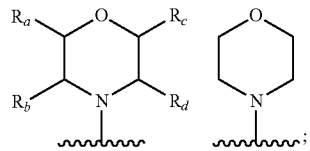

$R_a$, $R_b$, $R_c$, $R_d$, $R_e$, $R_f$, $R_g$, and $R_h$ at each occurrence are independently selected from the group consisting of H, halogen, CF₃, —OH, —NH₂, —SH, —SCH₃, —CN, —NO₂, —CH₂(NH₂), —C(O)OH, —S(O)₂NH₂, —C(O)NH₂, —C(O)CH₃, NHC(O)—$C_{1-6}$ alkyl, N($C_{1-3}$ alkyl)C(O)—$C_{1-6}$ alkyl, OC(O)NH₂, OC(O)NH(CH₃), OC(O)N(CH₃)₂, imidazolyl, pyrazolyl, methylimidazolyl, methylpyrazolyl, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 5-10 membered heterocycle, optionally substituted aryl, and optionally substituted 5-10 membered heteroaryl;

wherein the optional substituents for $R_a$, $R_b$, $R_c$, $R_d$, $R_e$, $R_f$, $R_g$, and $R_h$ are 1-3 substituents independently selected from the group consisting of halogen, OH, NH₂, CH₃, CF₃, —CN, —NO₂, —C(O)OH, —S(O)₂NH₂, —C(O)NH₂, —CH₂NH₂, —C(O)CH₃, SH, —S—CH₃, optionally substituted $C_{1-3}$ alkyl, and optionally substituted $C_{3-6}$ cycloalkyl, and wherein the $C_{1-3}$ alkyl and $C_{3-6}$ cycloalkyl optional substituents are 1-2 substituents independently selected from the group consisting of halogen, OH, NH₂, CH₃, CF₃, —CN, —NO₂, —C(O)OH, —S(O)₂NH₂, —C(O)NH₂, —CH₂NH₂, —C(O)CH₃, SH, and —S—CH₃.

In some embodiments, R₃ at each occurrence is independently selected from the group consisting of H, halogen, CF₃, —OH, —NH₂, —SH, —SCH₃, —CN, —NO₂, —CH₂(NH₂), —C(O)OH, —S(O)₂NH₂, —C(O)NH₂, —C(O)CH₃, NHC(O)—$C_{1-6}$ alkyl, N($C_{1-3}$ alkyl)C(O)—$C_{1-6}$ alkyl, OC(O)NH₂, OC(O)NH(CH₃), OC(O)N(CH₃)₂, imidazolyl, pyrazolyl, methylimidazolyl, methylpyrazolyl, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 5-10 membered heterocycle, optionally substituted aryl, and optionally substituted 5-10 membered heteroaryl, wherein the optional substituents for $R_3$ are 1-3 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, —S—$CH_3$, optionally substituted $C_{1-3}$ alkyl, and optionally substituted $C_{3-6}$ cycloalkyl, and wherein the $C_{1-3}$ alkyl and $C_{3-6}$ cycloalkyl optional substituents are 1-2 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, and —S—$CH_3$.

$R_4$ at each occurrence is independently selected from the group consisting of:

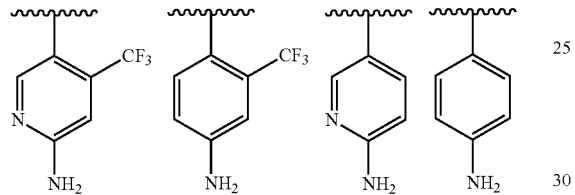

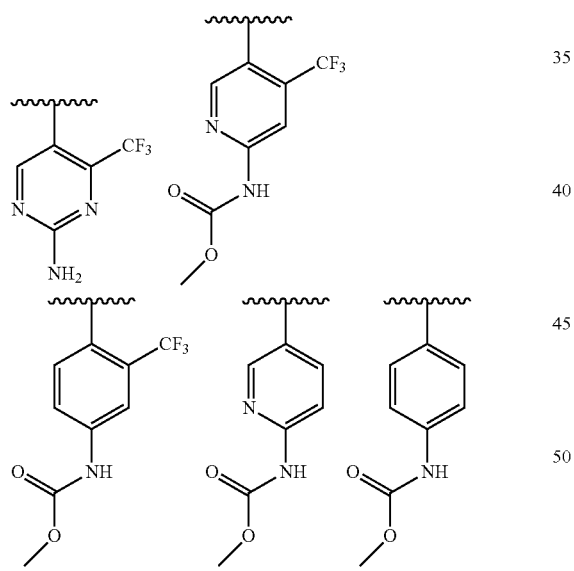

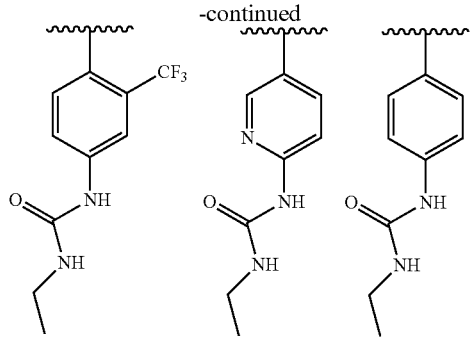

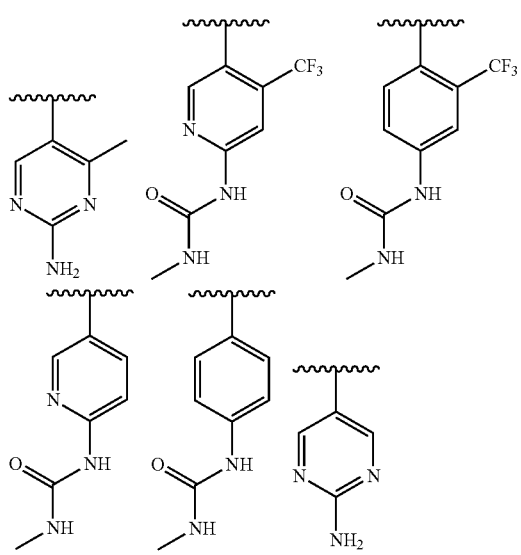

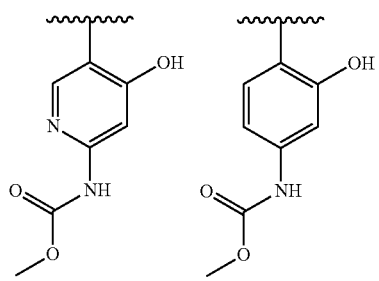

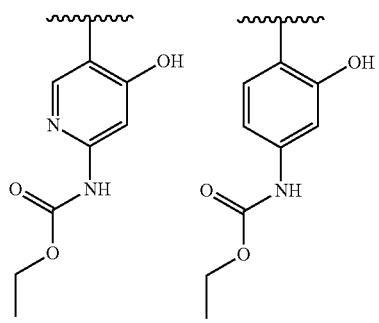

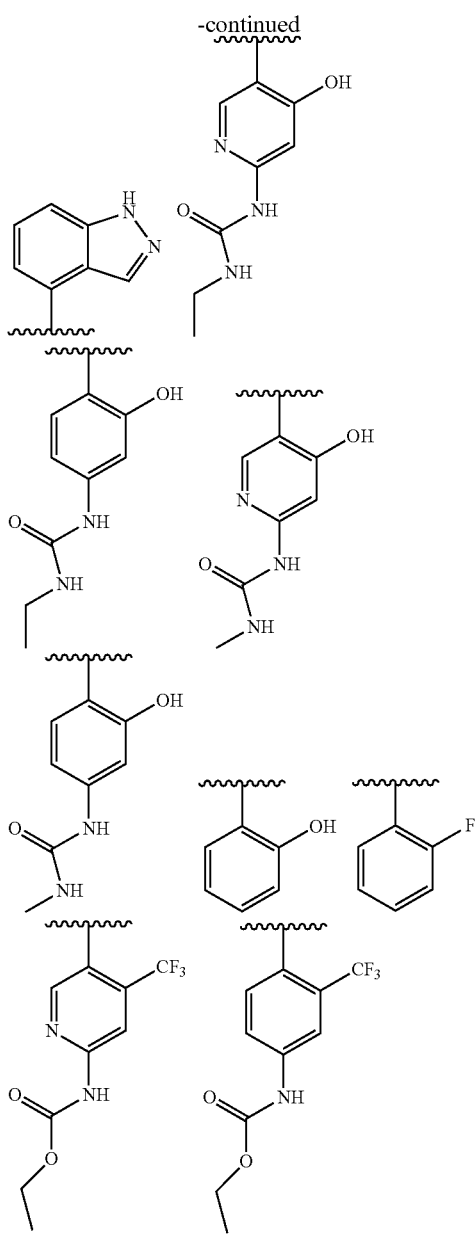

In some embodiments, $R_4$ at each occurrence is independently selected from the group consisting of H, halogen, $CF_3$, —OH, —$NH_2$, —SH, —$SCH_3$, —CN, —$NO_2$, —$CH_2$($NH_2$), —C(O)OH, —S(O)$_2NH_2$, —C(O)$NH_2$, —C(O)$CH_3$, NHC(O)—$C_{1-6}$ alkyl, N($C_{1-3}$ alkyl)C(O)—$C_{1-6}$ alkyl, OC(O)$NH_2$, OC(O)NH($CH_3$), OC(O)N($CH_3$)$_2$, imidazolyl, pyrazolyl, methylimidazolyl, methylpyrazolyl, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 5-10 membered heterocycle, optionally substituted aryl, and optionally substituted 5-10 membered heteroaryl, wherein the optional substituents for $R_4$ are 1-3 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, —S—$CH_3$, optionally substituted $C_{1-3}$ alkyl, and optionally substituted $C_{3-6}$ cycloalkyl, wherein the $C_{1-3}$ alkyl and $C_{3-6}$ cycloalkyl optional substituents are 1-2 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, and —S—$CH_3$.

$R_5$ at each occurrence is independently selected from the group consisting of H, halogen, $CF_3$, —OH, —$NH_2$, —SH, —$SCH_3$, —CN, —$NO_2$, —$CH_2$($NH_2$), —C(O)OH, —S(O)$_2NH_2$, —C(O)$NH_2$, —C(O)$CH_3$, NHC(O)—$C_{1-6}$ alkyl, N($C_{1-3}$ alkyl)C(O)—$C_{1-6}$ alkyl, OC(O)$NH_2$, OC(O)NH($CH_3$), OC(O)N($CH_3$)$_2$, imidazolyl, pyrazolyl, methylimidazolyl, methylpyrazolyl, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 5-10 membered heterocycle, optionally substituted aryl, and optionally substituted 5-10 membered heteroaryl, wherein the optional substituents for $R_5$ are 1-3 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, —S—$CH_3$, optionally substituted $C_{1-3}$ alkyl, and optionally substituted $C_{3-6}$ cycloalkyl, wherein the $C_{1-3}$ alkyl and $C_{3-6}$ cycloalkyl optional substituents are 1-2 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, and —S—$CH_3$.

$R_6$ at each occurrence is independently selected from the group consisting of H, halogen, $CF_3$, —OH, —$NH_2$, —SH, —$SCH_3$, —CN, —$NO_2$, —$CH_2$($NH_2$), —C(O)OH, —S(O)$_2NH_2$, —C(O)$NH_2$, —C(O)$CH_3$, NHC(O)—$C_{1-6}$ alkyl, N($C_{1-3}$ alkyl)C(O)—$C_{1-6}$ alkyl, OC(O)$NH_2$, OC(O)NH($CH_3$), OC(O)N($CH_3$)$_2$, imidazolyl, pyrazolyl, methylimidazolyl, methylpyrazolyl, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 5-10 membered heterocycle, optionally substituted aryl, and optionally substituted 5-10 membered heteroaryl, wherein the optional substituents for $R_6$ are 1-3 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, —S—$CH_3$, optionally substituted $C_{1-3}$ alkyl, and optionally substituted $C_{3-6}$ cycloalkyl, wherein the $C_{1-3}$ alkyl and $C_{3-6}$ cycloalkyl optional substituents are 1-2 substituents independently selected from the group consisting of halogen, OH, $NH_2$, $CH_3$, $CF_3$, —CN, —$NO_2$, —C(O)OH, —S(O)$_2NH_2$, —C(O)$NH_2$, —$CH_2NH_2$, —C(O)$CH_3$, SH, and —S—$CH_3$.

L at each occurrence is independently selected from the group consisting of:

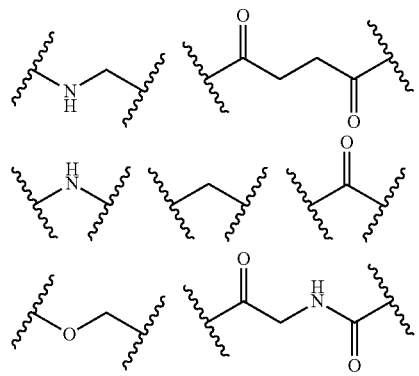

-continued

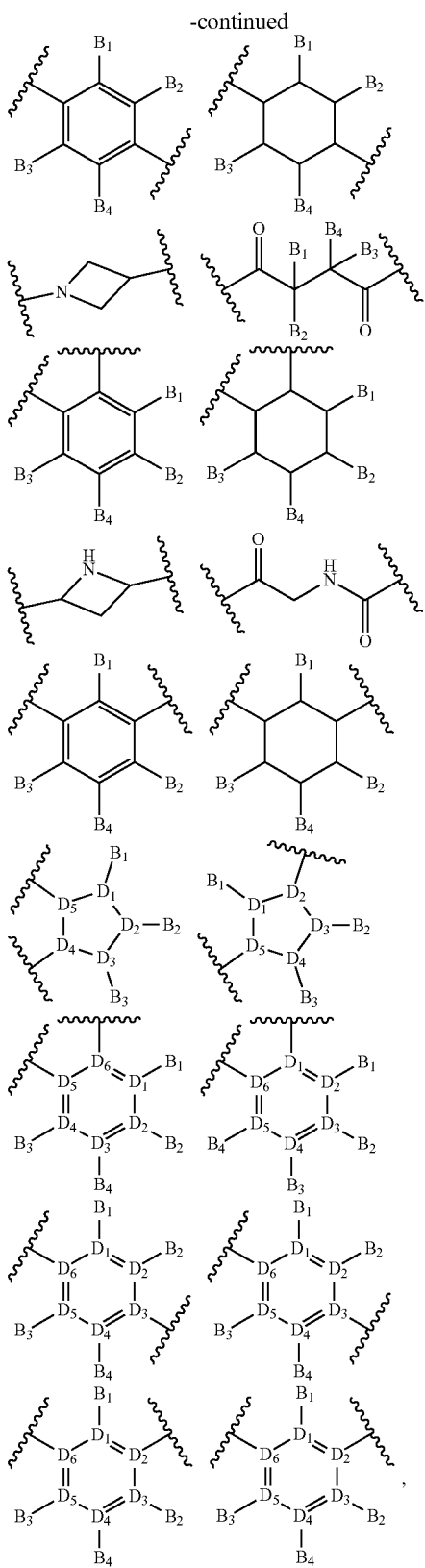

wherein $D_1$, $D_2$, $D_3$, $D_4$, $D_5$, and $D_6$ are at each occurrence are independently selected from the group consisting of N, C, O, or S, provided that if $D_{1-6}$ is a N, the corresponding position is trivalent; if $D_{1-6}$ is a O or S, the corresponding position is divalent. The linker can be attached to the CLM or the functional fragment of the drug on either of the two ends. For example, in

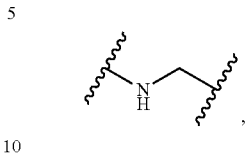

L can be attached to CLM either from the end adjacent to nitrogen or from the other end.

$B_1$, $B_2$, $B_3$, and $B_4$ are at each occurrence absent or independently selected from the group consisting of H, halogen, $CF_3$, —OH, —$NH_2$, —SH, —$SCH_3$, —CN, —$NO_2$, —$CH_2(NH_2)$, —C(O)OH, —$S(O)_2NH_2$, —C(O)$NH_2$, —C(O)$CH_3$, NHC(O)—$C_{1-6}$ alkyl, N($C_{1-3}$ alkyl)C(O)—$C_{1-6}$ alkyl, OC(O)$NH_2$, OC(O)NH($CH_3$), OC(O)N($CH_3$)$_2$, imidazolyl, pyrazolyl, methylimidazolyl, methylpyrazolyl, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 5-10 membered heterocycle, optionally substituted aryl, and optionally substituted 5-10 membered heteroaryl,
   wherein the optional substituents for $B_1$, $B_2$, $B_3$, and $B_4$ are 1-3 substituents independently selected from the group consisting of halogen, OH, $NH_2$, $CH_3$, $CF_3$, —CN, —$NO_2$, —C(O)OH, —$S(O)_2NH_2$, —C(O)$NH_2$, —$CH_2NH_2$, —C(O)$CH_3$, SH, —S—$CH_3$, optionally substituted $C_{1-3}$ alkyl, and optionally substituted $C_{3-6}$ cycloalkyl,
   wherein the $C_{1-3}$ alkyl and $C_{3-6}$ cycloalkyl optional substituents are 1-2 substituents independently selected from the group consisting of halogen, OH, $NH_2$, $CH_3$, $CF_3$, —CN, —$NO_2$, —C(O)OH, —$S(O)_2NH_2$, —C(O)$NH_2$, —$CH_2NH_2$, —C(O)$CH_3$, SH, and —S—$CH_3$.

In some embodiments, L at each occurrence is independently selected from the group consisting of unsubstituted or substituted -(alk)$_a$-S-(alk)$_b$-, -(alk)$_a$-O-(alk)$_b$-, -(alk)$_a$-NR$^C$-(alk)$_b$-, -(alk)$_a$-C(O)-(alk)$_b$-, -(alk)$_a$-C(S)-(alk)$_b$-, -(alk)$_a$-S(O)-(alk)$_b$-, -(alk)$_a$-S(O)$_2$-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)NR$^C$-(alk)$_b$-, -(alk)$_a$-C(S)NR$^C$-(alk)$_b$-, -(alk)$_a$-S(O)$_2$NR$^C$-(alk)$_b$-, -(alk)$_a$-NR$^C$C(O)-(alk)$_b$-, -(alk)$_a$-NR$^C$C(S)-(alk)$_b$-, -(alk)$_a$-NR$^C$S(O)$_2$-(alk)$_b$-, -(alk)$_a$-NR$^C$C(O)O-(alk)$_b$-, -(alk)$_a$-NR$^C$C(S)O-(alk)$_b$-, -(alk)$_a$-OC(O)NR$^C$-(alk)$_b$-, -(alk)$_a$-OC(S)NR$^C$-(alk)$_b$-, -(alk)$_a$-NR$^C$C(O)NR$^D$-(alk)$_b$-, -(alk)$_a$-NR$^C$C(S)NR$^D$-(alk)$_b$-, and -(alk)$_a$-NR$^C$S(O)$_2$NR$^D$-(alk)$_b$-;
   a and b are independently selected from the group consisting of 0, 1, 2, 3, and 4;
   alk is independently selected from the group consisting of $C_{1-5}$ alkylene, $C_{1-5}$ alkenylene, and $C_{1-5}$ alkynylene, each of which is optionally substituted with 1-3 substituents independently selected from the group consisting of H, halogen, —OH, $NH_2$, $CF_3$, $C_{1-5}$ alkyl, —$CH_2(NH_2)$, —CN, —$NO_2$, —C(O)OH, —$S(O)_2NH_2$, —C(O)$NH_2$, —C(O)$CH_3$, —SH, imidazolyl, pyrazolyl, methylimidazolyl, methylpyrazolyl, —O—$C_{1-5}$ alkyl, —S—$C_{1-5}$ alkyl, —NH—$C_{1-5}$ alkyl, and —N($C_{1-5}$ alkyl)$_2$, wherein the $C_{1-5}$ alkyl groups are independently optionally substituted with 1-3 groups selected from the group consisting of halogen, —OH, —$NH_2$, $C_{1-4}$ alkyl, $CF_3$, —$CH_2(NH_2)$, —CN, —$NO_2$, —C(O)OH, —$S(O)_2NH_2$, —C(O)$NH_2$, —C(O)$CH_3$, —SH, —SCH₃, imidazolyl, pyrazolyl, methylimidazolyl, and methylpyrazolyl.

$R^C$ and $R^D$, at each occurrence, are independently selected from the group consisting of hydrogen, $C_{1-3}$ alkyl, $C_{3-6}$ cycloalkyl, 5-10 membered heterocycle, aryl, and 5-10 membered heteroaryl, wherein the alkyl, cycloalkyl, heterocycle, aryl, and heteroaryl are each independently optionally substituted with 1-3 substituents selected from the group consisting of halogen, $C_{1-3}$ alkyl, OH, $NH_2$, NH—$C_{1-3}$ alkyl, N($C_{1-3}$ alkyl)₂, $CF_3$, $C_{1-6}$ alkyl, —$CH_2(NH_2)$, —CN, —$NO_2$, —C(O)OH, —S(O)₂$NH_2$, —C(O)$NH_2$, —C(O)$CH_3$, —SH, —$SCH_3$, imidazolyl, pyrazolyl, methylimidazolyl, and methylpyrazolyl.

X at each occurrence is independently selected from the group consisting of:

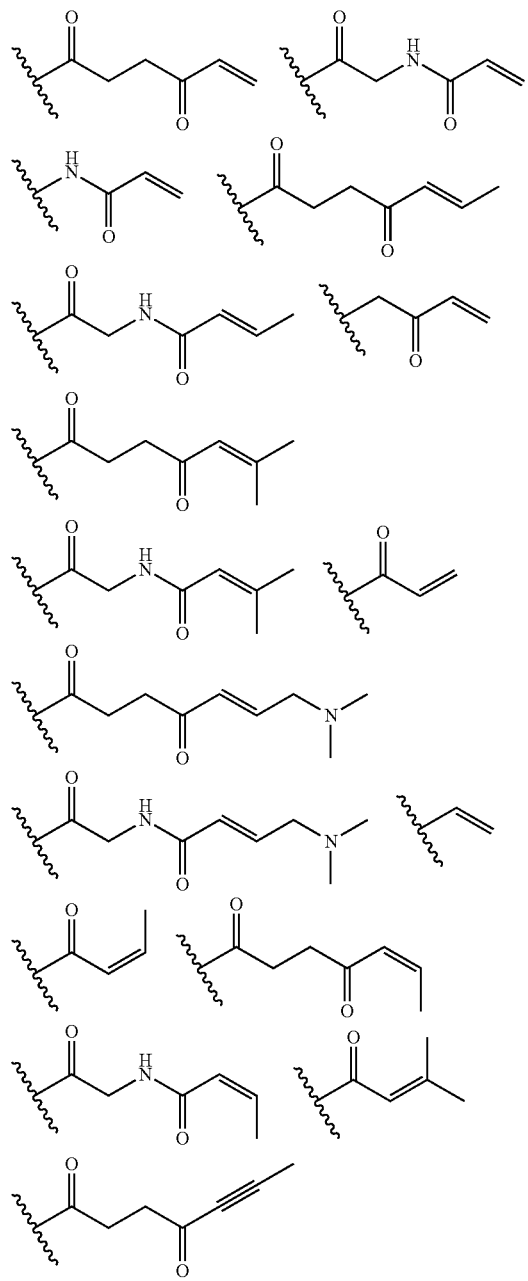
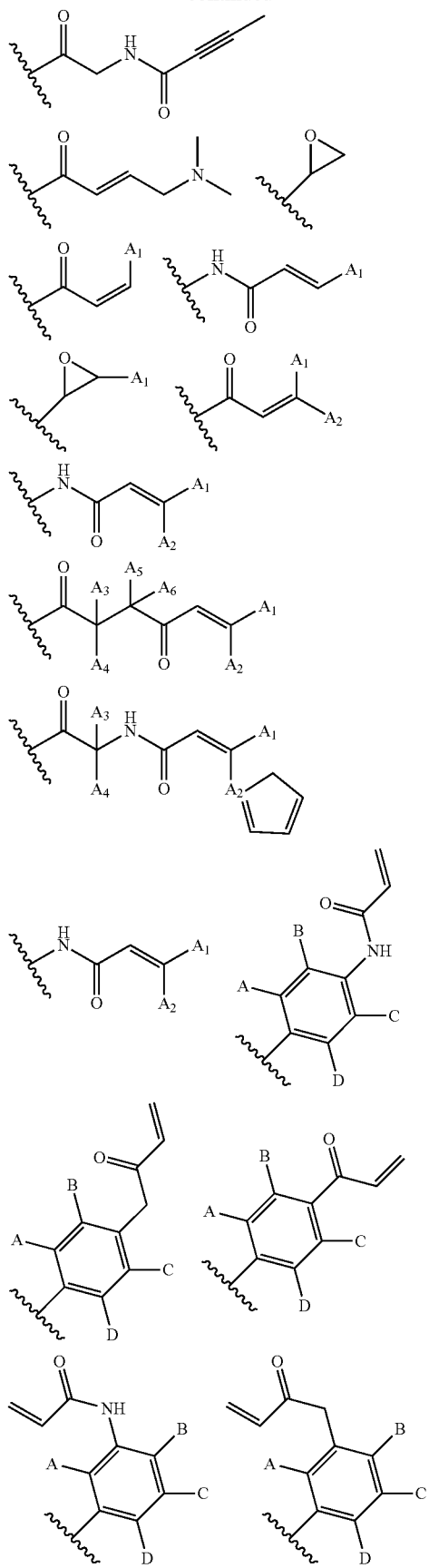

-continued
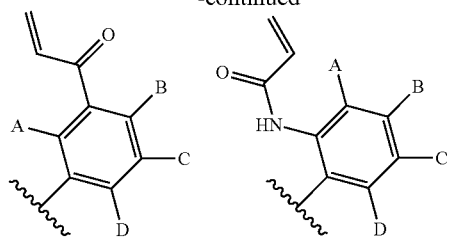
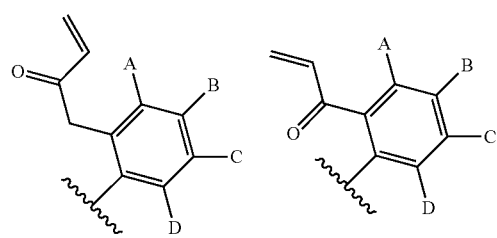
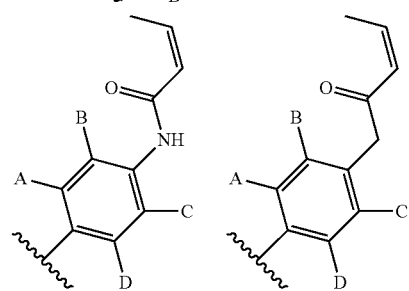
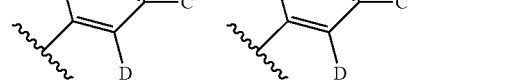
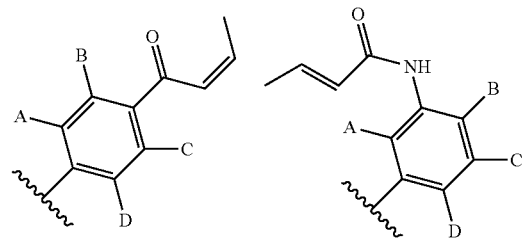
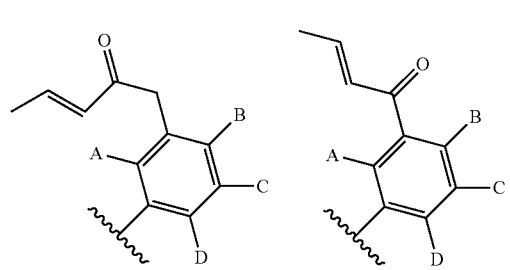
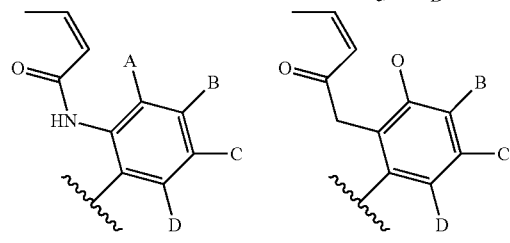
-continued
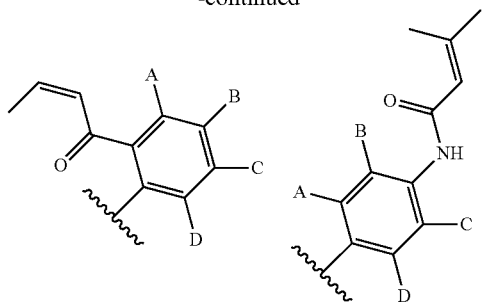
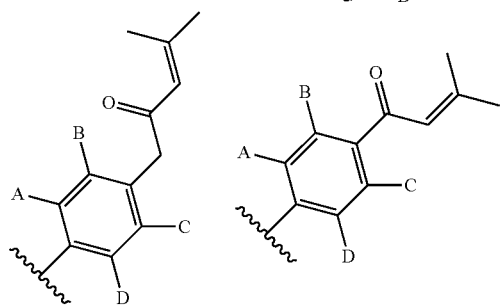
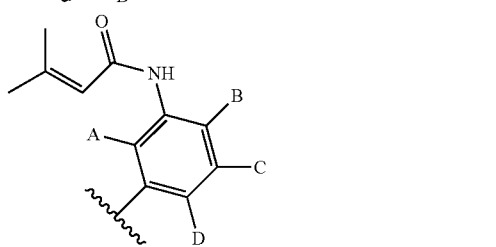
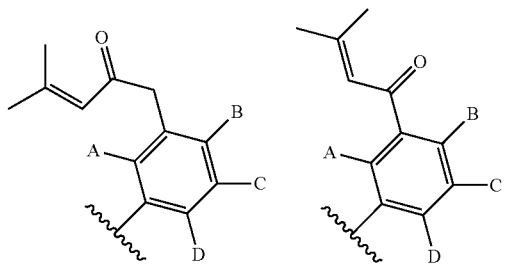
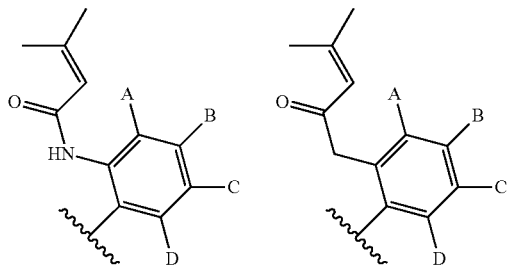
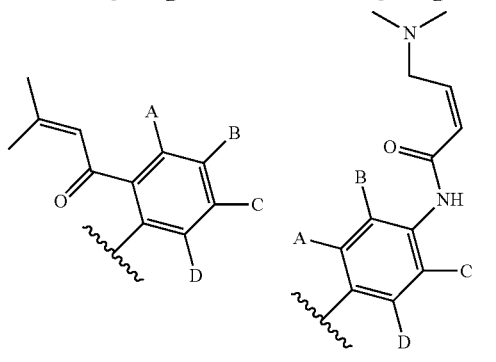

-continued
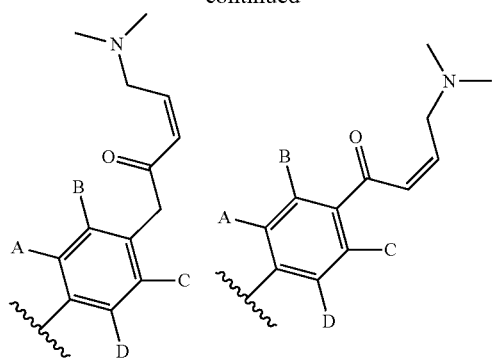
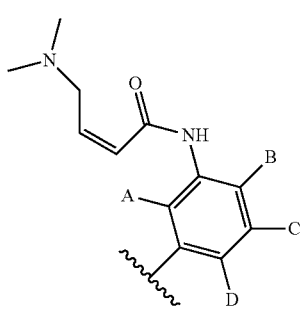
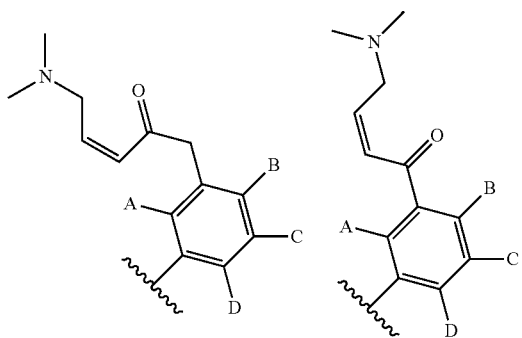
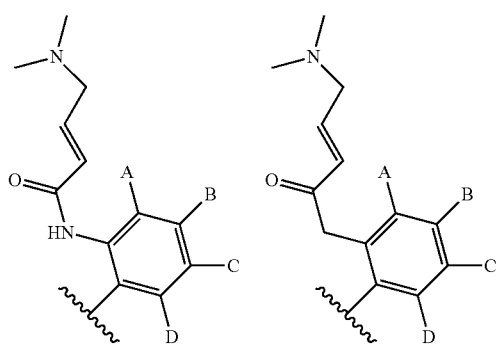
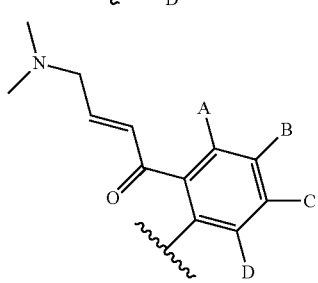
-continued
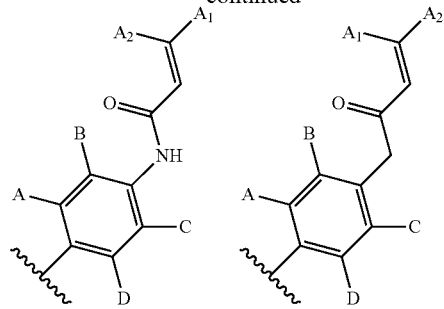
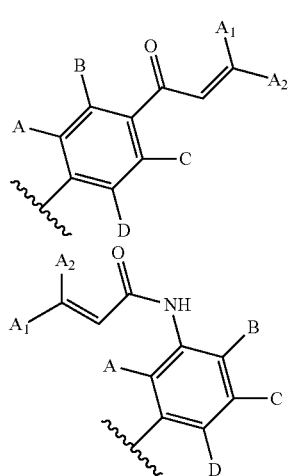
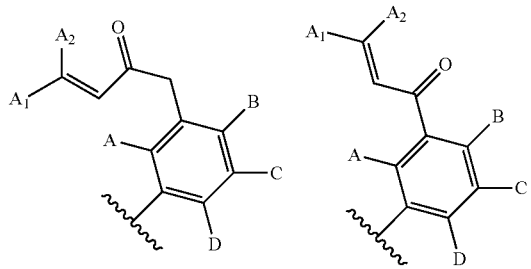
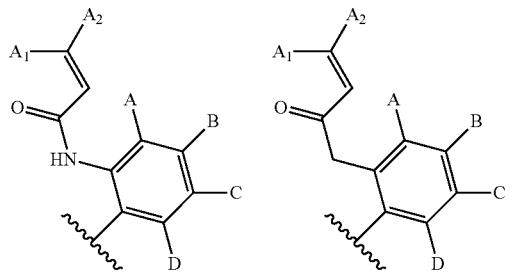
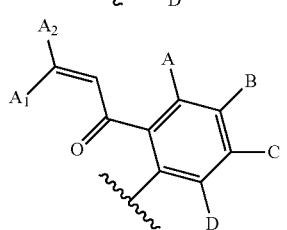

-continued
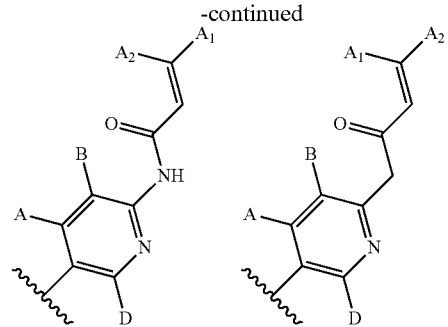
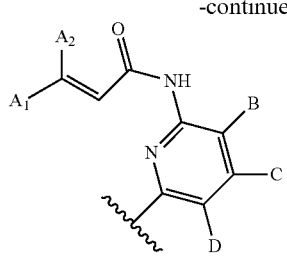
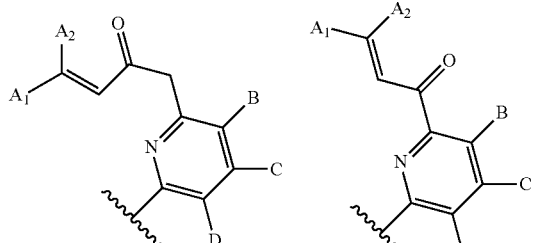
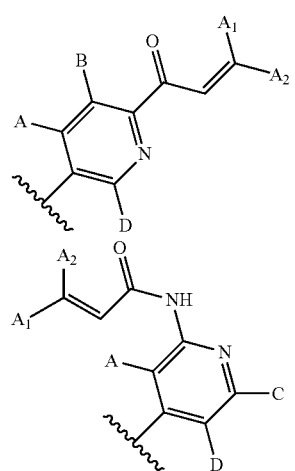
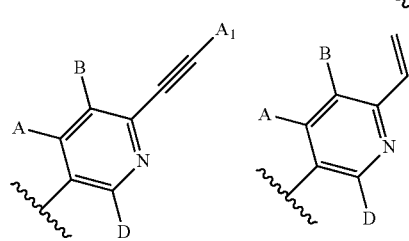
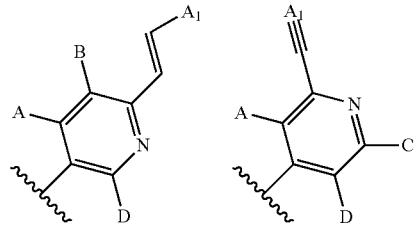
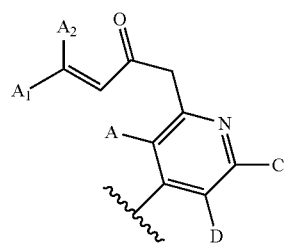
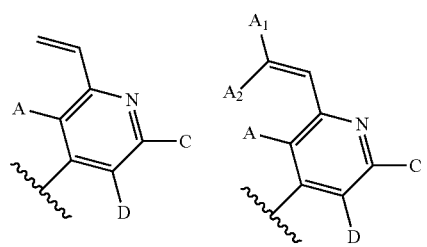
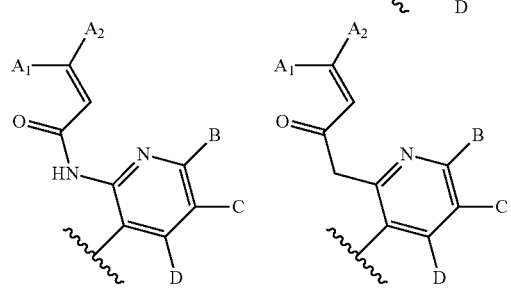
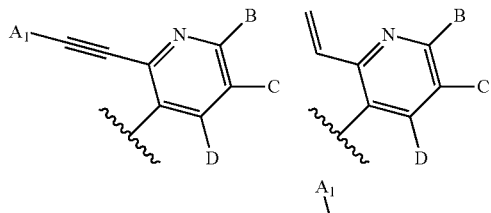
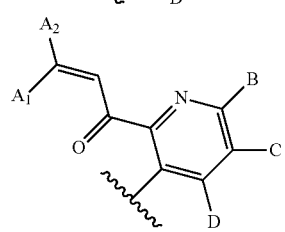
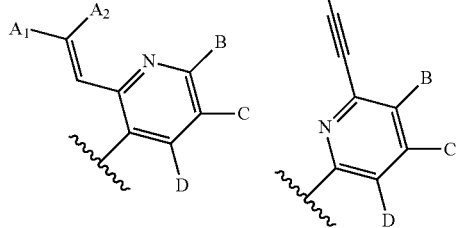

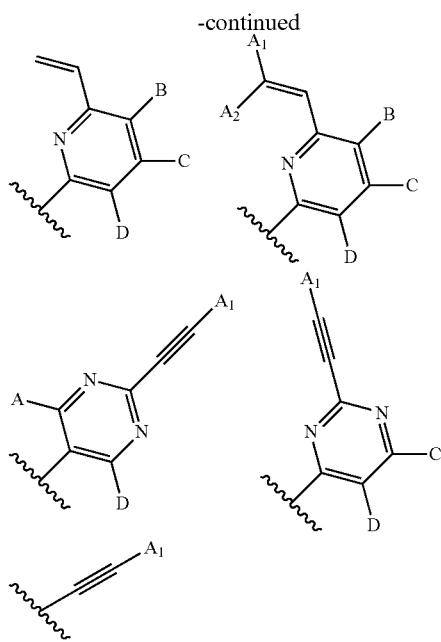

A, B, C, and D at each occurrence are independently selected from the group consisting of H, halogen, CF$_3$, —OH, —NH$_2$, —SH, —SCH$_3$, —CN, —NO$_2$, —CH$_2$(NH$_2$), —C(O)OH, —S(O)$_2$NH$_2$, —C(O)NH$_2$, —C(O)CH$_3$, NHC(O)—C$_{1-6}$ alkyl, N(C$_{1-3}$ alkyl)C(O)—C$_{1-6}$ alkyl, OC(O)NH$_2$, OC(O)NH(CH$_3$), OC(O)N(CH$_3$)$_2$, imidazolyl, pyrazolyl, methylimidazolyl, methylpyrazolyl, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted 5-10 membered heterocycle, optionally substituted aryl, and optionally substituted 5-10 membered heteroaryl, wherein the optional substituents for A, B, C, and D are 1-3 substituents independently selected from the group consisting of halogen, OH, NH$_2$, CH$_3$, CF$_3$, —CN, —NO$_2$, —C(O)OH, —S(O)$_2$NH$_2$, —C(O)NH$_2$, —CH$_2$NH$_2$, —C(O)CH$_3$, SH, —S—CH$_3$, optionally substituted C$_{1-3}$ alkyl, and optionally substituted C$_{3-6}$ cycloalkyl, wherein the C$_{1-3}$ alkyl and C$_{3-6}$ cycloalkyl optional substituents are 1-2 substituents independently selected from the group consisting of halogen, OH, NH$_2$, CH$_3$, CF$_3$, —CN, —NO$_2$, —C(O)OH, —S(O)$_2$NH$_2$, —C(O)NH$_2$, —CH$_2$NH$_2$, —C(O)CH$_3$, SH, and —S—CH$_3$.

A$_1$, A$_2$, A$_3$, A$_4$, A$_5$, and A$_6$ at each occurrence is independently selected from the group consisting of H, halogen, CF$_3$, —OH, —NH$_2$, —SH, —SCH$_3$, —CN, —NO$_2$, —CH$_2$(NH$_2$), —C(O)OH, —S(O)$_2$NH$_2$, —C(O)NH$_2$, —C(O)CH$_3$, NHC(O)—C$_{1-6}$ alkyl, N(C$_{1-3}$ alkyl)C(O)—C$_{1-6}$ alkyl, OC(O)NH$_2$, OC(O)NH(CH$_3$), OC(O)N(CH$_3$)$_2$, imidazolyl, pyrazolyl, methylimidazolyl, methylpyrazolyl, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted 5-10 membered heterocycle, optionally substituted aryl, and optionally substituted 5-10 membered heteroaryl, wherein the optional substituents for A$_1$, A$_2$, A$_3$, A$_4$, A$_5$, and A$_6$ are 1-3 substituents independently selected from the group consisting of halogen, OH, NH$_2$, CH$_3$, CF$_3$, —CN, —NO$_2$, —C(O)OH, —S(O)$_2$NH$_2$, —C(O)NH$_2$, —CH$_2$NH$_2$, —C(O)CH$_3$, SH, —S—CH$_3$, optionally substituted C$_{1-3}$ alkyl, and optionally substituted C$_{3-6}$ cycloalkyl, wherein the C$_{1-3}$ alkyl and C$_{3-6}$ cycloalkyl optional substituents are 1-2 substituents independently selected from the group consisting of halogen, OH, NH$_2$, CH$_3$, CF$_3$, —CN, —NO$_2$, —C(O)OH, —S(O)$_2$NH$_2$, —C(O)NH$_2$, —CH$_2$NH$_2$, —C(O)CH$_3$, SH, and —S—CH$_3$.

The disclosure contemplates using all combinations of the various substituents. Thus, any combination of the above-mentioned substituents falling within the structural formula Compound 1-1 to Compound 1-5 can be used.

In some embodiments, the ARCS are selected from the group consisting of narrow generic structures Compound 1-6 to Compound 1-11, Compound 1-6

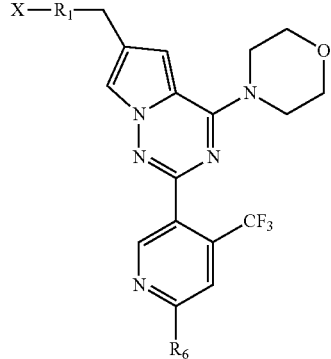

Compound 1-7

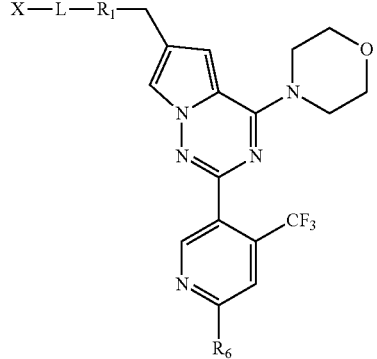

Compound 1-8

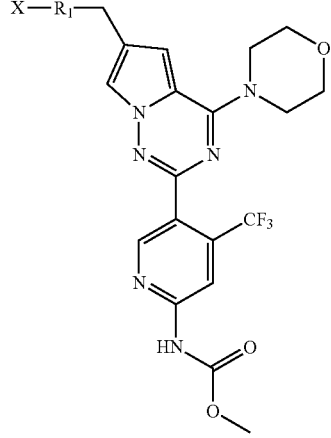

-continued

Compound 1-9

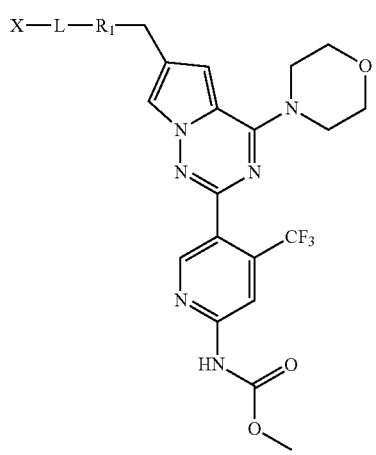

Compound 1-10

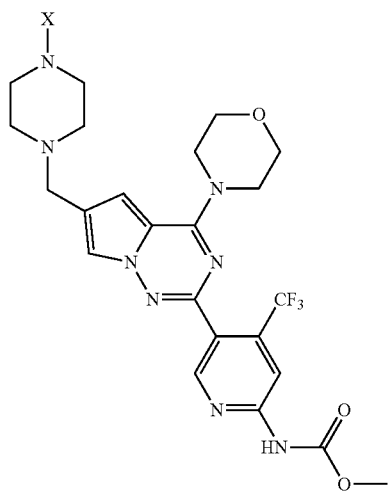

Compound 1-11

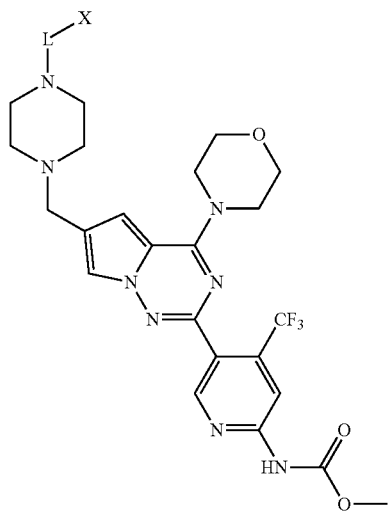

or a pharmaceutically acceptable salt thereof.

In some embodiments, the ARCS may have a structure of

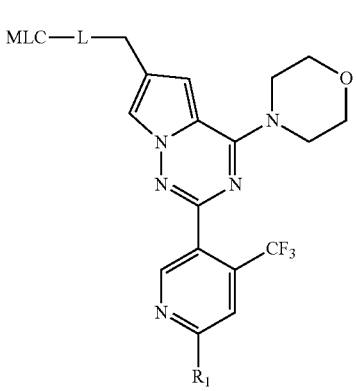

Formula 50 or a pharmaceutically acceptable salt thereof, wherein L is a linker selected from the group consisting of

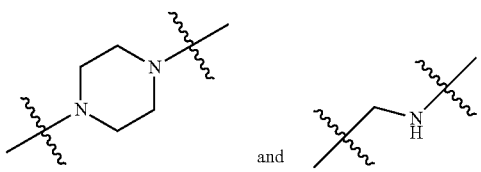

and wherein either end can be connected to the CLM; R1 is selected from the group consisting of

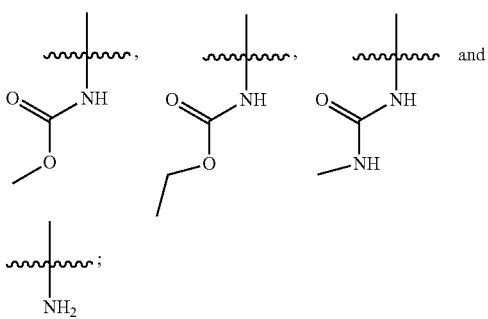

and CLM is selected from the group consisting of

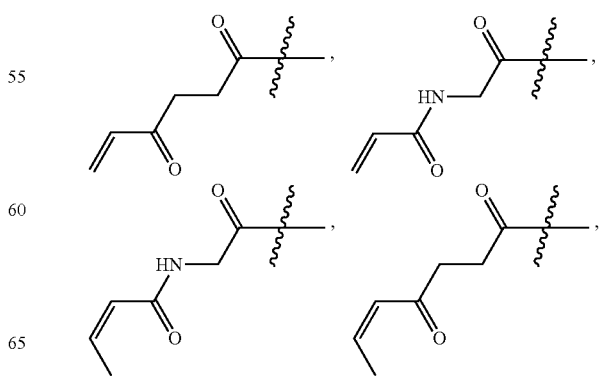

1-130, 1-137, 1-138, 1-145, 1-146, 1-153, 1-154, 1-161, 1-162, 1-169, 1-170, 1-171 and 1-172 in Table 1 below.

In some embodiments, the ARCS may have a structure of

Formula 1-51 or a pharmaceutically acceptable salt thereof, wherein L, the linker is

R2 is selected from the group consisting of and CLM is selected from the group consisting of The compounds encompassed by Formula 1-50 include but not limited to Compound 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129,

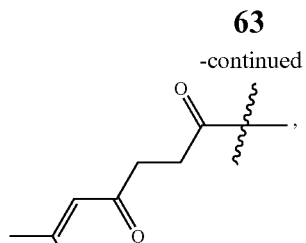
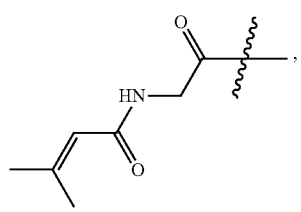
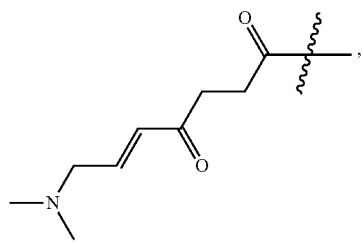
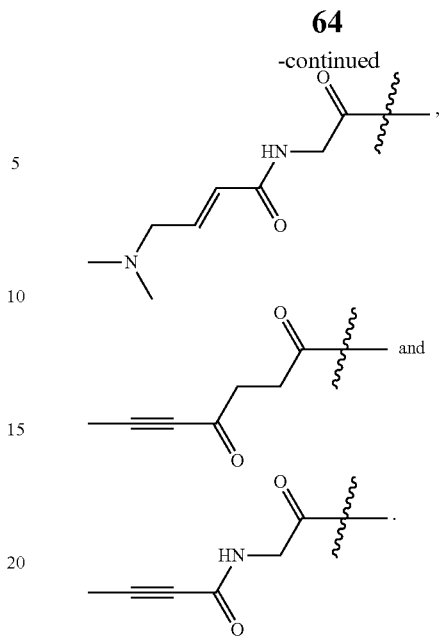
The compounds encompassed by Formula 1-51 include but not limited to Compound 1-131, 1-132, 1-133, 1-134, 1-135, 1-136, 1-139, 1-140, 1-141, 1-142, 1-143, 1-144, 1-147, 1-148, 1-149, 1-150, 1-151, 1-152, 1-155, 1-156, 1-157, 1-158, 1-159, 1-160, 1-163, 1-164, 1-165, 1-166, 1-167 and 1-168 in Table 1 below.
Exemplary ARCS include any compound selected from the group consisting of Compound 1-101 to Compound 1-172.
TABLE 1
Non-limiting Examples of ARCS Compounds
Compound 1-101
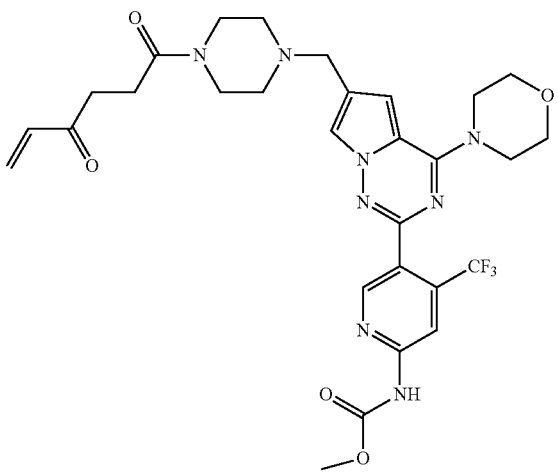 [SMILES: C=CC(=O)CCC(=O)N1CCN(Cc2cc3c(N4CCOCC4)nc(-c4cnc(NC(=O)OC)cc4C(F)(F)F)nn3c2)CC1]

TABLE 1-continued
Non-limiting Examples of ARCS Compounds
Compound 1-102
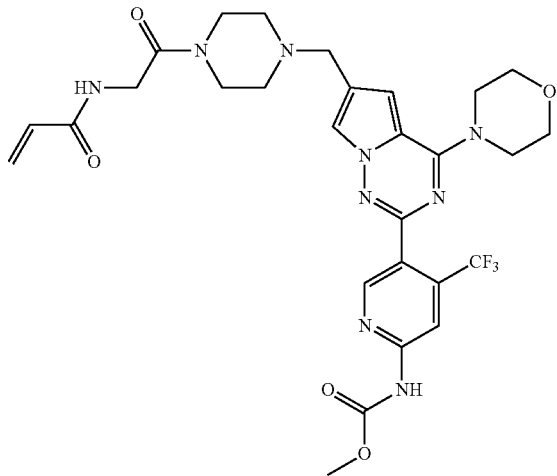 [SMILES: C=CC(=O)NCC(=O)N1CCN(Cc2cc3c(N4CCOCC4)nc(-c4cnc(NC(=O)OC)cc4C(F)(F)F)nn3c2)CC1]
Compound 1-103
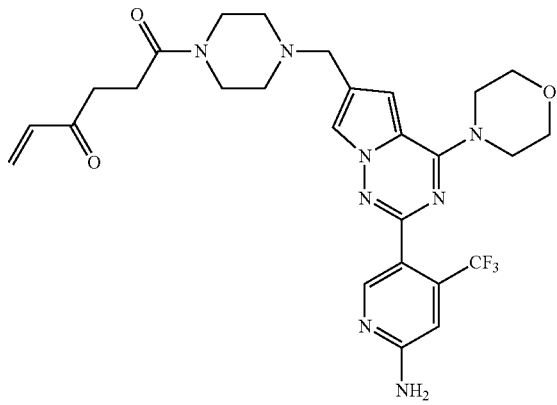 [SMILES: C=CC(=O)CCC(=O)N1CCN(Cc2cc3c(N4CCOCC4)nc(-c4cnc(N)cc4C(F)(F)F)nn3c2)CC1]
Compound 1-104
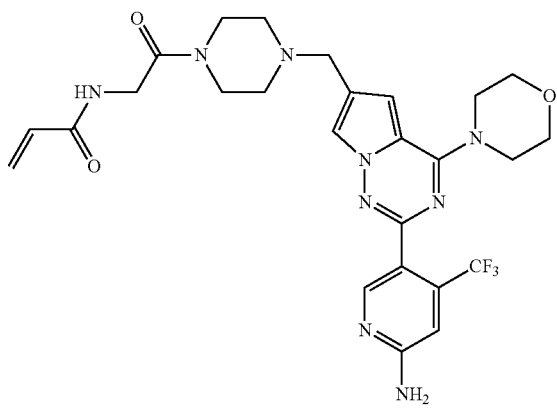 [SMILES: C=CC(=O)NCC(=O)N1CCN(Cc2cc3c(N4CCOCC4)nc(-c4cnc(N)cc4C(F)(F)F)nn3c2)CC1]

TABLE 1-continued
Non-limiting Examples of ARCS Compounds
Compound 1-105
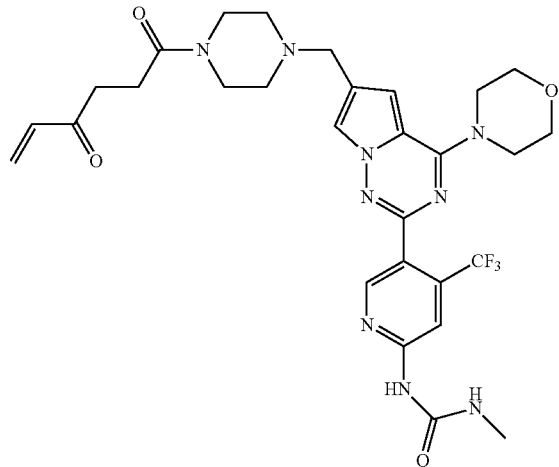 [SMILES: C=CC(=O)CCC(=O)N1CCN(Cc2cc3c(N4CCOCC4)nc(-c4cnc(NC(=O)NC)cc4C(F)(F)F)nn3c2)CC1]
Compound 1-106
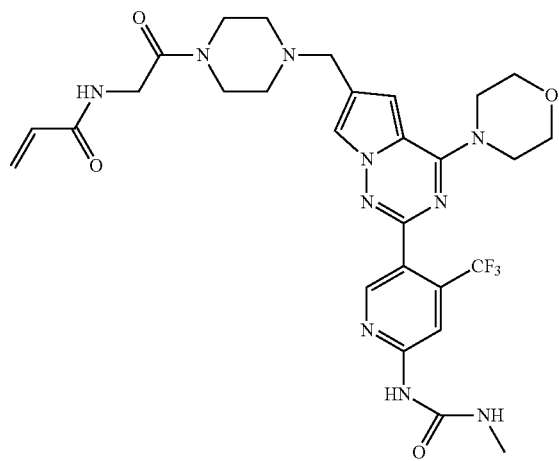 [SMILES: C=CC(=O)NCC(=O)N1CCN(Cc2cc3c(N4CCOCC4)nc(-c4cnc(NC(=O)NC)cc4C(F)(F)F)nn3c2)CC1]
Compound 1-107
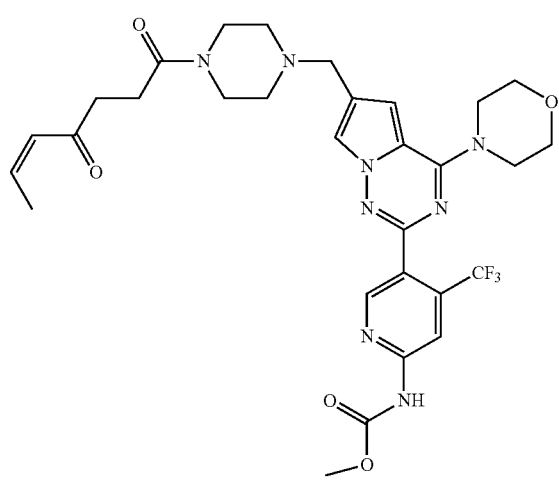

TABLE 1-continued
Non-limiting Examples of ARCS Compounds
Compound 1-108
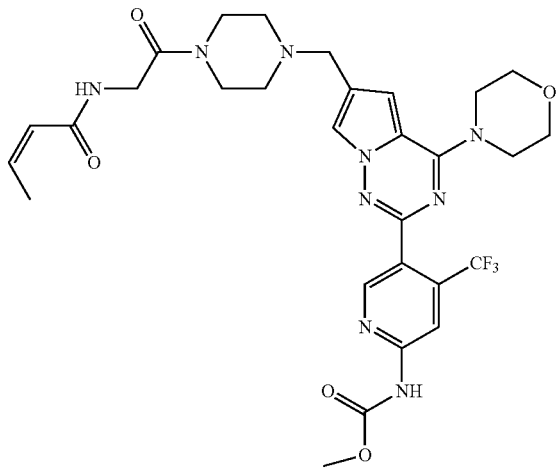 [SMILES: C/C=C\C(=O)NCC(=O)N1CCN(Cc2cc3c(N4CCOCC4)nc(-c4cnc(NC(=O)OC)cc4C(F)(F)F)nn3c2)CC1]
Compound 1-109
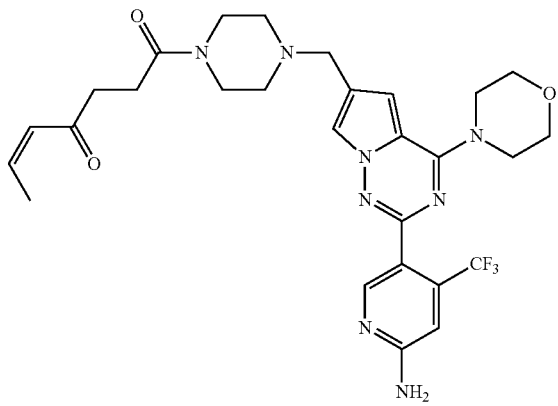 [SMILES: C/C=C\C(=O)CCC(=O)N1CCN(Cc2cc3c(N4CCOCC4)nc(-c4cnc(N)cc4C(F)(F)F)nn3c2)CC1]
Compound 1-110
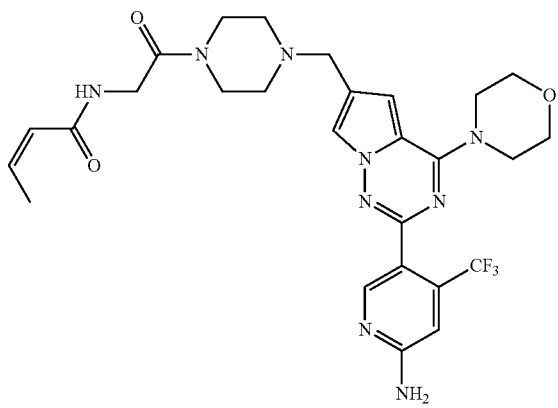 [SMILES: C/C=C\C(=O)NCC(=O)N1CCN(Cc2cc3c(N4CCOCC4)nc(-c4cnc(N)cc4C(F)(F)F)nn3c2)CC1]

TABLE 1-continued
Non-limiting Examples of ARCS Compounds
Compound 1-111
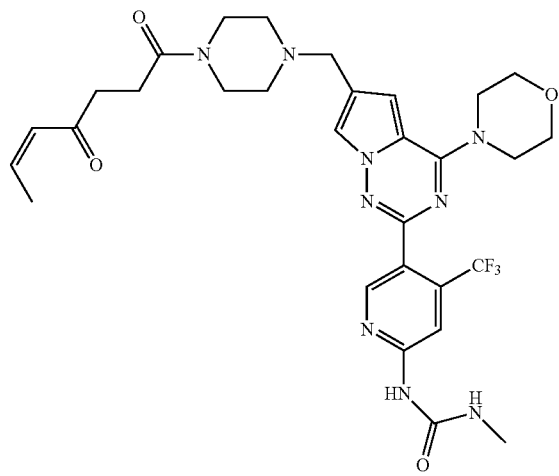 [SMILES: C/C=C\C(=O)CCC(=O)N1CCN(Cc2cc3c(N4CCOCC4)nc(-c4cnc(NC(=O)NC)cc4C(F)(F)F)nn3c2)CC1]
Compound 1-112
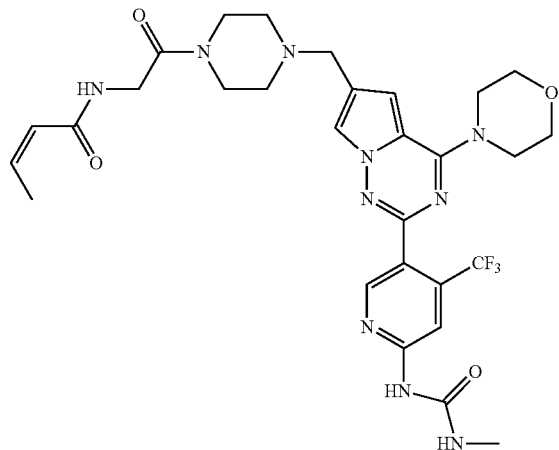 [SMILES: C/C=C\C(=O)NCC(=O)N1CCN(Cc2cc3c(N4CCOCC4)nc(-c4cnc(NC(=O)NC)cc4C(F)(F)F)nn3c2)CC1]
Compound 1-113
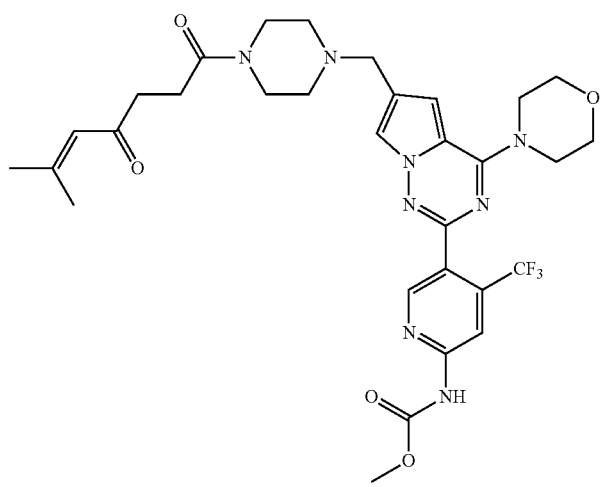 [SMILES: COC(=O)Nc1cc(C(F)(F)F)c(-c2nc(N3CCOCC3)c3cc(CN4CCN(C(=O)CCC(=O)C=C(C)C)CC4)cn3n2)cn1]

TABLE 1-continued
Non-limiting Examples of ARCS Compounds
Compound 1-114
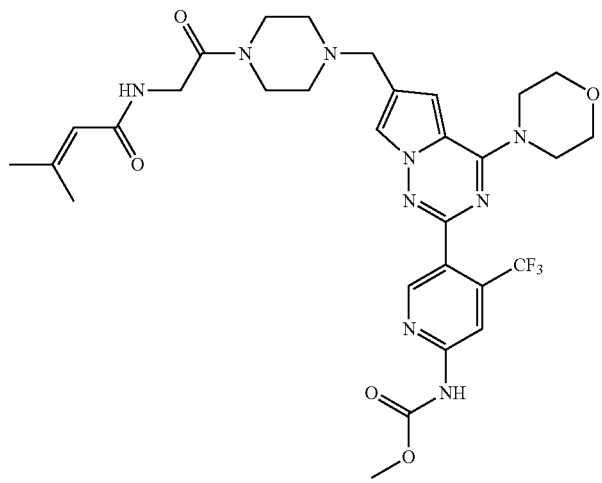 [SMILES: COC(=O)Nc1cc(C(F)(F)F)c(-c2nc(N3CCOCC3)c3cc(CN4CCN(C(=O)CNC(=O)C=C(C)C)CC4)cn3n2)cn1]
Compound 115
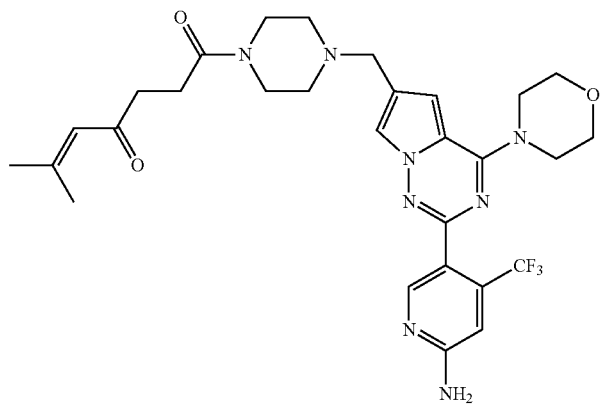 [SMILES: CC(C)=CC(=O)CCC(=O)N1CCN(Cc2cc3c(N4CCOCC4)nc(-c4cnc(N)cc4C(F)(F)F)nn3c2)CC1]
Compound 1-116
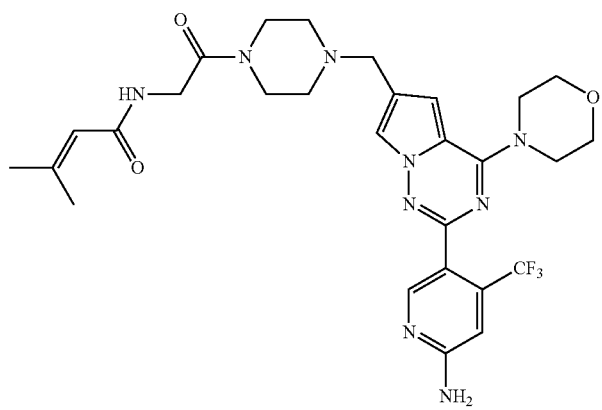 [SMILES: CC(C)=CC(=O)NCC(=O)N1CCN(Cc2cc3c(N4CCOCC4)nc(-c4cnc(N)cc4C(F)(F)F)nn3c2)CC1]

TABLE 1-continued
Non-limiting Examples of ARCS Compounds
Compound 1-117
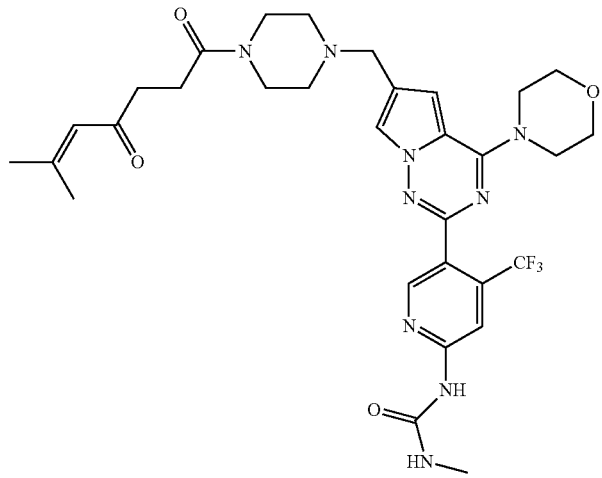 [SMILES: CNC(=O)Nc1cc(C(F)(F)F)c(-c2nc(N3CCOCC3)c3cc(CN4CCN(C(=O)CCC(=O)C=C(C)C)CC4)cn3n2)cn1]
Compound 1-118
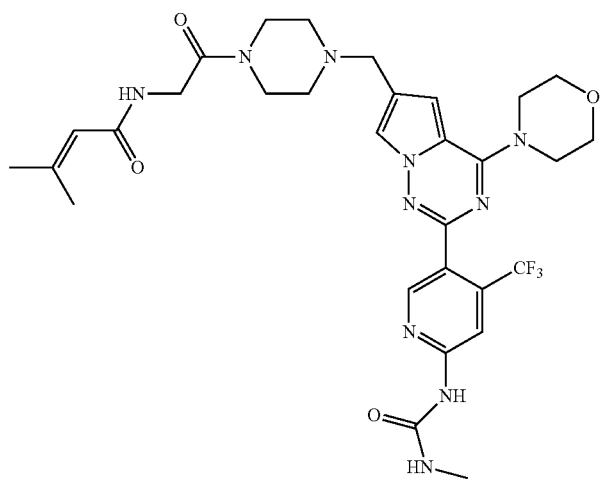 [SMILES: CNC(=O)Nc1cc(C(F)(F)F)c(-c2nc(N3CCOCC3)c3cc(CN4CCN(C(=O)CNC(=O)C=C(C)C)CC4)cn3n2)cn1]
Compound 1-119
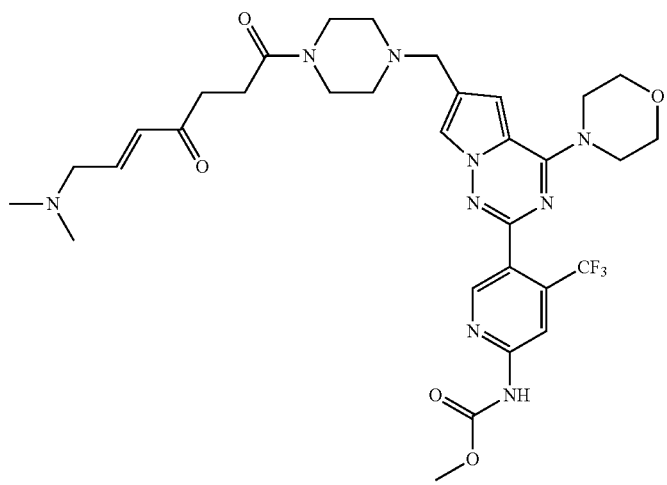 [SMILES: COC(=O)Nc1cc(C(F)(F)F)c(-c2nc(N3CCOCC3)c3cc(CN4CCN(C(=O)CCC(=O)/C=C/CN(C)C)CC4)cn3n2)cn1]

TABLE 1-continued
Non-limiting Examples of ARCS Compounds
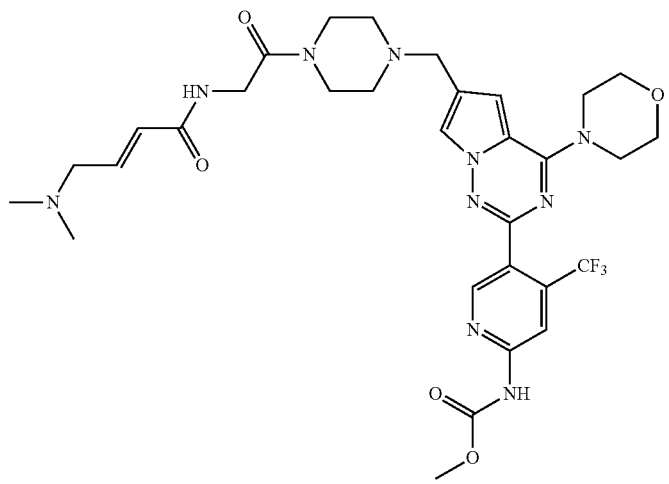 [SMILES: COC(=O)Nc1cc(C(F)(F)F)c(-c2nc(N3CCOCC3)c3cc(CN4CCN(C(=O)CNC(=O)/C=C/CN(C)C)CC4)cn3n2)cn1]
Compound 1-120
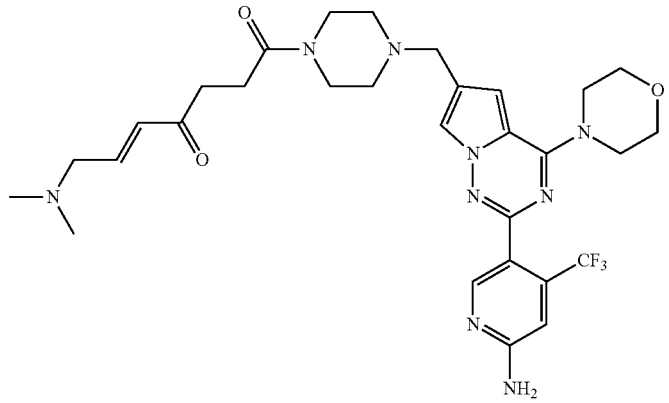 [SMILES: CN(C)C/C=C/C(=O)CCC(=O)N1CCN(Cc2cc3c(N4CCOCC4)nc(-c4cnc(N)cc4C(F)(F)F)nn3c2)CC1]
Compound 1-121
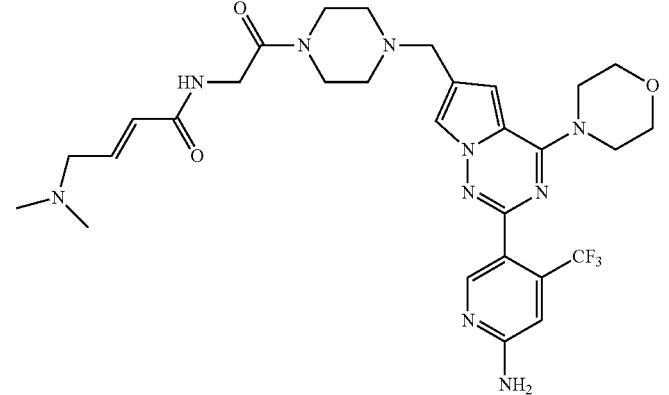 [SMILES: CN(C)C/C=C/C(=O)NCC(=O)N1CCN(Cc2cc3c(N4CCOCC4)nc(-c4cnc(N)cc4C(F)(F)F)nn3c2)CC1]
Compound 1-122

TABLE 1-continued
Non-limiting Examples of ARCS Compounds
Compound 1-123
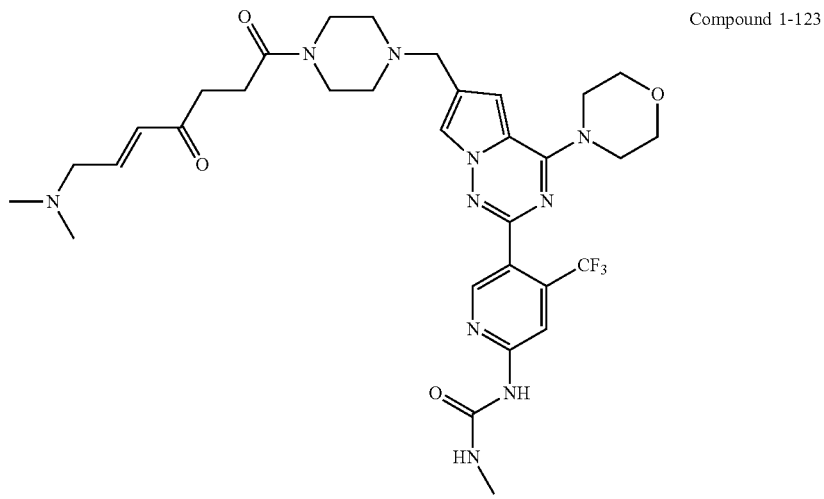
Compound 1-124
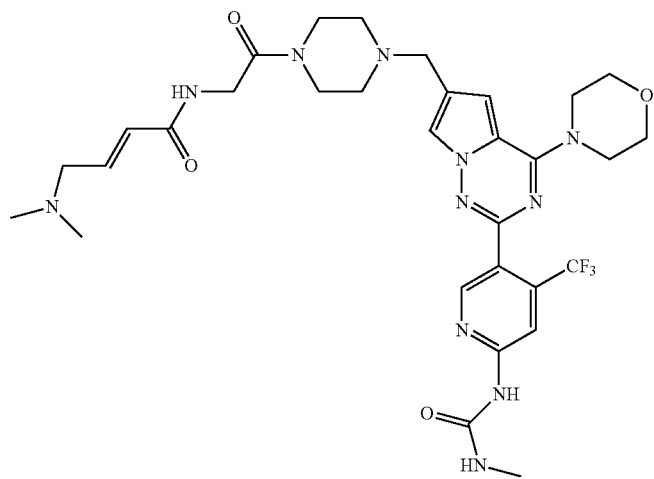 [SMILES: CNC(=O)Nc1cc(C(F)(F)F)c(-c2nc(N3CCOCC3)c3cc(CN4CCN(C(=O)CNC(=O)/C=C/CN(C)C)CC4)cn3n2)cn1]
Compound 1-125
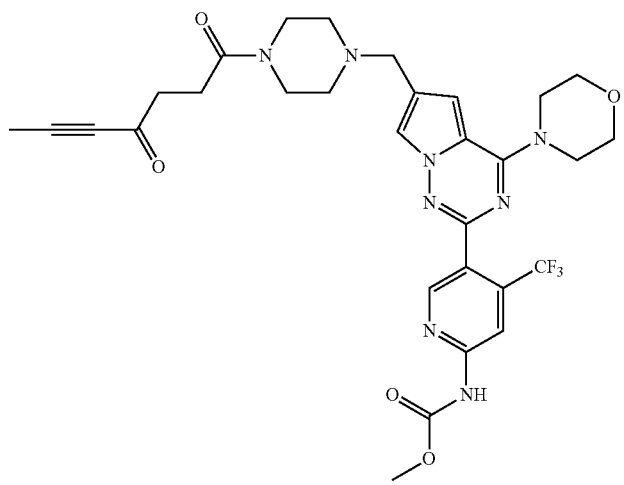

TABLE 1-continued
Non-limiting Examples of ARCS Compounds
Compound 1-126
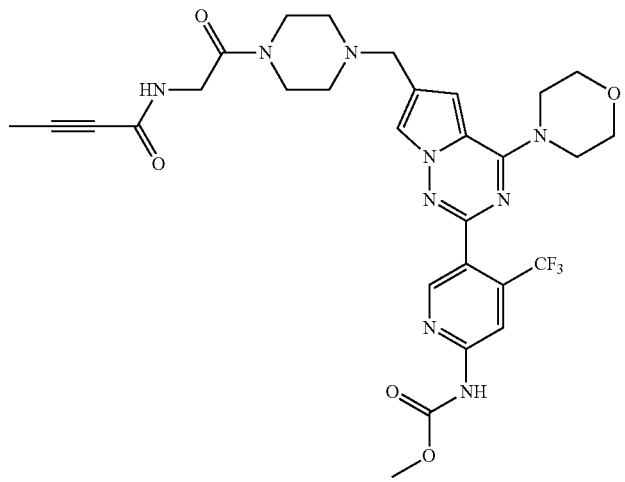 [SMILES: CC#CC(=O)CCC(=O)N1CCN(Cc2cc3c(N4CCOCC4)nc(-c4cnc(NC(=O)OC)cc4C(F)(F)F)nn3c2)CC1]
Compound 1-127
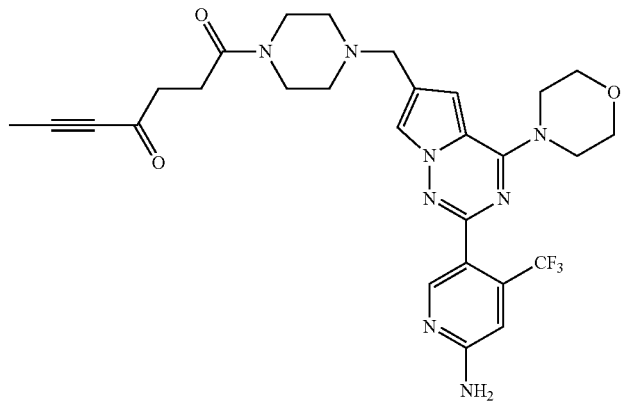 [SMILES: CC#CC(=O)CCC(=O)N1CCN(Cc2cc3c(N4CCOCC4)nc(-c4cnc(N)cc4C(F)(F)F)nn3c2)CC1]
Compound 1-128
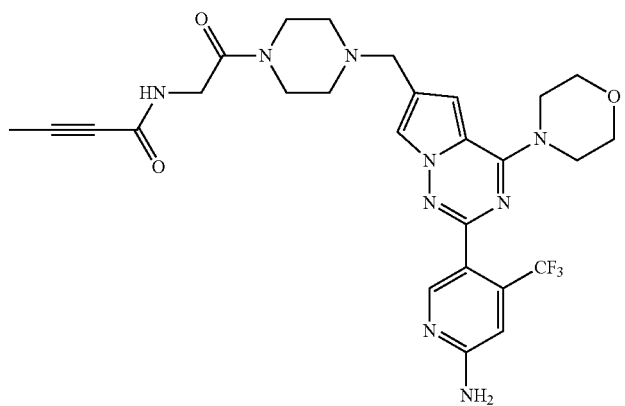 [SMILES: CC#CC(=O)NCC(=O)N1CCN(Cc2cc3c(N4CCOCC4)nc(-c4cnc(N)cc4C(F)(F)F)nn3c2)CC1]

TABLE 1-continued
Non-limiting Examples of ARCS Compounds
Compound 1-129
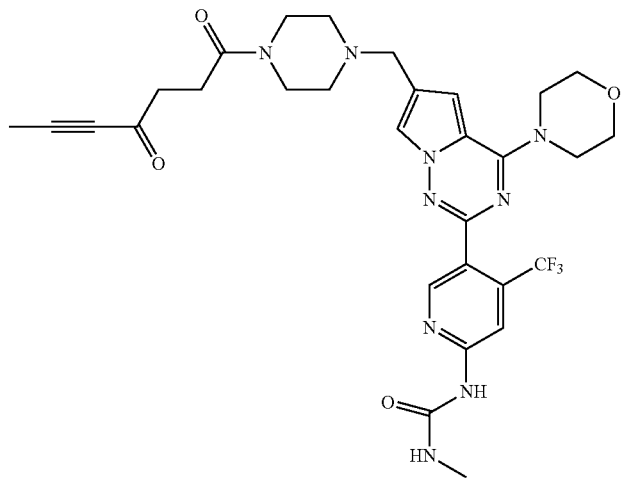 [SMILES: CC#CC(=O)CCC(=O)N1CCN(Cc2cc3c(N4CCOCC4)nc(-c4cnc(NC(=O)NC)cc4C(F)(F)F)nn3c2)CC1]
Compound 1-130
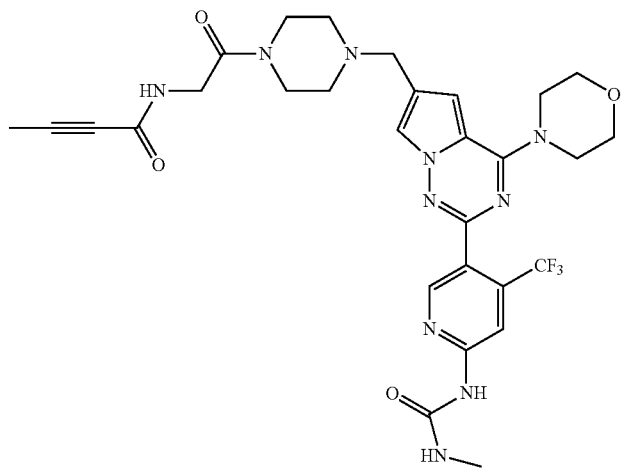 [SMILES: CC#CC(=O)NCC(=O)N1CCN(Cc2cc3c(N4CCOCC4)nc(-c4cnc(NC(=O)NC)cc4C(F)(F)F)nn3c2)CC1]
Compound 1-131
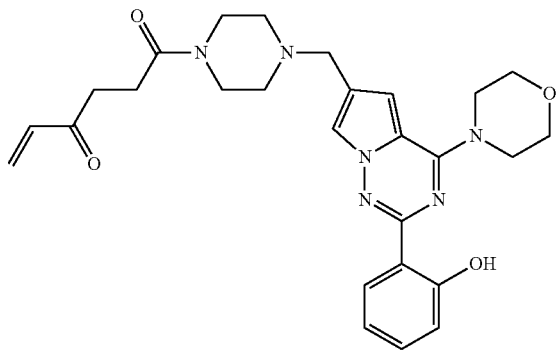

TABLE 1-continued
Non-limiting Examples of ARCS Compounds
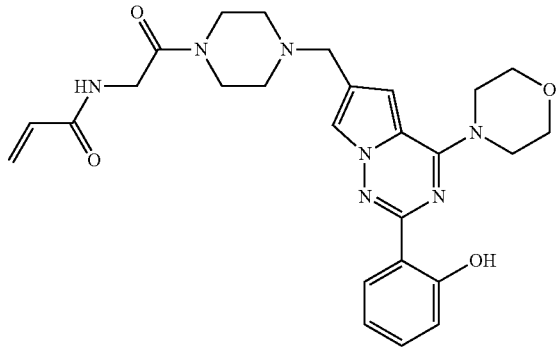 [SMILES: C=CC(=O)NCC(=O)N1CCN(Cc2cc3c(N4CCOCC4)nc(-c4ccccc4O)nn3c2)CC1]
Compound 1-132
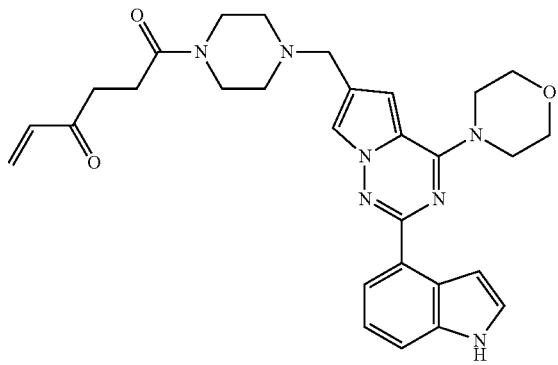 [SMILES: C=CC(=O)CCC(=O)N1CCN(Cc2cc3c(N4CCOCC4)nc(-c4cccc5[nH]ccc45)nn3c2)CC1]
Compound 1-133
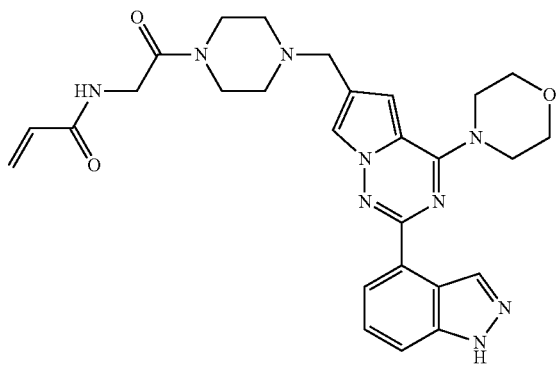
Compound 1-134
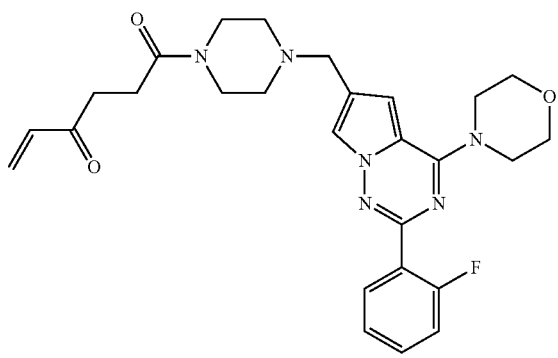
Compound 1-135

TABLE 1-continued
Non-limiting Examples of ARCS Compounds
Compound 1-136
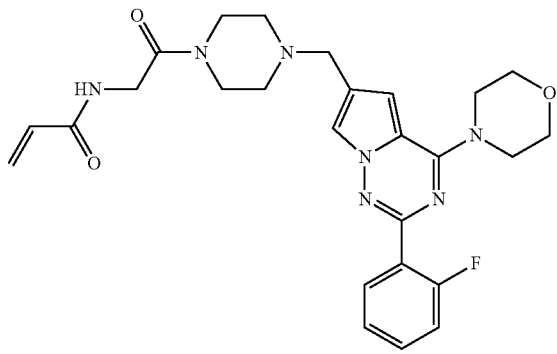
Compound 1-137
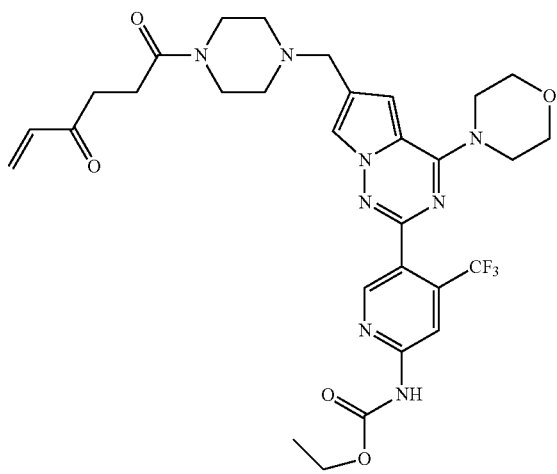 [SMILES: C=CC(=O)CCC(=O)N1CCN(Cc2cc3c(N4CCOCC4)nc(-c4cnc(NC(=O)OCC)cc4C(F)(F)F)nn3c2)CC1]
Compound 1-138
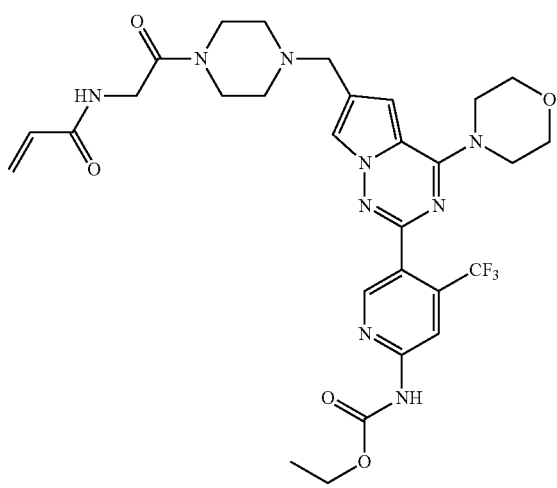 [SMILES: C=CC(=O)NCC(=O)N1CCN(Cc2cc3c(N4CCOCC4)nc(-c4cnc(NC(=O)OCC)cc4C(F)(F)F)nn3c2)CC1]

TABLE 1-continued
Non-limiting Examples of ARCS Compounds
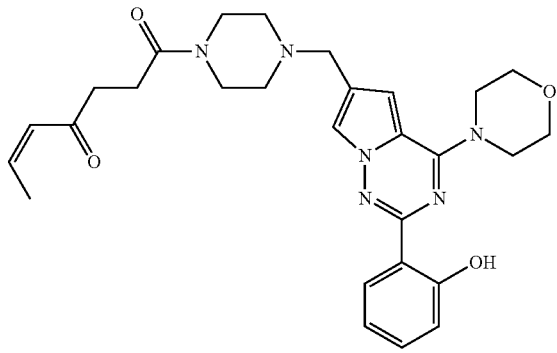 [SMILES: C/C=C\C(=O)CCC(=O)N1CCN(Cc2cc3c(N4CCOCC4)nc(-c4ccccc4O)nn3c2)CC1]
Compound 1-139
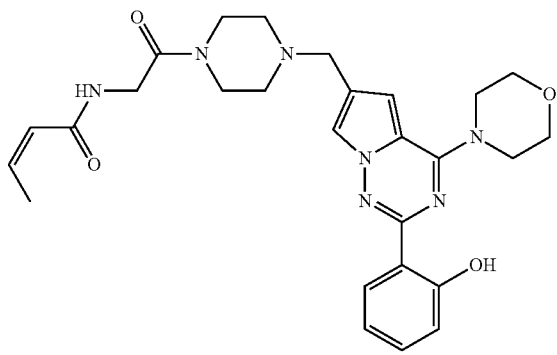 [SMILES: C/C=C\C(=O)NCC(=O)N1CCN(Cc2cc3c(N4CCOCC4)nc(-c4ccccc4O)nn3c2)CC1]
Compound 1-140
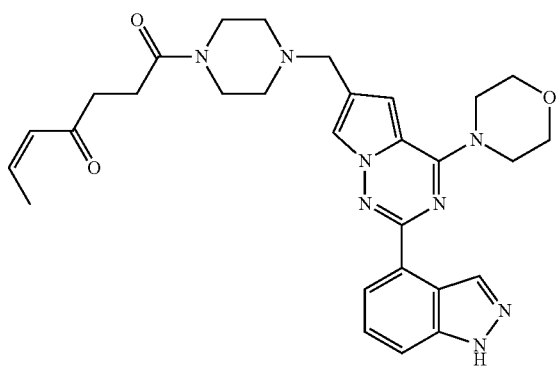 [SMILES: C/C=C\C(=O)CCC(=O)N1CCN(Cc2cc3c(N4CCOCC4)nc(-c4cccc5[nH]ncc45)nn3c2)CC1]
Compound 1-141
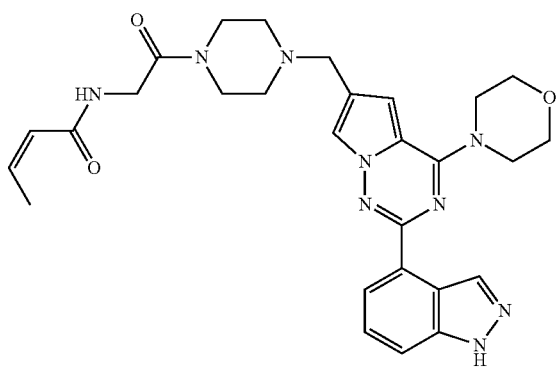 [SMILES: C/C=C\C(=O)NCC(=O)N1CCN(Cc2cc3c(N4CCOCC4)nc(-c4cccc5[nH]ncc45)nn3c2)CC1]
Compound 1-142

TABLE 1-continued
Non-limiting Examples of ARCS Compounds
Compound 1-143
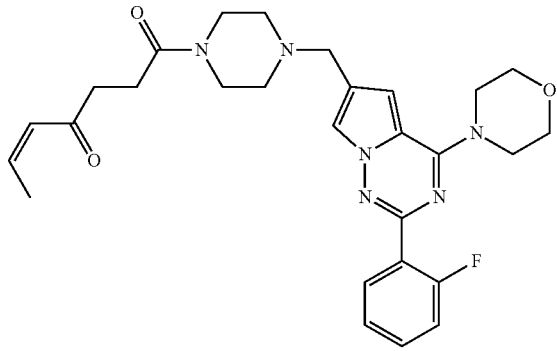 [SMILES: C/C=C\C(=O)CCC(=O)N1CCN(Cc2cc3c(N4CCOCC4)nc(-c4ccccc4F)nn3c2)CC1]
Compound 1-144
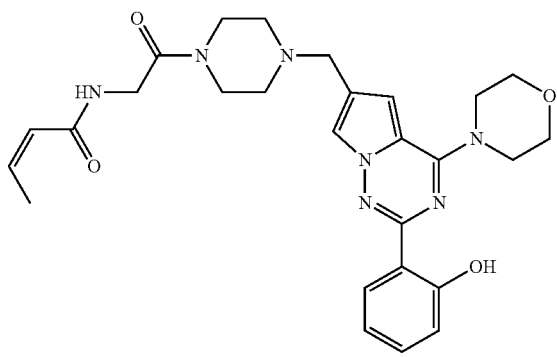 [SMILES: C/C=C\C(=O)NCC(=O)N1CCN(Cc2cc3c(N4CCOCC4)nc(-c4ccccc4O)nn3c2)CC1]
Compound 1-145
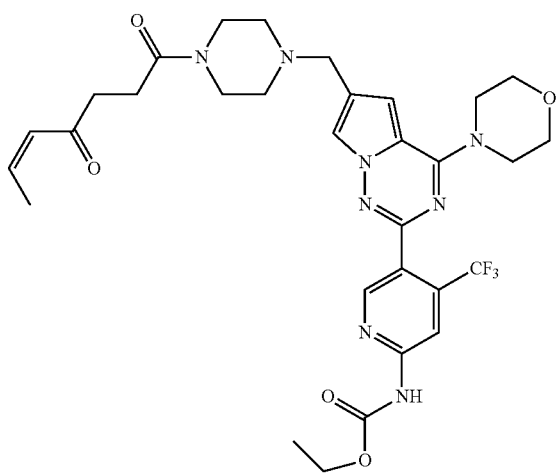 [SMILES: C/C=C\C(=O)CCC(=O)N1CCN(Cc2cc3c(N4CCOCC4)nc(-c4cnc(NC(=O)OCC)cc4C(F)(F)F)nn3c2)CC1]

TABLE 1-continued
Non-limiting Examples of ARCS Compounds
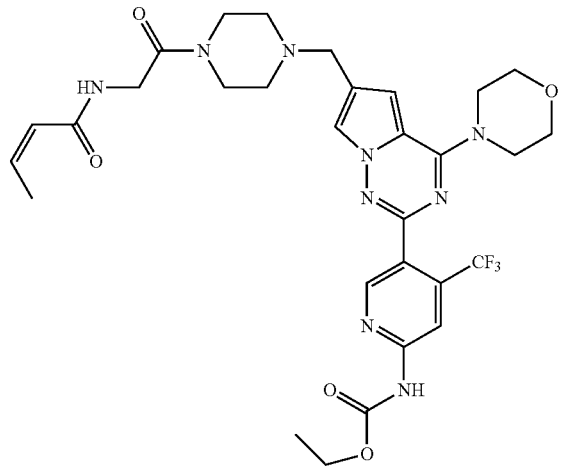 [SMILES: C/C=C\C(=O)NCC(=O)N1CCN(Cc2cc3c(N4CCOCC4)nc(-c4cnc(NC(=O)OCC)cc4C(F)(F)F)nn3c2)CC1]
Compound 1-146
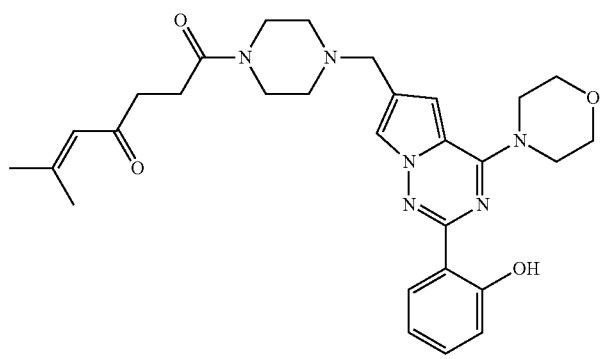 [SMILES: CC(C)=CC(=O)CCC(=O)N1CCN(Cc2cc3c(N4CCOCC4)nc(-c4ccccc4O)nn3c2)CC1]
Compound 1-147
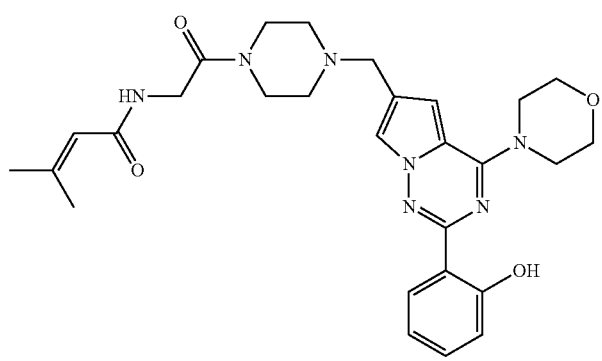 [SMILES: CC(C)=CC(=O)NCC(=O)N1CCN(Cc2cc3c(N4CCOCC4)nc(-c4ccccc4O)nn3c2)CC1]
Compound 1-148
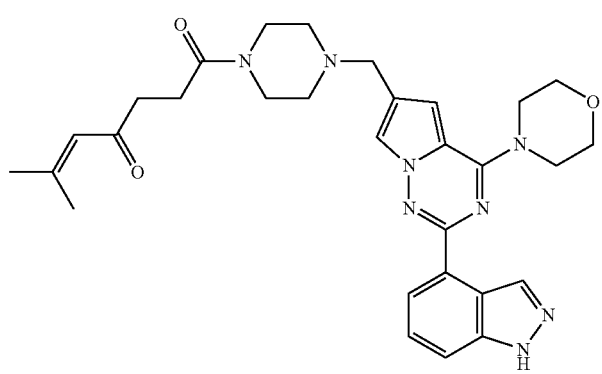 [SMILES: CC(C)=CC(=O)CCC(=O)N1CCN(Cc2cc3c(N4CCOCC4)nc(-c4cccc5[nH]ncc45)nn3c2)CC1]
Compound 1-149

TABLE 1-continued
Non-limiting Examples of ARCS Compounds
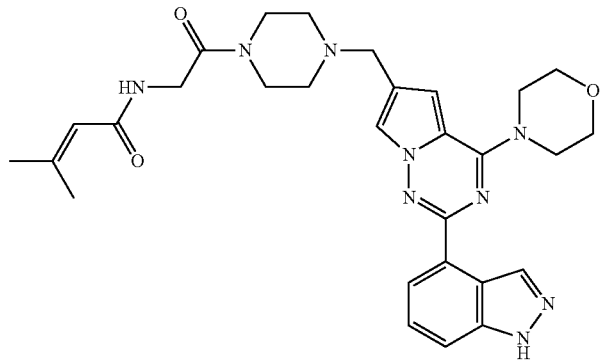
Compound 1-150
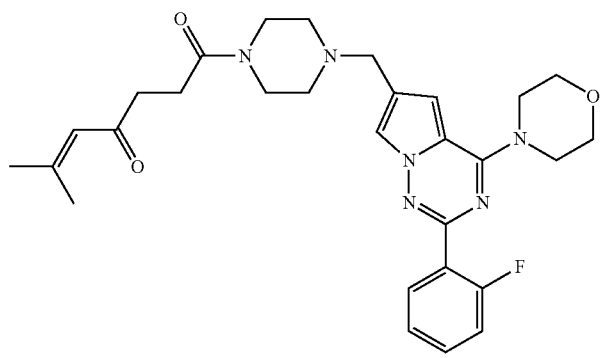 [SMILES: CC(C)=CC(=O)CCC(=O)N1CCN(Cc2cc3c(N4CCOCC4)nc(-c4ccccc4F)nn3c2)CC1]
Compound 1-151
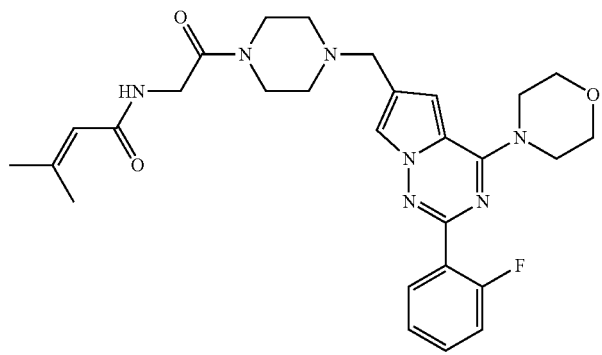 [SMILES: CC(C)=CC(=O)NCC(=O)N1CCN(Cc2cc3c(N4CCOCC4)nc(-c4ccccc4F)nn3c2)CC1]
Compound 1-152
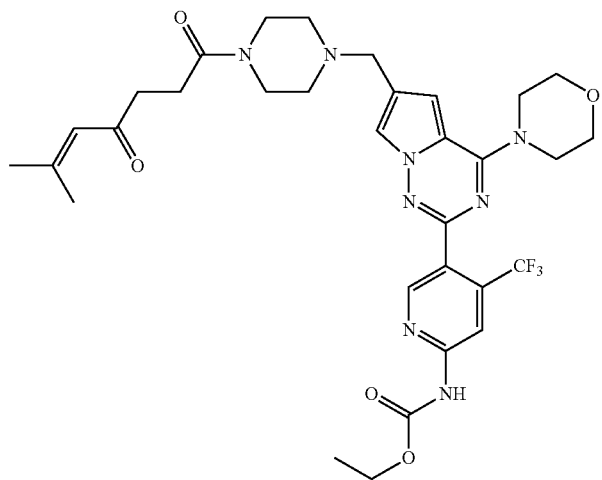 [SMILES: CCOC(=O)Nc1cc(C(F)(F)F)c(-c2nc(N3CCOCC3)c3cc(CN4CCN(C(=O)CCC(=O)C=C(C)C)CC4)cn3n2)cn1]
Compound 1-153

TABLE 1-continued
Non-limiting Examples of ARCS Compounds
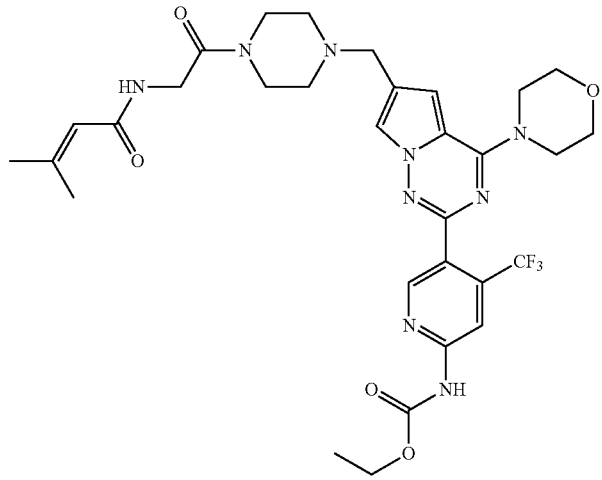 [SMILES: CCOC(=O)Nc1cc(C(F)(F)F)c(-c2nc(N3CCOCC3)c3cc(CN4CCN(C(=O)CNC(=O)C=C(C)C)CC4)cn3n2)cn1]
Compound 1-154
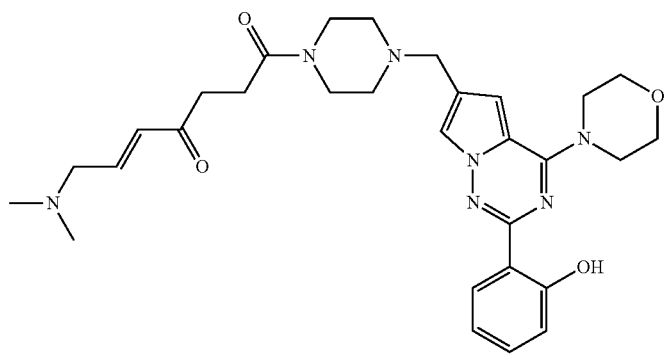
Compound 1-155
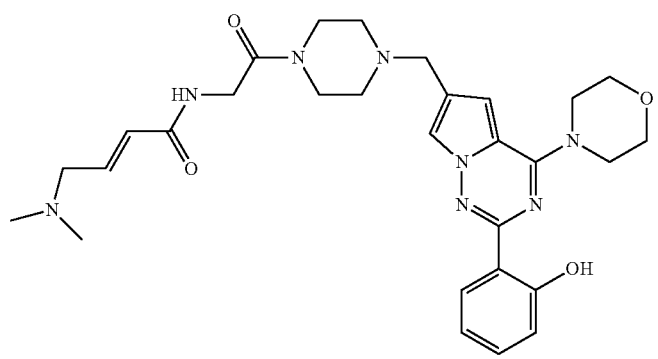 [SMILES: CN(C)C/C=C/C(=O)NCC(=O)N1CCN(Cc2cc3c(N4CCOCC4)nc(-c4ccccc4O)nn3c2)CC1]
Compound 1-156
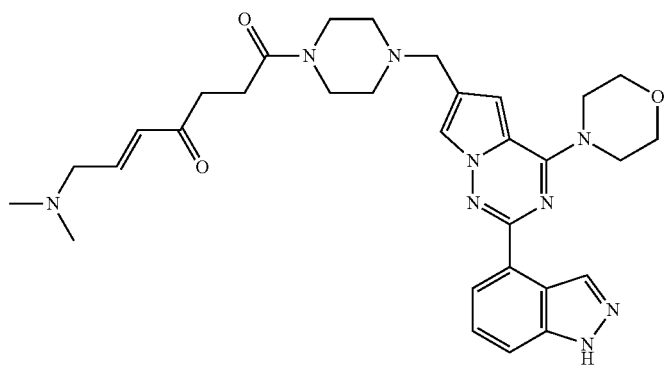 [SMILES: CN(C)C/C=C/C(=O)CCC(=O)N1CCN(Cc2cc3c(N4CCOCC4)nc(-c4cccc5[nH]ncc45)nn3c2)CC1]
Compound 1-157

TABLE 1-continued
Non-limiting Examples of ARCS Compounds
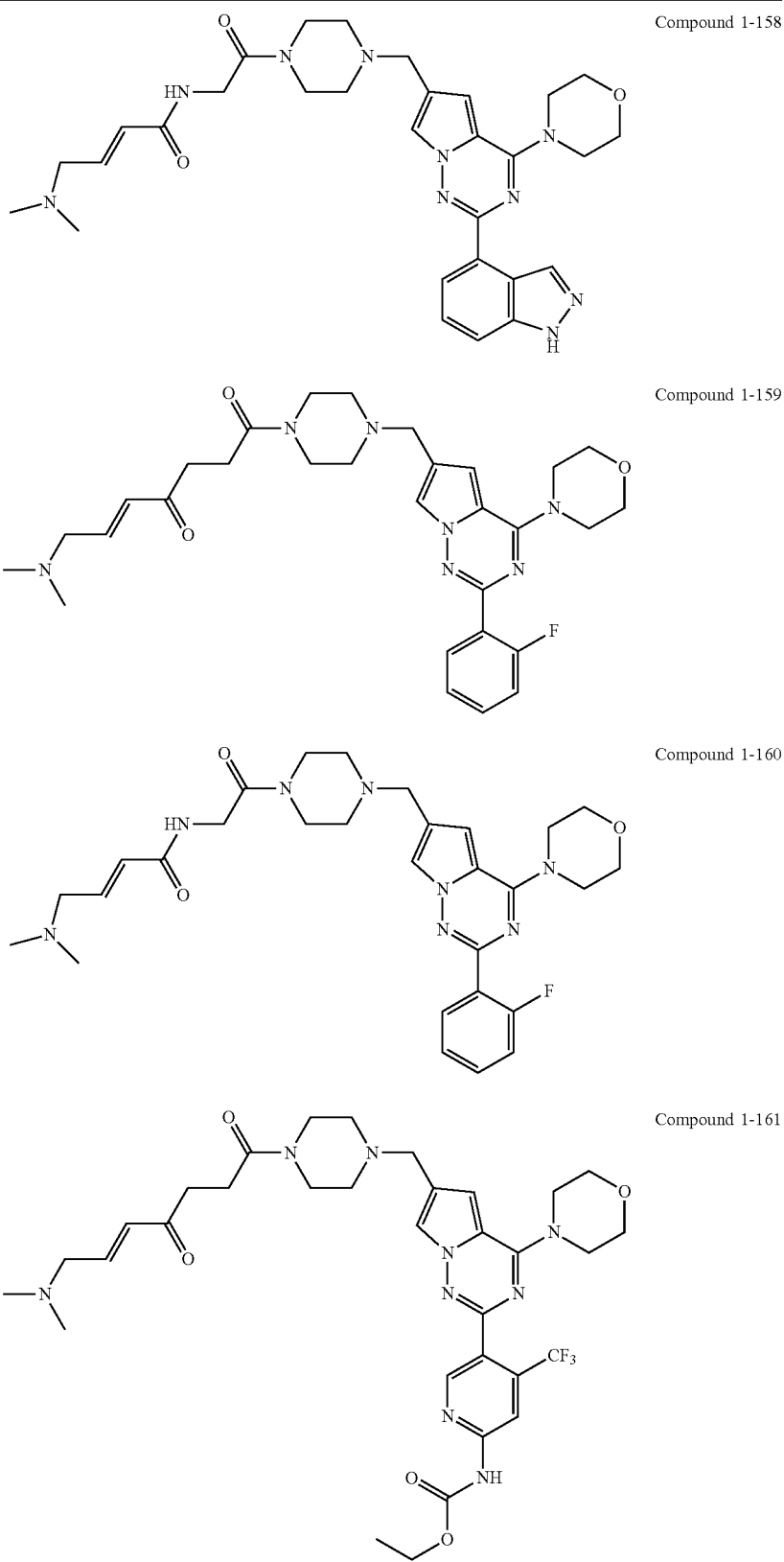
Compound 1-158
Compound 1-159
Compound 1-160
Compound 1-161

TABLE 1-continued
Non-limiting Examples of ARCS Compounds
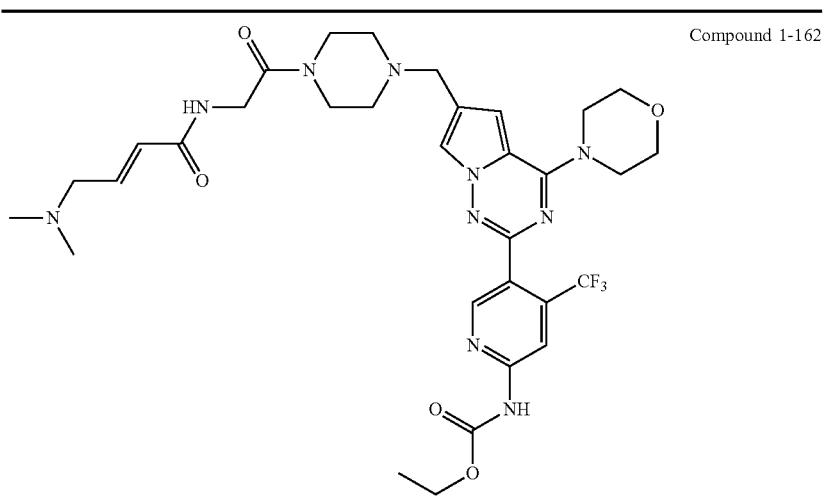
Compound 1-162
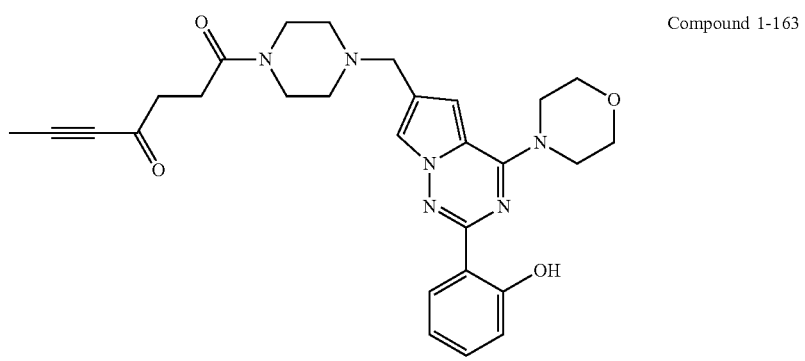
Compound 1-163
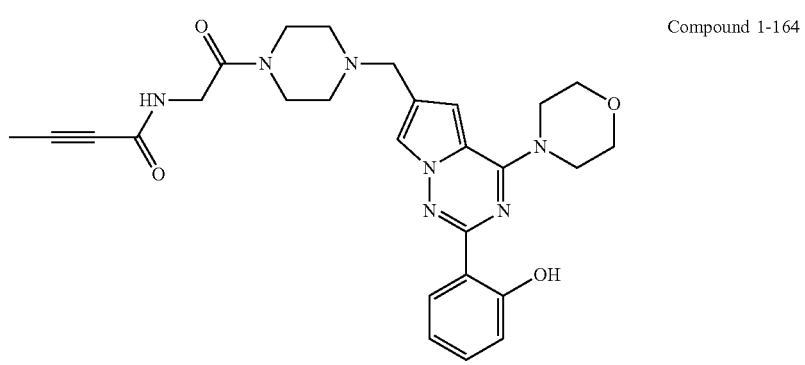
Compound 1-164
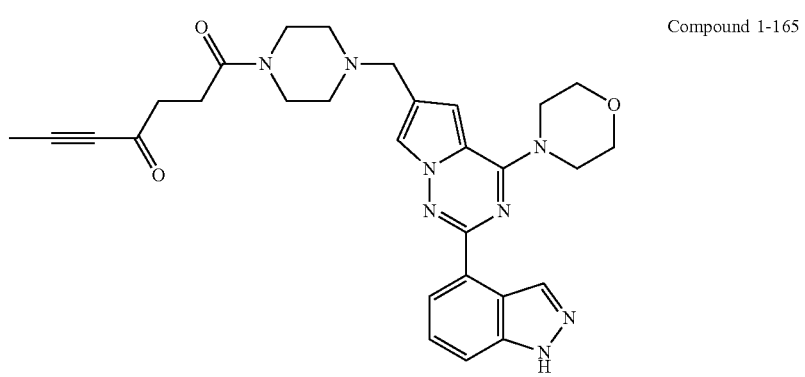
Compound 1-165

TABLE 1-continued
Non-limiting Examples of ARCS Compounds
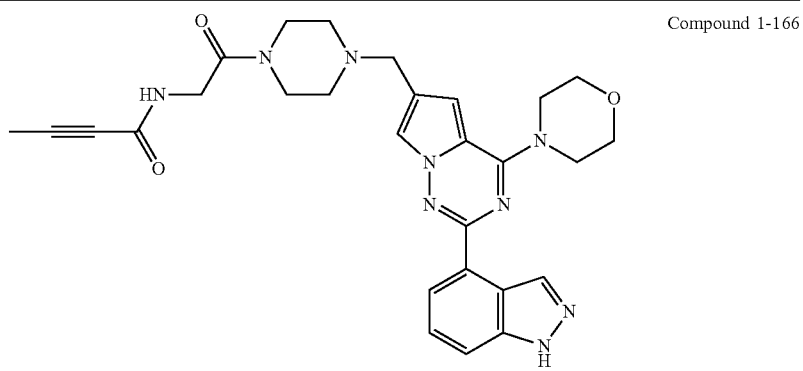
Compound 1-166
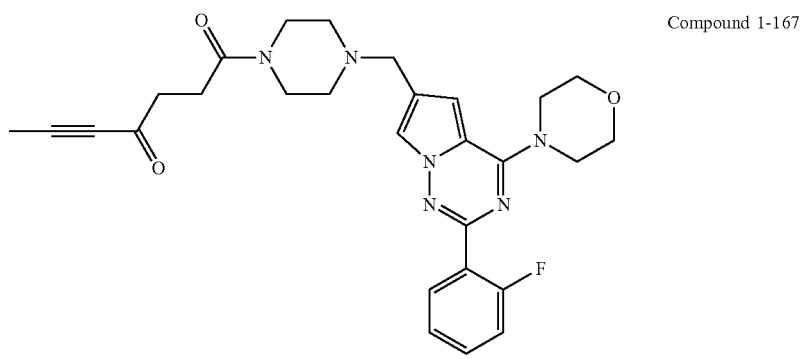
Compound 1-167
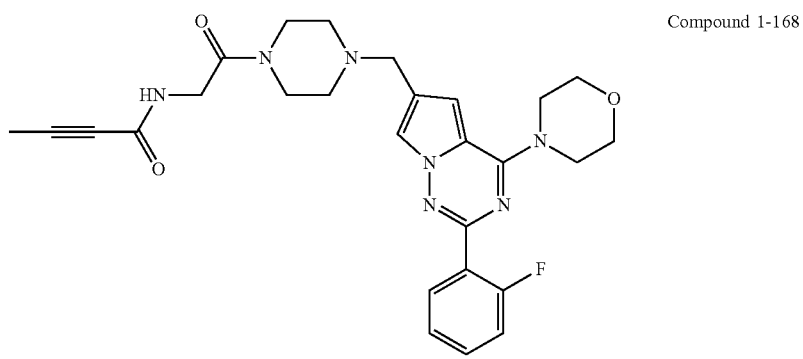
Compound 1-168
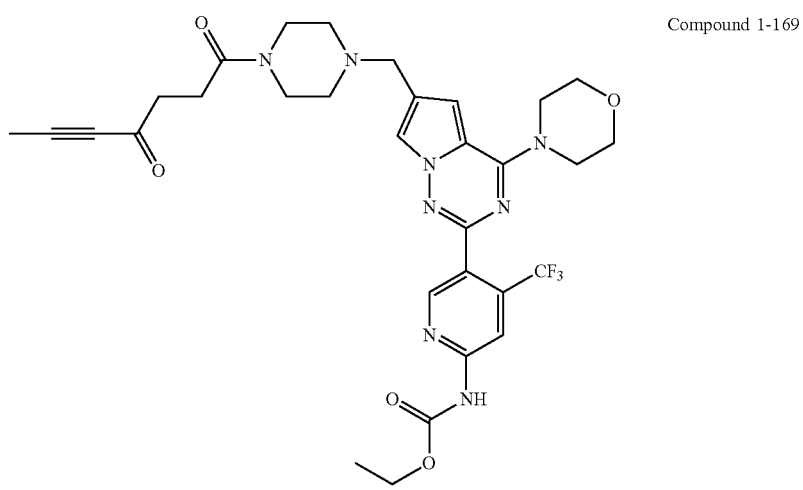
Compound 1-169

TABLE 1-continued

Non-limiting Examples of ARCS Compounds

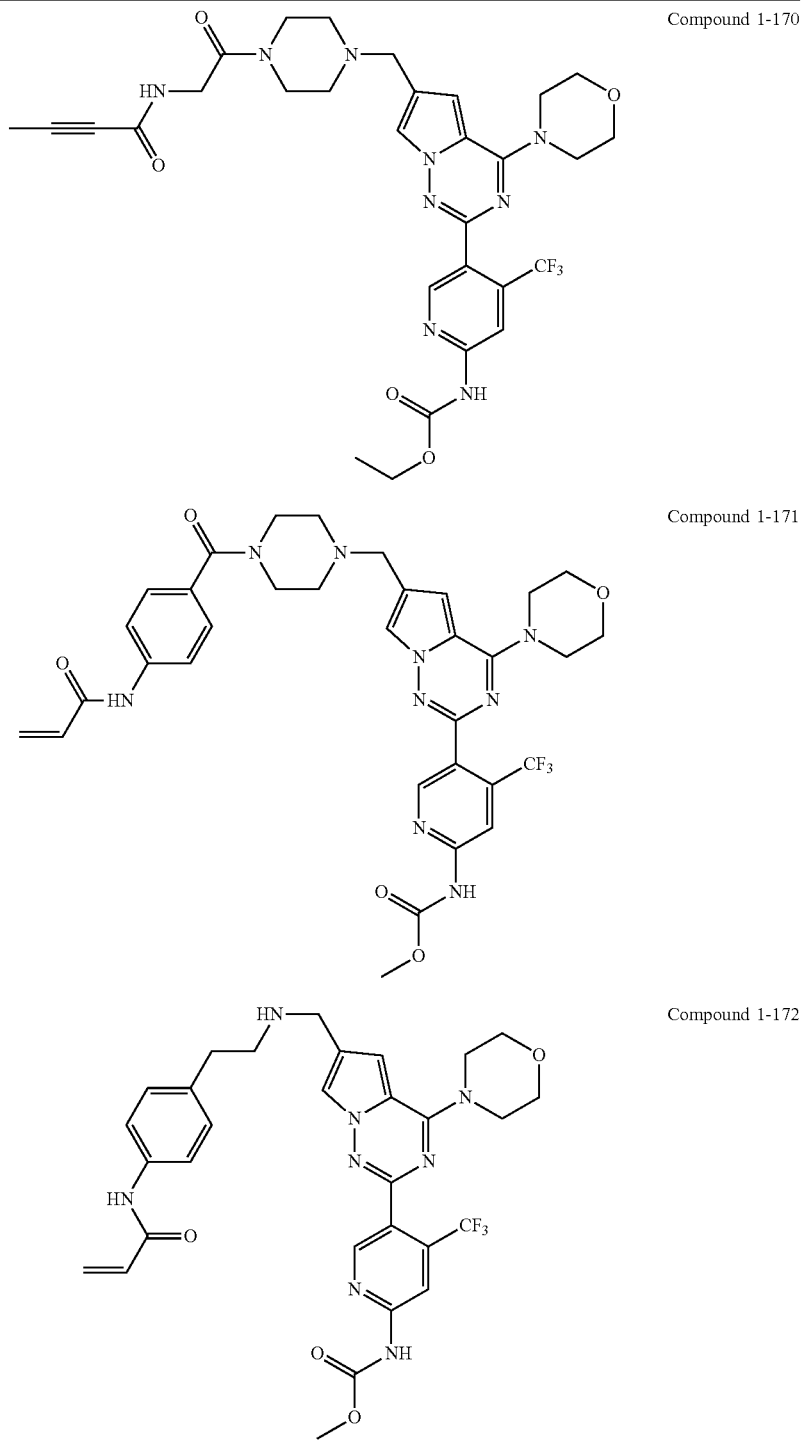

Compound 1-170

Compound 1-171

Compound 1-172 or a pharmaceutically acceptable salt thereof.

E. Pharmaceutical Compositions

The ARCS of the present disclosure may be administered to a subject using any convenient means capable of producing the desired result. Thus, the ARCS of the present disclosure can be incorporated into a variety of formulations for therapeutic administration. More particularly, the ARCS of the present disclosure can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As used herein, the term "pharmaceutical composition" refers to a composition comprising the ARCS as described herein and at least one pharmaceutically acceptable carrier, e.g., any a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Administration of the pharmaceutical compositions can be achieved in various ways, including oral, buccal, rectal, parenteral, intraperitoneal, intradermal, transdermal, intratracheal, etc., administration. In pharmaceutical dosage forms, the pharmaceutical compositions may be administered alone or in combination with other pharmaceutically active compounds.

The amount of ARCS in the pharmaceutical composition can be based on weight, moles, or volume. In some embodiments, the pharmaceutical composition comprises at least 0.0001% of ARCS. In some embodiments, the pharmaceutical composition comprises at least 0.1% of ARCS. In some embodiments, the pharmaceutical composition comprises at least 0.5% of ARCS. In some embodiments, the pharmaceutical composition comprises at least 1% of compounds of ARCS. In some embodiments, the pharmaceutical composition comprises at least 2% of ARCS. In some embodiments, the pharmaceutical composition comprises at least 3% of ARCS. In some embodiments, the pharmaceutical composition comprises at least 4% of ARCS. In some embodiments, the pharmaceutical composition comprises at least 5% of ARCS. In some embodiments, the pharmaceutical composition comprises at least 10% of ARCS. In some embodiments, the pharmaceutical composition comprises 0.05%-90% of the ARCS. In some embodiments, the pharmaceutical composition comprises 0.1%-85% of the ARCS. In some embodiments, the pharmaceutical composition comprises 0.5%-80% of the ARCS. In some embodiments, the pharmaceutical composition comprises 1%-75% of the ARCS. In some embodiments, the pharmaceutical composition comprises 2%-70% of the ARCS. In some embodiments, the pharmaceutical composition comprises 3%-65% of the ARCS. In some embodiments, the pharmaceutical composition comprises 4%-60% of the ARCS. In some embodiments, the pharmaceutical composition comprises 5%-50% of the ARCS.

It will also be appreciated that certain ARCS can exist in free form for treatment, or where appropriate, as a pharmaceutically acceptable derivative thereof. According to the present disclosure, a pharmaceutically acceptable derivative includes, but is not limited to, pharmaceutically acceptable salts, esters, salts of such esters, or a prodrug or other adduct or derivative of ARCS comprising in a composition which upon administration to a patient in need is capable of providing, directly or indirectly, a compound as otherwise described herein, or a metabolite or residue thereof.

As described above, the pharmaceutical compositions of the present disclosure may comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the ARCS together with a suitable carrier to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the ARCS, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the ARCS are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

The ARCS can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the ARCS can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the disclosure to be administered in accordance with the method of the disclosure to a subject will depend upon those factors noted above.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Non-limiting example of a tablet comprises an active ingredient in the amount ranging from 10 mg to 100 mg, powdered lactose in 70 mg to 95 mg, white corn starch in 10 mg to 35 g, polyvinylpyrrolidone in 1 mg to 8 mg, sodium (Na) carboxymethyl starch (CMS) in 1 mg to 10 mg, magnesium stearate in 1 mg to 5 mg, wherein the tablet weight ranges from 200 mg to 3000 mg.

An example of a tablet of the present disclosure is as follows.

| Ingredient | mg/Tablet |
|---|---|
| Active ingredient | 100 |
| Powdered lactose | 95 |
| White corn starch | 35 |
| Polyvinylpyrrolidone | 8 |
| Sodium carboxymethyl starch | 10 |
| Magnesium stearate | 2 |
| Tablet weight | 250 |

Non-limiting example of a capsule comprises an active ingredient in the amount ranging from 10 mg to 100 mg, crystalline lactose in 50 mg to 75 mg, microcrystalline cellulose in 10 mg to 35 g, talc in 1 mg to 8 mg and magnesium stearate in 1 mg to 5 mg, wherein the capsule fill weight ranges from 100 mg to 3000 mg.

An example of a capsule of the present disclosure is as follows.

| Ingredient | mg/Capsule |
|---|---|
| Active ingredient | 50 |
| Crystalline lactose | 60 |
| Microcrystalline cellulose | 34 |

-continued

| Ingredient | mg/Capsule |
| --- | --- |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

Non-limiting example of an injection comprises an active ingredient in the amount ranging from 0.05 mg to 5 mg, 1 N HCl in 10.0 µL to 20.0 µL, acetic acid in 0.1 mg to 1 mg, sodium chloride in 1 mg to 10 mg, phenol in 1 mg to 10 mg, lN NaOH in sufficient quantity to adjust the pH to 4 to 5 and water in sufficient quantity.

An example of an injection solution of the present disclosure is as follows.

| Ineredient | mg/Solution |
| --- | --- |
| Active substance | 1.0 mg |
| 1N HCl | 20.0 µl |
| acetic acid | 0.5 mg |
| NaCl | 8.0 mg |
| Phenol | 10.0 mg |
| 1N NaOH | q.s. ad pH 5 |
| H$_2$O | q.s. ad 1 mL |

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of the ARCS, it is often desirable to slow the absorption of the ARCS from subcutaneous or intramuscular injection. This can be accomplished by the use of a liquid suspension or crystalline or amorphous material with poor water solubility. The rate of absorption of the ARCS then depends upon its rate of dissolution that, in turn, can depend upon crystal size and crystalline form. Alternatively, delayed absorption of a parenterally administered ARCS form is accomplished by dissolving or suspending the ARCS in an oil vehicle. Injectable depot forms are made by forming microencapsulate matrices of the ARCS in biodegradable polymers such as polylactide-polyglycolide. Depending upon the ratio of ARCS to polymer and the nature of the particular polymer employed, the rate of ARCS release can be controlled. Examples of other biodegradable polymers include (poly(orthoesters) and poly(anhydrides). Depot injectable formulations are also prepared by entrapping the ARCS in liposomes or microemulsions which are compatible with body tissues.

Compositions for rectal or vaginal administration are preferably suppositories which can be prepared by mixing the ARCS with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the ARCS or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or nonaqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

Depending on routes of administration, one of skill in the art can determine and adjust an effective dosage of the small molecules disclosed herein to a subject such as a human subject accordingly.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including agricultural animals such as cattle, horses, chickens and pigs, domestic animals such as cats, dogs, or research animals such as mice, rats, rabbits, dogs and nonhuman primates.

II. Methods of Using the ARCS

The ARCS as described herein or compositions containing the ARCS as described herein can be administered to treat any therapeutic disease that can be treated with its FCB or any therapeutic disease associated with the biological target of the ARCS, such as, but not limited to cancer, neurodegenerative diseases, autoimmune diseases or aging, as appropriate. The formulations may be delivered to various body parts, such as but not limited to, brain and central nervous system, eyes, ears, lungs, bone, heart, kidney, liver, spleen, breast, ovary, colon, pancreas, muscles, gastrointestinal tract, mouth, skin, to treat disease associated with such body parts. Formulations may be administered by injection, orally, or topically, typically to a mucosal surface (lung, nasal, oral, buccal, sublingual, vaginally, rectally) or to the eye (intraocularly or transocularly).

In an aspect of the disclosure, ARCS binds to a biological target. In some embodiments, the biological target include kinase, such as, but not limited to phosphoinositide 3-kinases (PI3Ks) and pseudokinase.

In some embodiments, the ARCS can form a covalent bond with a biological target. In some embodiments, the ARCS can form a covalent bond with the biological target from about 5%-100% of the biological target. In some embodiments, the ARCS can form a covalent bond with the biological target from about, 5%, 10%, 15%, 20%, 25%, 30%, 35%, 40%, 45%, 50%, 55%, 60%, 65%, 70%, 75%, 80%, 85%, 90%, 95% or 100% of the biological target.

In some embodiments, the ARCS can form a covalent bond with PI3-kinase. In some embodiments, the ARCS can form a covalent bond with PI3-kinase from about 5%-100% of PI3-kinase. In some embodiments, the ARCS can form a covalent bond with PI3-kinase from about, 5%, 10%, 15%, 20%, 25%, 30%, 35%, 40%, 45%, 50%, 55%, 60%, 65%, 70%, 75%, 80%, 85%, 90%, 95% or 100% of PI3-kinase.

Protein Kinases and Pseudokinases

Protein kinases and pseudokinases regulate signal transduction pathways for a wide variety of biological processes in normal and disease states (Brognard, J. et al. Curr. Opin. Genet. Dev. 2011, 21, pp 4-11; Cohen, P. et al. Nat. Cell Biol. 2002, 4, E127-130). In fact, most eukaryotic processes are regulated by kinases and/or pseudokinases. The term "pseudokinase" refers to proteins with kinase domains that lack catalytically relevant residues including the lysine in the VAIK motif or the aspartic acid in the DFG motif. Examples of pseudokinase include HER3, STRAD, ILK, KSR1, and KSR2. Some pseudokinases are incapable of phosphoryl group transfer, while other pseudokinases have the ability of phosphoryl group transfer even though they lack catalytically relevant residues.

Kinases and pseudokinases can function by inhibiting and/or activating protein partners through binding, covalent modification such as phosphorylation, conformational control, cellular localization, and/or other processes. Protein kinases and pseudokinases can promote and/or antagonize a wide variety of diseases including, but not limited to, cancer, Alzheimer's disease, aging, diabetes, cardiovascular disease, CNS-related diseases, immunological disease, allergy, hypertension, and Parkinson's disease. Protein kinases and pseudokinases are also commonly mutated in multiple diseases including, but not limited to, cancer and Parkinson's disease.

Molecules that target kinases and pseudokinases can act as anticancer agents. Unfortunately, typical inhibitors often show limited potency due to short resonance times on target. Accordingly, there is a need to discover kinase inhibitors with improved resonance times on target and concomitant improved potency and efficacy compared with previous kinase inhibitors.

In some embodiments, the ARCS of the present disclosure may target kinases and pseudokinases, hereby inhibiting the kinases and pseudokinases. The FCB of the ARCS may be an inhibitor for the kinases and pseudokinases. The CLM of the ARCS may bind to the kinases and pseudokinases covalently.

In some embodiments, the present disclosure provides a method of treating a disease, comprising, administering to a patient in need thereof a therapeutically effective amount of a ARCS or compositions comprising ARCS of the present disclosure, or a pharmaceutically acceptable salt thereof, wherein the patient has a disease caused in part or in whole by altered regulation of a target kinase or pseudokinase, such as cancer, Alzheimer's disease, aging, diabetes, cardiovascular disease, CNS-related diseases, immunological disease, allergy, hypertension, or Parkinson's disease. In some embodiments, the disease is associated with PI3K or PI3K is mutated. In some embodiments, the subject has cancer with a mutation in the PIK3CA gene.

Dosing

The present disclosure provides methods comprising administering compositions comprising the ARCS as described herein to a subject in need thereof. Compositions comprising the ARCS as described herein may be administered to a subject using any amount and any route of administration effective for preventing or treating or imaging a disease, disorder, and/or condition. The exact amount required will vary from subject to subject, depending on the species, age, and general condition of the subject, the severity of the disease, the particular composition, its mode of administration, its mode of activity, and the like.

Compositions in accordance with the disclosure are typically formulated in dosage unit form for ease of administration and uniformity of dosage. It will be understood, however, that the total daily usage of the compositions of the present disclosure may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr. period. It may be administered as a single unit dose.

III. Kits and Devices

The present disclosure provides a variety of kits for conveniently and/or effectively carrying out methods of the present disclosure. Typically, kits will comprise sufficient amounts and/or numbers of components to allow a user to perform multiple treatments of a subject(s) and/or to perform multiple experiments.

In one embodiment, the present disclosure provides kits for inhibiting tumor cell growth in vitro or in vivo, comprising an ARCS of the present disclosure or a combination of ARCSs of the present disclosure, optionally in combination with any other active agents.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of the ARCS in the buffer solution over a period of time and/or under a variety of conditions.

The present disclosure provides for devices which may incorporate the ARCS of the present disclosure. These devices contain in a stable formulation available to be immediately delivered to a subject in need thereof, such as a human patient. In some embodiments, the subject has cancer.

Non-limiting examples of the devices include a pump, a catheter, a needle, a transdermal patch, a pressurized olfactory delivery device, iontophoresis devices, multi-layered microfluidic devices. The devices may be employed to deliver conjugates and/or particles of the present disclosure according to single, multi- or split-dosing regiments. The devices may be employed to deliver conjugates and/or particles of the present disclosure across biological tissue, intradermal, subcutaneously, or intramuscularly.

A. Assays

Covalent binding of an ARCS to a biological target may be determined using various methods known in the art such as, but not limited to enzyme-linked immunosorbent assay (ELISA), gel assay, antibody array, western blot, affinity ELISA, ELISPOT, immunochemistry (e.g., IHC), in situ hybridization (ISH), flow cytometry, immunocytology, surface plasmon resonance analysis, kinetic exclusion assay, liquid chromatography-mass spectrometry (LCMS), tandem mass spectrometry (MS/MS), high-performance liquid chromatography (HPLC), BCA assay, immunoelectrophoresis, SDS-PAGE, protein immunoprecipitation, and/or PCR.

As used herein, the term "assay" refers to the sequence of activities associated with a reported result, which can include, but is not limited to: cell seeding, preparation of the test material, infection, lysis, analysis, and calculation of results.

In some embodiments, the assay surfaces on the substrate are sterile and are suitable for culturing cells under conditions representative of the culture conditions during large-scale (e.g., industrial scale) production of the biological product. In some embodiments, the exterior of the substrate comprises wells, indentations, demarcations, or the like at positions corresponding to the assay surfaces. In some embodiments, the wells, indentations, demarcations, or the like retain fluid, such as cell culture media, over the assay surfaces.

In some embodiments, the substrate comprises a microarray plate, a biochip, or the like which allows for the high-throughput, automated testing of a range of test agents, conditions, and/or combinations thereof on the production of a biological product by cultured cells. For example, the substrate may comprise a 2-dimensional microarray plate or biochip having m columns and n rows of assay surfaces (e.g., residing within wells) which allow for the testing of m×n combinations of test agents and/or conditions (e.g., on a 24-, 96- or 384-well microarray plate). The microarray substrates are preferably designed such that all necessary positive and negative controls can be carried out in parallel with testing of the agents and/or conditions.

B. Screening Methods

Generally, the syntheses of therapeutic conjugates that form a covalent bond with a biological target involve multiple synthetic and purification steps. When using such syntheses and purification steps, generating libraries of therapeutic conjugates for screening purposes or developing a structure-activity relationship (SAR) may be difficult. There remains a need for methods and systems that automatically generate therapeutic conjugate libraries by using methods of organic synthesis. To discover therapeutic conjugate drug leads, one has to screen a library of therapeutic conjugates against the protein receptor and identify those molecules that specifically bind to the receptor in a cellular setting, wherein the binding is covalent and irreversible. Identifying whether a therapeutic conjugate covalently binds a specific target in cells has been challenging to prove.

Current methods in the art for screening therapeutic conjugates for their covalent binding to the biological targets include tandem mass spectrometry approach. Tandem MS or MS/MS is a method to break down selected ions into fragment ions. Once samples are ionized to generate a mixture of ions, precursor ions of a specific mass-to-charge ratio (m/z) are selected (MS1) and then fragmented (MS2) to generate product ions for detection. Information about the chemical structure of the selected ion can be then determined from the fragments.

However, there are challenges associated with mass spectrometry approach. Mass spectrometry approaches are largely limited to fragment screens, not drug-like molecule screen. Mass spectrometry analysis of drug-like molecule conjugates would result in unresolved analysis as it will be difficult to identify several fragments. This approach involves multi-step process with long processing times and involves manual analysis. MS/MS will defragment complex, larger molecules making it hard to interpret the resulting data as it requires manually combing through each peptide. Another disadvantage of using mass spectrometry approach is that the detection is proportional to ionization than abundance, making the technique weakly quantitative.

Accordingly, there are challenges associated with synthesis and screening of therapeutic conjugates. First, it is difficult to generate target covalent inhibitors which can access both cysteine and non-cysteine amino acids. It is also difficult to differentiate false positive covalent inhibitors from the real positives.

To address the foregoing issues, the inventors have combined combinatorial synthesis approaches with a reliable screening approach to identify potential therapeutic conjugates. The present disclosure provides a high throughput combinatorial approach to synthesize therapeutic conjugates; rapidly tracks covalent binding; analyzes large libraries for duration of action and directly quantifies covalent target binding in the cell.

Thousands of molecules can be screened per day with picomolar sensitivity as compared to tens of molecules with nanomolar sensitivity by using MS/MS method. The instant disclosure is amenable to any drug molecule and is not restrictive to fragments and gives quantitative results with 95-99% reproducibility.

In some embodiments, the method for screening a library of ARCS comprises:
  generating the library of ARCS in the composition;
  contacting the library with target cells;
  lysing the target cells to generate lysates;
  labeling the lysates; and
  detecting the covalent binding of the ARCS to a biological target on the target cells.

Examples of human cell lines useful in methods provided herein as target cells include, but are not limited to, 293T (embryonic kidney), 786-0 (renal), A498 (renal), A549 (alveolar basal epithelial), ACHN (renal), BT-549 (breast), BxPC-3 (pancreatic), CAKI-1 (renal), Capan-1 (pancreatic), CCRF-CEM (leukemia), COLO 205 (colon), DLD-1 (colon), DMS 114 (small cell lung), DU145 (prostate), EKVX (non-small cell lung), HCC-2998 (colon), HCT-15 (colon), HCT-116 (colon), HT29 (colon), HT-1080 (fibrosarcoma), HEK 293 (embryonic kidney), HeLa (cervical carcinoma), HepG2 (hepatocellular carcinoma), HL-60(TB) (leukemia), HOP-62 (non-small cell lung), HOP-92 (non-small cell lung), HS 578T (breast), HT-29 (colon adenocarcinoma), IGR-OV1 (ovarian), IMR32 (neuroblastoma), Jurkat (T lymphocyte), K-562 (leukemia), KM12 (colon), KM20L2 (colon), LAN5 (neuroblastoma), LNCap.FGC (Caucasian prostate adenocarcinoma), LOX IMVI (melanoma), LXFL 529 (non-small cell lung), M14 (melanoma), M19-MEL (melanoma), MALME-3M (melanoma), MCFlOA (mammary epithelial), MCF7 (mammary), MDA-MB-453 (mammary epithelial), MDA-MB-468 (breast), MDA-MB-231 (breast), MDA-N (breast), MOLT-4 (leukemia), NCI/ADR-RES (ovarian), NCI-H226 (non-small cell lung), NCI-H23 (non-small cell lung), NCI-H322M (non-small cell lung), NCI-H460 (non-small cell lung), NCI-H522 (non-small cell lung), OVCAR-3 (ovarian), OVCAR-4 (ovarian), OVCAR-5 (ovarian), OVCAR-8 (ovarian), P388 (leukemia), P388/ADR (leukemia), PC-3 (prostate), PERC6® (E1-transformed embryonal retina), RPMI-7951 (melanoma), RPMI-8226 (leukemia), RXF 393 (renal), RXF-631 (renal), Saos-2 (bone), SF-268 (CNS), SF-295 (CNS), SF-539 (CNS), SHP-77 (small cell lung), SH-SY5Y (neuroblastoma), SK-BR3 (breast), SK-MEL-2 (melanoma), SK-MEL-5 (melanoma), SK-MEL-28 (melanoma), SK-OV-3 (ovarian), SN12K1 (renal), SN12C (renal), SNB-19 (CNS), SNB-75 (CNS) SNB-78 (CNS), SR (leukemia), SW-620 (colon), T-47D (breast), THP-1 (monocyte-derived macrophages), TK-10 (renal), U87 (glioblastoma), U293 (kidney), U251 (CNS), UACC-257 (melanoma), UACC-62 (melanoma), UO-31 (renal), W138 (lung), and XF 498 (CNS).

Examples of rodent cell lines useful in methods provided herein include, but are not limited to, baby hamster kidney (BHK) cells (e.g., BHK21 cells, BHK TK-cells), mouse Sertoli (TM4) cells, buffalo rat liver (BRL 3A) cells, mouse mammary tumor (MMT) cells, rat hepatoma (HTC) cells, mouse myeloma (NS0) cells, murine hybridoma (Sp2/0) cells, mouse thymoma (EL4) cells, Chinese Hamster Ovary (CHO) cells and CHO cell derivatives, murine embryonic (NIH/3T3, 3T3 L1) cells, rat myocardial (H9c2) cells, mouse myoblast (C2C12) cells, and mouse kidney (miMCD-3) cells.

Examples of non-human primate cell lines useful in methods provided herein include, but are not limited to, monkey kidney (CVI-76) cells, African green monkey kidney (VERO-76) cells, green monkey fibroblast (Cos-1) cells, and monkey kidney (CVI) cells transformed by SV40 (Cos-7). Additional mammalian cell lines are known to those of ordinary skill in the art and are catalogued at the American Type Culture Collection catalog (ATCC®, Mamassas, VA).

In some embodiments, the cells are lysed using chemical and/or mechanical lysis. In some embodiments, the chemical lysis comprises a lysis buffer comprising a protease inhibitor, phosphate buffered saline and Triton X100. In some embodiments, the cells can be frozen after the addition of the lysis buffer at −80° C. for about 30 minutes to about 72 hours. Alternatively, the cell lysate may be stored in a range of 2 to 8° C. or at room temperature. In some embodiments, the cells are centrifuged, and cell lysates are collected. In some embodiments, this is performed by spinning the cells in a centrifuge at 3,750 RPM for 10 minutes at room temperature.

The methods described herein can be performed by utilizing any of a wide range cell assay formats, including, but not limited to cell plates, e.g., 24-well plates, 48-well plates, 96-well plates, or 384-well plates, individual cell culture plates, or flasks, for example T-flasks or shaker flasks.

The covalent binding of ARCS can be detected by assays such as, but not limited to gel assay, NanoBRET assay, western blot, ELISA or microarray. For example, gel assays can include microfluidics or capillary technologies to separate proteins by size.

In some embodiments, the covalent binding is detected by gel assay. The "gel assays" is defined as an assay in which cells or cell lysates are first treated with an ARCS at a dose of 1 picomolar-1 millimolar for a length of time of 2 minutes-120 hours using techniques known to one skill in the art including but not limited common cell culture techniques. The cells are then lysed using techniques known to one skill in the art including but not limited to sonication or buffer lysis. The resulting lysate, also described as unclarified lysate, of the cells can be further prepared to yield a clarified lysate by using techniques known to one skill in the art including but not limited to centrifugation. The clarified or unclarified lysate likely contains protein that is covalently bound to the molecule of interest or molecules of interest. "Coupling reagents" and a labeling molecule are added to the clarified or unclarified lysate to covalently label the ARCS in the reaction mixture with a labeling molecule through a copper-free or copper-driven click chemistry reaction. Compound that binds to labeling molecule is then added which enables reliable resolution of stoichiometry and reliable covalent drug tracking. The sample is then run via a western blot method familiar to one skilled in the art. Subsequently, the amount of covalent binding can be tracking based on the shift of the drug treated band compared to the untreated band. The bands can be quantified using densitometry and relative abundances of the bands can be used to determine the quantitative amount of covalent labeling.

Generally, covalent linking of a large molecular weight protein/mass to ARCS that leads to a shift of the target-ARCS-large molecular weight protein mass complex in a gel can be used. If an azide-linked molecule connected to a high molecular weight protein or molecule of any kind is directly linked to the alkyne on the ARCS, a shift will still occur, and it is possible to detect the covalent binding of the ARCS to the target.

In some embodiments, the covalent binding is detected by gel only shift assay. The "gel only shift assay" is defined as an assay in which a protein is expressed (via transfection or infection) in any cell type and is linked to a tagging domain. This tagging domain includes fluorescent protein or linker protein. The fluorescent proteins include GFP, RFP, etc. This linker proteins include HALO, SNAP-, CLIP-, ACP- and MCP-tags. After transfection or infection, the cells are then treated with a therapeutic conjugate of the present disclosure, wherein the therapeutic conjugate contains an alkyne that can potentially bind covalently. Then, the cells are lysed. In the case of expression of a protein with a linker protein, "coupling reagents" are then added to covalently link a fluorescent dye to the protein of interest. The lysates can then be run on a gel and the target protein visualized via in-gel fluorescence without the need for a western blot transfer. The amount of covalent binding can be tracked based on the shift of the drug treated band compared to the untreated band. The bands can be quantified using densitometry and relative abundances of the bands can be used to determine the quantitative amount of covalent labeling.

The tagging domain can be any domain which allows for labeling of the target. In some embodiments, the tagging domain includes a label. This label can be included in the domain itself such as an epitope recognized by an antibody or a light detectable or radioactive label. In some embodiments, the label is selected from the group consisting of fluorescent markers, such as such as FITC, phycobiliproteins, such as R- or B-phycoerythrin, allophycocyanin, AlexaFluor dyes, Cy3, Cy5, Cy7, a luminescent marker, a radioactive label such as $^{125}$I or $^{32}$P, an enzyme such as horseradish peroxidase, or alkaline phosphatase e.g. alkaline shrimp phosphatase, an epitope, a lectin or biotin/streptavidin.

In some embodiments, a 'fluorescent protein' as used herein is, but not limited to Aequorea victoria green fluorescent protein (GFP), Red fluorescent protein (RFP), structural variants of GFP (i.e., circular permutants, monomeric versions), folding variants of GFP (i.e., more soluble versions, superfolder versions), spectral variants of GFP (i.e., YFP, CFP), and GFP like fluorescent proteins (i.e., Dsked). The term "GFP-like fluorescent protein' is used to refer to members of the Antho Zoa fluorescent proteins sharing the 11-beta strand "barrel structure of GFP as well as structural, folding and spectral variants thereof. The terms "GFP-like non-fluorescent protein' and "GFP-like chromophoric protein' (or, simply, "chromophoric protein' or "chromoprotein') are used to refer to the Anthozoa and Hydrozoa chromophoric proteins sharing the 11-beta strand "barrel structure of GFP, as well as structural, folding and spectral variants thereof.

In some embodiments, the covalent binding is detected by Western blot-based shift assay. The "Western blot-based shift assay" is defined as an assay in which the sample is run via a western blot method familiar to one skilled in the art. Subsequently, the amount of covalent binding can be tracked based on the shift of the target as the covalently bound protein will shift as compared to the non-covalently bound band. The bands can be quantified using densitometry and relative abundances of the bands can be used to determine the quantitative amount of covalent labeling.

In some embodiments, the covalent binding is detected by ELISA assay. In some embodiments, the covalent binding is detected by ELISA assay 1. The "ELISA assay 1" is defined as an assay in which a lysate that contains the biotin-labeled drug is immobilized on a solid support via hybridization with monomeric or tetrameric streptavidin or a streptavidin variant or a molecule that binds biotin. After the drug is immobilized, a detection antibody is added to detect the drug target of interest. The detection antibody can be covalently linked to an enzyme or can itself be detected by a secondary antibody that is linked to an enzyme or fluorescent label. through bioconjugation. Between each step, the plate is typically washed with a solution to remove any proteins or antibodies that are non-specifically bound. After the final wash step, the plate is developed by adding an enzymatic substrate to produce a visible signal, which indicates the quantity of covalent drug binding to the target of interest. The amount of covalent binding can be track based on the amount of signal.

In some embodiments, the covalent binding is detected by ELISA assay 2. The "ELISA assay 2" is defined as an assay in which the target of interest is immobilized on a solid support via hybridization with an antibody that binds the target of interest. After the target of interest is immobilized, a detection antibody or monomeric/tetrameric streptavidin or a streptavidin variant is added to detect the drug bound to the target of interest. The detection antibody or monomeric/tetrameric streptavidin or a streptavidin variant can be covalently linked to an enzyme or fluorescent label or can itself be detected by a secondary antibody that is linked to an enzyme or fluorescent label through bioconjugation. Between each step, the plate is typically washed with a solution to remove any proteins or antibodies that are non-specifically bound. After the final wash step, the plate is developed by adding an enzymatic substrate to produce a visible signal or the fluorescent signal is directly measured, which indicates the quantity of covalent drug binding to the target of interest. The amount of covalent binding can be track based on the amount of signal.

In some embodiments, the covalent binding is detected by antibody array. An "antibody array" is defined as a system in which an individual antibody or multiple antibodies are attached to a solid support to enable detection of proteins of interest that bind that antibody and molecules that bind the protein of interest. The antibody microarray consists of a series of individual dots or wells in which a specific antibody has been hybridized to each dot or well (as described in US Patent 20120231963A1, the contents of which are incorporated herein by reference in their entirety). The coupled clarified or unclarified lysate is added to an "antibody microarray" to enable separation of different proteins, localization of specific proteins to their antibody binding partners, or washing away of additional protein. The labeled molecule of interest is detected at each microarray dot or well to examine the amount of covalent binding of the molecule of interest to a specific protein or multiple proteins by detecting the presence of the biotin labeling molecule to reveal a labeling level. The labeling level at each dot will indicate the amount of covalent labeling of the specific protein that has hybridized to the specific antibody. The biotin label on the molecule can be detected via addition of a fluorescent molecule or luminescent enzyme that binds the label including, but not limited to techniques known to one skilled in the art such as fluorescence, luminescence, FRET, or BRET assays. This readout can be detected using approaches known to one skilled in the art including but not limited to fluorescence or luminescence detections schemes.

In some embodiments, the lysate is labeled with biotin to generate biotinylated compounds. In some embodiments, streptavidin is added to bind to the biotinylated compound. In some embodiments, the streptavidin is monomeric. In some embodiments, the biotinylated compounds are generated by Click chemistry. In some embodiments, the compounds are labeled with click chemistry after the treatment with the ARCS, isolation of cells and cell lysis. In some embodiments, the Click chemistry reagent comprises picolyl azide.

The term "click chemistry," as used herein, refers to the Huisgen cycloaddition or the 2,3-dipolar cycloaddition between an azide and a terminal alkyne to form a 1,2,4-triazole. The term "cycloaddition" as used herein refers to a chemical reaction in which two or more π-electron systems (e.g., unsaturated molecules or unsaturated parts of the same molecule) combine to form a cyclic product in which there is a net reduction of the bond multiplicity. In a cycloaddition, the π electrons are used to form new sigma bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 2,3-dipolar cycloadditions, occur between a 1,3-dipole and a dipolarophile and are typically used for the construction of five-membered heterocyclic rings. The terms "[3+2] cycloaddition" also encompasses "copperless" [3+2]

cycloadditions between azides and cyclooctynes and difluorocyclooctynes described by Bertozzi et al. J. Am. Chem. Soc., 2004, 126:15046-15047. Any reagent that can be used to facilitate the Huisgen cycloaddition can be used as click chemistry reagent. In some embodiments, the click chemistry reagent comprises pyridyl azide. In some embodiments, the click chemistry reagent comprises picolyl azide. Without limitation, any isomer of picolyl azide can be used.

In some embodiments, the ARCS may be associated with or bound to one or more radioactive agents or detectable agents. These agents include various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, $^{3}$H, or $^{99m}$Tc (e.g., as pertechnetate (technetate (VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosine isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, Xrhodamine-5-(and-6)-isothiocyanate (QFITC or XRITC), and fluorescamine); 2-[2-[3-[[1,3-dihydro-1,1-dimethyl-3-(3-sulfopropyl)-2Hbenz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1Hbenz[e]indolium hydroxide, inner salt, compound with N,N-diethylethanamine (1:1) (IR144); 5-chloro-2-[2-[3-[(5-chloro-3-ethyl-2(3H)-benzothiazol-ylidene)ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; ophthaldialdehyde; pyrene and derivatives (e.g., pyrene, pyrene butyrate, and succinimidyl 1-pyrene); butyrate quantum dots; Reactive Red 4(CIBACRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalol cyanine.

In some embodiments, the detectable agent may be a non-detectable precursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))).

IV. Definitions

The term "ARCS" as used herein, refers to any therapeutic conjugate that is formed by linking an FCB and a CLM with a bond or a linker. In some embodiments, the ARCS can form a covalent bond with one or multiple targets such as nucleotides, oligonucleotides, peptides, or proteins. In some embodiments, the covalent bond is formed in an aqueous solution at a temperature of 0-50° C., within 48 hours, and at a treatment dose of 10 mM.

The term "FCB" as used herein, refers to a therapeutic modality that can be a known drug, a diagnostic compound, a drug candidate and a functional fragment and/or combination of any of the forgoing. The FCB encompasses free acid and free base forms; optical and tautomeric isomers; isotopes including radioisotopes and pharmaceutically acceptable salts of the drug, prodrug or fragment thereof. The FCBs may be small molecules, proteins, peptides, lipids, carbohydrates, sugars, nucleic acids, or combination thereof. In some embodiments, the FCBs are nucleic acids including, but is not limited to DNA or RNA. The FCB may be a therapeutic agent such as, but not limited to, anti-cancer agents, anti-neurodegenerative agents, autoimmune drugs and anti-aging agents. The FCB may bind to a biological target non-covalently. In some embodiments, the FCB may be a functional fragment of a drug. The term "functional fragment" as used herein, refers to a part of a drug or derivative or analog thereof that is capable of inducing a desired effect of the drug. In some embodiments, the FCB may comprise an alkyne functional group. In some embodiments, the FCB may not comprise an alkyne functional group.

The term "CLM" as used herein, refers to any covalent binding modality that is capable of forming a covalent bond with the biological target. The CLM may be linked to an FCB by a bond or by a linker. The CLM may comprise one or more chemical moieties which can form a covalent bond with the biological target. The chemical moieties may be an electrophilic or nucleophilic group.

The term "linker" as used herein, refers to an organic moiety that connects two parts of a compound. The linker can be external linker or internal linker. The external linker can connect FCB and CLM moieties. Internal linker can be used to join CLM moiety. In certain embodiments, the CLM may comprise an internal linker or a spacer. The internal linker or spacer may combine two parts of the CLM or can be joined to the CLM. External or internal linker can be selected from the group consisting of a bond, substituted and unsubstituted $C_1$-$C_{30}$ alkyl, substituted and unsubstituted $C_2$-$C_{30}$ alkenyl, substituted and unsubstituted $C_2$-$C_{30}$ alkynyl, substituted and unsubstituted $C_3$-$C_{30}$ cycloalkyl, substituted and unsubstituted $C_1$-$C_{30}$ heterocycloalkyl, substituted and unsubstituted $C_3$-$C_{30}$ cycloalkenyl, substituted and unsubstituted $C_1$-$C_{30}$ heterocycloalkenyl, substituted and unsubstituted aryl, and substituted and unsubstituted heteroaryl. The linker can be cleavable or non-cleavable.

The term "biological target", as used herein, refers to any target to which an FCB binds non-covalently to product a therapeutic effect. A CLM binds to the biological target covalently. In some embodiments, the biological target is a protein.

The term "toxicity" as used herein, refers to the capacity of a substance or composition to be harmful or poisonous to a cell, tissue organism or cellular environment. Low toxicity refers to a reduced capacity of a substance or composition to be harmful or poisonous to a cell, tissue organism or cellular environment. Such reduced or low toxicity may be relative to a standard measure, relative to a treatment or relative to the absence of a treatment.

The term "compound", as used herein, is meant to include all stereoisomers, geometric isomers, tautomers, and isotopes of the structures depicted. In some embodiments, compound is used interchangeably with the ARCS. Therefore, ARCS, as used herein, is also meant to include all stereoisomers, geometric isomers, tautomers, and isotopes of the structures depicted. The FCBs and CLMs, as used herein, are also meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

The terms "subject" or "patient", as used herein, refer to any organism to which the particles may be administered, e.g., for experimental, therapeutic, diagnostic, and/or prophylactic purposes. Typical subjects include animals (e.g., mammals such as mice, rats, rabbits, guinea pigs, cattle, pigs, sheep, horses, dogs, cats, hamsters, lamas, non-human primates, and humans).

The terms "treating" or "preventing", as used herein, can include preventing a disease, disorder or condition from occurring in an animal that may be predisposed to the disease, disorder and/or condition but has not yet been diagnosed as having the disease, disorder or condition; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

A "target", as used herein, shall mean a site to which ARCS, FCB and/or CLM bind. A target may be either in vivo or in vitro. In certain embodiments, a target may be cancer cells found in leukemias or tumors (e.g., tumors of the brain, lung (small cell and non-small cell), ovary, prostate, breast and colon as well as other carcinomas and sarcomas). A target may be a type of tissue, e.g., neuronal tissue, intestinal tissue, pancreatic tissue, liver, kidney, prostate, ovary, lung, bone marrow, or breast tissue The "target cells" that may serve as the target for the therapeutic conjugate are generally animal cells, e.g., mammalian cells. The present method may be used to modify cellular function of living cells in vitro, i.e., in cell culture, or in vivo, in which the cells form part of or otherwise exist in animal tissue. Thus, the target cells may include, for example, the blood, lymph tissue, cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject), dermal/epidermal cells, cells of the vagina and rectum, cells of internal organs including cells of the placenta and the so-called blood/brain barrier, etc.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human.

The term "modulation" is art-recognized and refers to up regulation (i.e., activation or stimulation), down regulation (i.e., inhibition or suppression) of a response, or the two in combination or apart.

"Parenteral administration", as used herein, means administration by any method other than through the digestive tract (enteral) or non-invasive topical routes. For example, parenteral administration may include administration to a patient intravenously, intradermally, intraperitoneally, intrapleurally, intratracheally, intraosseously, intracerebrally, intrathecally, intramuscularly, subcutaneously, subjunctivally, by injection, and by infusion.

"Topical administration", as used herein, means the non-invasive administration to the skin, orifices, or mucosa. Topical administrations can be administered locally, i.e., they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

"Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

The terms "sufficient" and "effective", as used interchangeably herein, refer to an amount (e.g., mass, volume, dosage, concentration, and/or time period) needed to achieve one or more desired result(s). A "therapeutically effective amount" is at least the minimum concentration required to affect a measurable improvement or prevention of at least one symptom or a particular condition or disorder, to effect a measurable enhancement of life expectancy, or to generally improve patient quality of life. The therapeutically effective amount is thus dependent upon the specific biologically active molecule and the specific condition or disorder to be treated. Therapeutically effective amounts of many active agents, such as antibodies, are known in the art. The therapeutically effective amounts of compounds and compositions described herein, e.g., for treating specific disorders may be determined by techniques that are well within the craft of a skilled artisan, such as a physician.

The term "prodrug" refers to an agent, including a nucleic acid or protein that is converted into a biologically active form in vitro and/or in vivo. Prodrugs can be useful because, in some situations, they may be easier to administer than the parent compound. For example, a prodrug may be bioavailable by oral administration whereas the parent compound is not. The prodrug may also have improved solubility in pharmaceutical compositions compared to the parent drug. A prodrug may be converted into the parent drug by various mechanisms, including enzymatic processes and metabolic hydrolysis. Harper, N.J. (1962) Drug Latentiation in Jucker, ed. *Progress in Drug Research*, 4:221-294; Morozowich et al. (1977) Application of Physical Organic Principles to Prodrug Design in E. B. Roche ed. *Design of Biopharmaceutical Properties through Prodrugs and Analogs*, APhA; Acad. Pharm. Sci.; E. B. Roche, ed. (1977) *Bioreversible Carriers in Drug in Drug Design. Theory and Application*, APhA; H. Bundgaard, ed. (1985) *Design of Prodrugs*, Elsevier; Wang et al. (1999) Prodrug approaches to the improved delivery of peptide drug, *Curr. Pharm. Design.* 5(4):265-287; Pauletti et al. (1997) Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996) Designing Prodrugs and Bioprecursors I. Carrier Prodrugs, *Pract. Med. Chem.* 671-696; M. Asghamejad (2000). Improving Oral Drug Transport Via Prodrugs, in G. L. Amidon, P. I. Lee and E. M. Topp, Eds., *Transport Processes in Pharmaceutical Systems*, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogs, *Adv. Drug Delivery Rev.*, 39(1-3):183-209; Browne (1997). Fosphenytoin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) *Design of Prodrugs*. New York: Elsevier; Fleisher et al. (1996) Improved oral drug delivery: solubility limitations overcome by the use of prodrugs, *Adv. Drug Delivery Rev.* 19(2): 115-130; Fleisher et al. (1985) Design of prodrugs for improved gastrointestinal absorption by intestinal enzyme targeting, *Methods Enzymol.* 112: 360-81; Farquhar D, et al. (1983) Biologically Reversible Phosphate-Protective Groups, *J. Pharm. Sci.*, 72(3): 324-325; Han, H. K. et al. (2000) Targeted prodrug design to optimize drug delivery, *AAPS PharmSci.*, 2(1): E6; Sadzuka Y. (2000) Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl. 2:S15-27; Wang, W. et al. (1999) Prodrug approaches to the improved delivery of peptide drugs. *Curr. Pharm. Des.*, 5(4):265-87.

The term "pharmaceutically acceptable", as used herein, refers to compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration. A "pharmaceutically acceptable carrier", as used herein, refers to all components of a pharmaceutical formulation that facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than 2000 g/mol in molecular weight, less than 1500 g/mol, less than 1000 g/mol, less than 800 g/mol, or less than 500 g/mol. Small molecules are non-polymeric and/or non-oligomeric.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

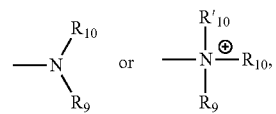

wherein R$_9$, R$_{10}$, and R'$_{10}$ each independently represent a hydrogen, an alkyl, an alkenyl, —(CH$_2$)$_m$—R$_8$ or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In some embodiments, only one of R$_9$ or R$_{10}$ can be a carbonyl, e.g., R$_9$, R$_{10}$ and the nitrogen together do not form an imide. In still other embodiments, the term "amine" does not encompass amides, e.g., wherein one of R$_9$ and R$_{10}$ represents a carbonyl. In additional embodiments, R$_9$ and R$_{10}$ (and optionally R'$_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R$_9$ and R$_{10}$ is an alkyl group.

The term "amido" is art-recognized as an amino-substituted carbonyl and includes a moiety that can be represented by the general formula:

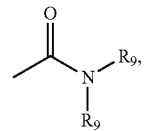

wherein R$_9$ and R$_{10}$ are as defined above.

"Aryl", as used herein, refers to C$_5$-C$_{10}$-membered aromatic, heterocyclic, fused aromatic, fused heterocyclic, biaromatic, or biheteroeocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

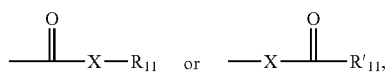

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analog of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, or elimination.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The terms "polypeptide," "peptide" and "protein" generally refer to a polymer of amino acid residues. As used herein, the term also applies to amino acid polymers in which one or more amino acids are chemical analogs or modified derivatives of corresponding naturally occurring amino acids. The term "protein", as generally used herein, refers to a polymer of amino acids linked to each other by peptide bonds to form a polypeptide for which the chain length is sufficient to produce tertiary and/or quaternary structure. The term "protein" excludes small peptides by definition, the small peptides lacking the requisite higher-order structure necessary to be considered a protein.

A "functional fragment" of a protein, polypeptide or nucleic acid is a protein, polypeptide or nucleic acid whose sequence is not identical to the full-length protein, polypeptide or nucleic acid, yet retains at least one function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA binding function of a polypeptide can be determined, for example, by filter-binding, electrophoretic mobility shift, or immunoprecipitation assays. DNA cleavage can be assayed by gel electrophoresis. The ability of a protein to interact with another protein can be determined, for example, by co-immunoprecipitation, two-hybrid assays or complementation, e.g., genetic or biochemical. See, for example, Fields et al. (1989) *Nature* 340:245-246; U.S. Pat. No. 5,585,245 and PCT WO 98/44350.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, malate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, malate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

As used herein, the term "assay" refers to the sequence of activities associated with a reported result, which can include, but is not limited to: cell seeding, preparation of the test material, infection, lysis, analysis, and calculation of results.

The term "detectable response" as used herein refers to an occurrence of, or a change in, a signal that is directly or indirectly detectable either by observation or by instrumentation. Typically, the detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety.

EXAMPLES

Example 1: General Synthesis of the ARCS

The ARCS of the present disclosure can be synthesized by one skilled in the art using general chemical synthetic principles and techniques. In a rational approach, the ARCSs are constructed from their individual components: the therapeutic modality, the optional linker, and the covalent binding modality. The components can be covalently bonded to one another through functional groups, as is known in the art, where such functional groups may be present on the components or introduced onto the components using one or more steps. Functional groups that may be used in covalently bonding the components together to produce the ARCSs include but not limited to hydroxy, sulfhydryl, or amino groups. The particular portion of the different components that are modified to provide for covalent linkage is chosen so as not to substantially adversely interfere with that components desired binding activity, e.g., for the covalent binding modality, a region that does not affect the covalent binding activity will be modified, such that a sufficient amount of the desired activity is preserved. When necessary and/or desired, certain moieties on the components may be protected using blocking groups, as is known in the art, see, e.g., Green & Wuts, Protective Groups in Organic Synthesis (John Wiley & Sons) (1991).

Alternatively, the ARCSs can be produced using known combinatorial methods to produce large libraries of ARCSs which may then be screened for identification of a molecule that forms a covalent bond with a target with a desirable pharmacokinetic profile.

Example 2: General Synthesis of Compound 1-1 to Compound 1-172

Compound 1-1 to Compound 1-172 of the present disclosure can be synthesized by one skilled in the art using general chemical synthetic principles and techniques. The chemistry is as described in Example 1 of U.S. Pat. No. 9,724,352 B2, the contents of which are incorporated herein by reference in their entirety.

Compound 1-IV, a precursor to many of the Compound 1-1 to Compound 1-172, can be prepared as shown in Scheme 1. As described in U.S. Pat. No. 9,724,352, starting pyrrole (1-I) can be reacted with aldehyde (1-II) to form intermediate (1-III). Morpholino compound 1-IV can be formed by reducing compound (1-III) with phosphorous oxychloride to provide a Cl-leaving group, which can then be replaced by the addition of morpholine. If $R_6'$ in 1-IV is a nitro group, it can be reduced to the corresponding $NH_2$ group by reacting with C/Pd under H2 atmosphere. The amine can then be further reacted with an appropriate ester (e.g., dimethyl carbonate) or activated ester (e.g., methylchloroformate) to form the methyl-carbamate of compound or it can be reacted with an isocyanate (e.g., methyl isocyanate) to provide urea compound 1-VA.

compound 1-V or it can be reacted with an isocyanate (e.g., methyl isocyanate) to provide urea compound 1-VII$_A$ (see, for example, groups Compound 1-105 and Compound 1-106). The amine group of compound 1-VI can also be protected (not shown) if it is a final desired group (see Compound 1-121). After the desired X group is added, the amino-protecting group could then be removed to provide the final product. For example, N-acetyl-piperazine instead of N-BOC-piperazine could be used to provide an N-acetyl protecting group in compound 1-VI. The amino group of compound 1-VI could then be protected with an N-BOC group, which is more stable than N-acetyl. Compound 1-VI could then be modified with an X group and the N-BOC removed to leave the final amino group.

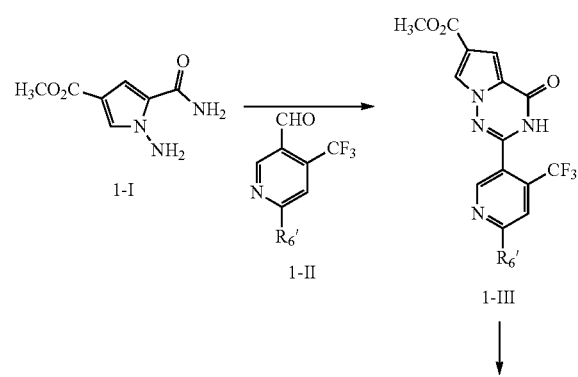

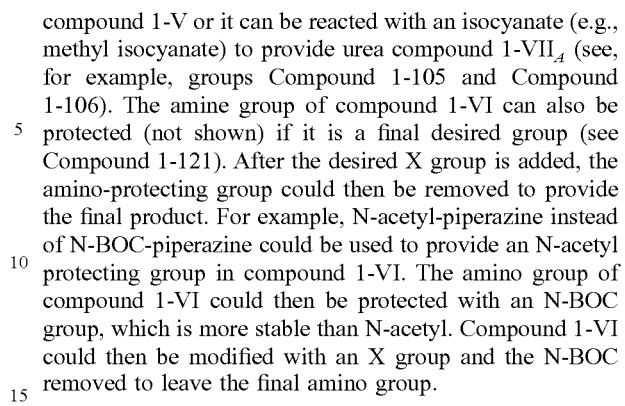

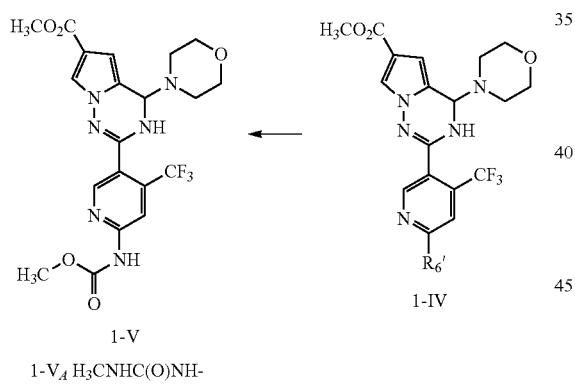

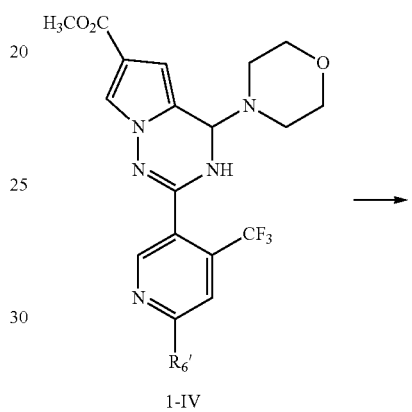

In order to arrive at piperazinyl compounds (e.g., Compound 1-11 and Compound 1-12), it can be advantageous to modify the methyl ester moiety of Compound 1-IV prior to converting $R_6'$ to a final $R_6$ group. As noted above, if $R_6'$ in 1-IV is a nitro group, it can be reduced by Pd/C under $H_2$ atmosphere to the corresponding $NH_2$ group. As shown in Scheme 2, the methyl ester of 1-IV can then be hydrolyzed (e.g., 2 M aqueous NaOH in EtOH) and the resulting acid reacted with tert-butyl piperazine-1-carboxylate (1-BOC-piperazine) in the presence of a base (e.g., $K_2CO_3$) to provide BOC-piperazinyl compounds. The carbonyl moiety remaining after piperazinyl addition can then be reduced (e.g., borane-dimethyl sulfide) to provide protected piperazinyl compound 1-VI. As noted above, the amine group of Compound 1-VI can then be further reacted with an appropriate ester (e.g., dimethyl carbonate) or activated ester (e.g., methylchloroformate) to form the methyl-carbamate of

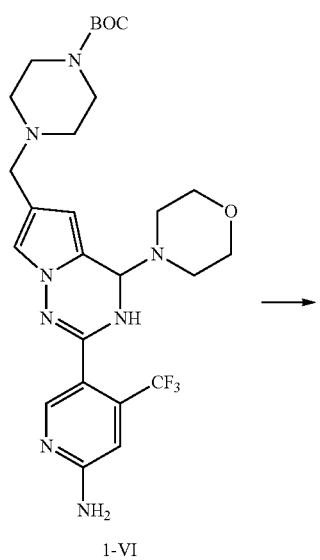

-continued

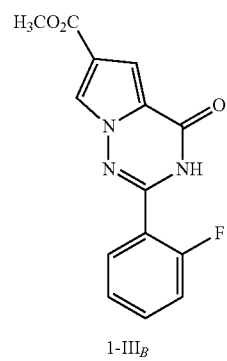

1-VII
1-VII$_A$ H$_3$CNHC(O)NH-

-continued

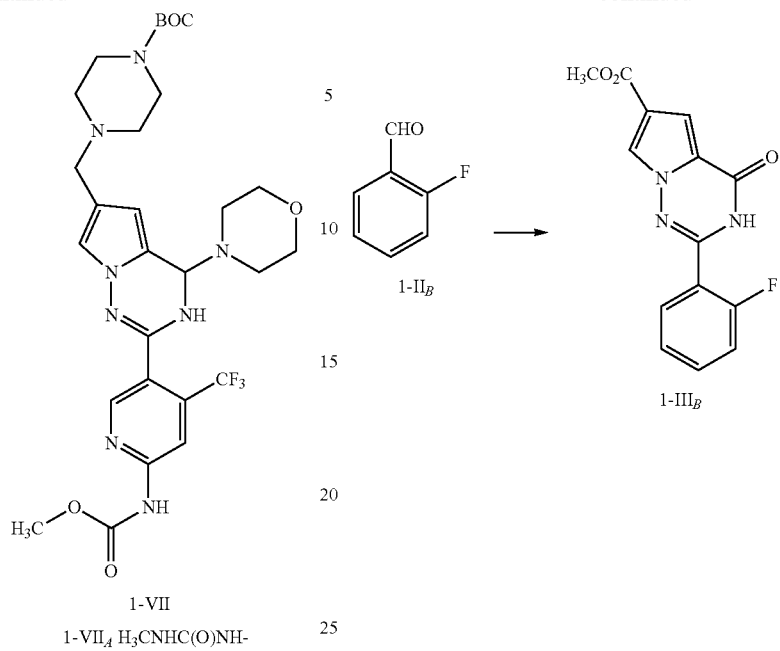

Additional starting compounds 1-III$_{A-C}$ (see compounds Compound 1-101 to Compound 1-172) can be prepared as shown in Scheme 3. These starting compounds can then be modified as described herein.

Scheme 3

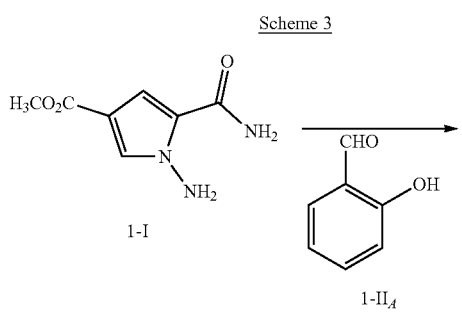

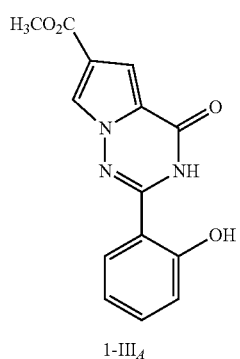

The X groups of the present disclosure (e.g., see compounds Compound 1-101 to Compound 1-172) can be attached as shown in Scheme 4. The BOC protecting group of compound 1-VII (or acetyl as noted above) can be removed via acid hydrolysis (e.g., HCl in methanol) to provide compound 1-VIII. The piperazinyl group of compound 1-VIII can then be reacted with an appropriate ester (e.g., for 1-IX and 1-IX$_A$, CH$_2$=CHC(O)(CH$_2$)$_2$C(O)OCH$_3$ or an acid or activated acid thereof can be used) in the presence of a base (e.g., K$_2$CO$_3$ or dimethylaminopyridine) to provide final compound 1-IX (Compound 1-101) or 1-IX$_A$ (Compound 1-105). If the X group contains a moiety that might react under the amide-forming conditions, a protected X' group (e.g., protected terminal amine) could be used, which would then be deprotected and modified to arrive at the final, desired compound (e.g., the terminal amine could be deprotected, then reacted with an appropriate ester or acid to form a final amide for X).

Scheme 4

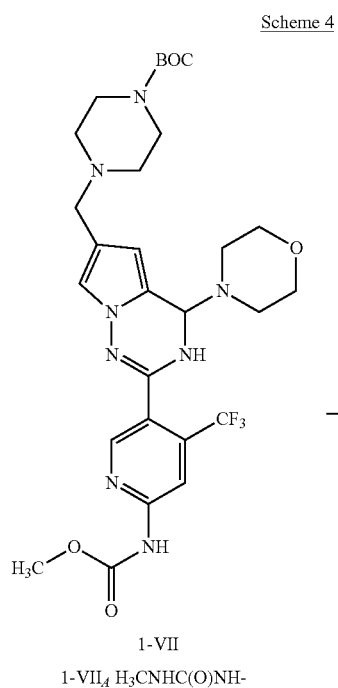

1-VII
1-VII$_A$ H$_3$CNHC(O)NH-

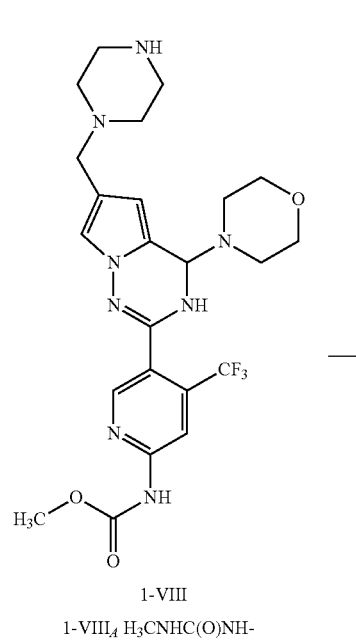

1-VIII
1-VIII$_A$ H$_3$CNHC(O)NH-

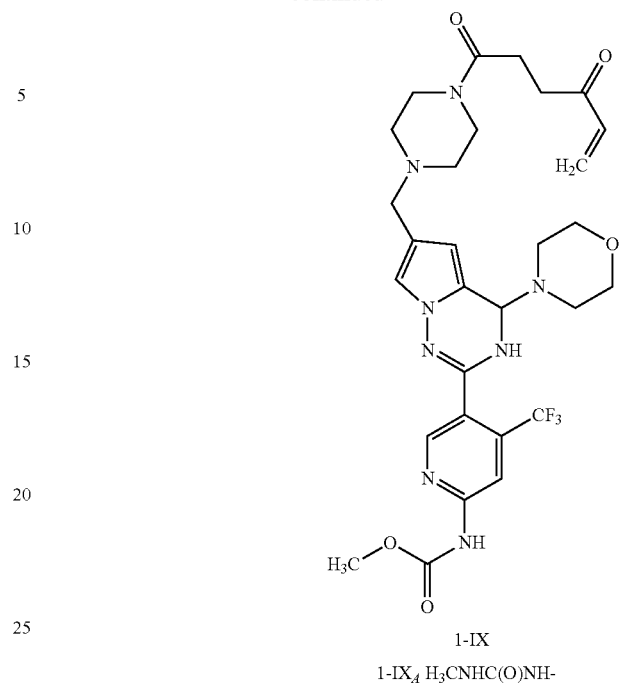

1-IX
1-IX$_A$ H$_3$CNHC(O)NH-

Example 3: Synthesis of Compound 1-102

Compounds 1-XXII and Compounds 1-XXV, intermediates to many of the compounds, Compound 1-101 to Compound 1-172, can be prepared as shown in Scheme 5. Precursor Compound 1-XXXII and Compound 1-102 can be synthesized as shown in Scheme 6. The remaining compounds can be synthesized with similar methods.

Scheme 5

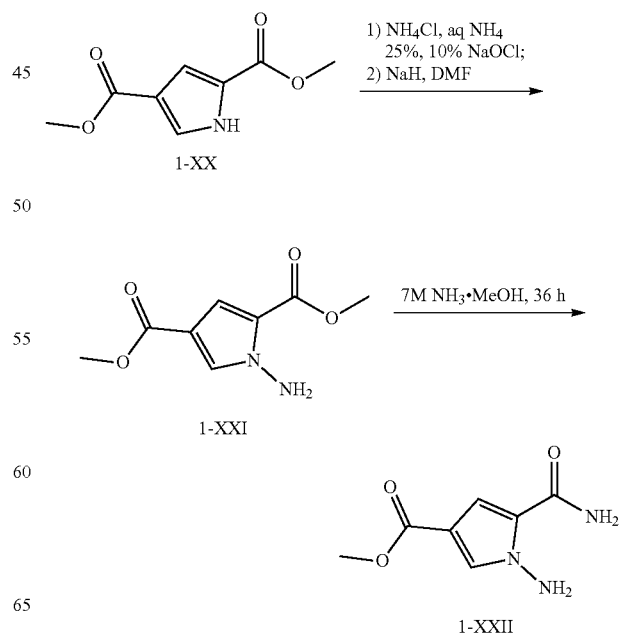

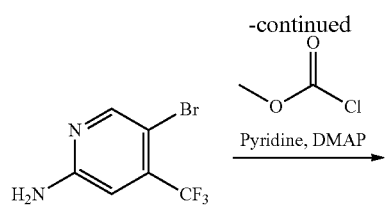
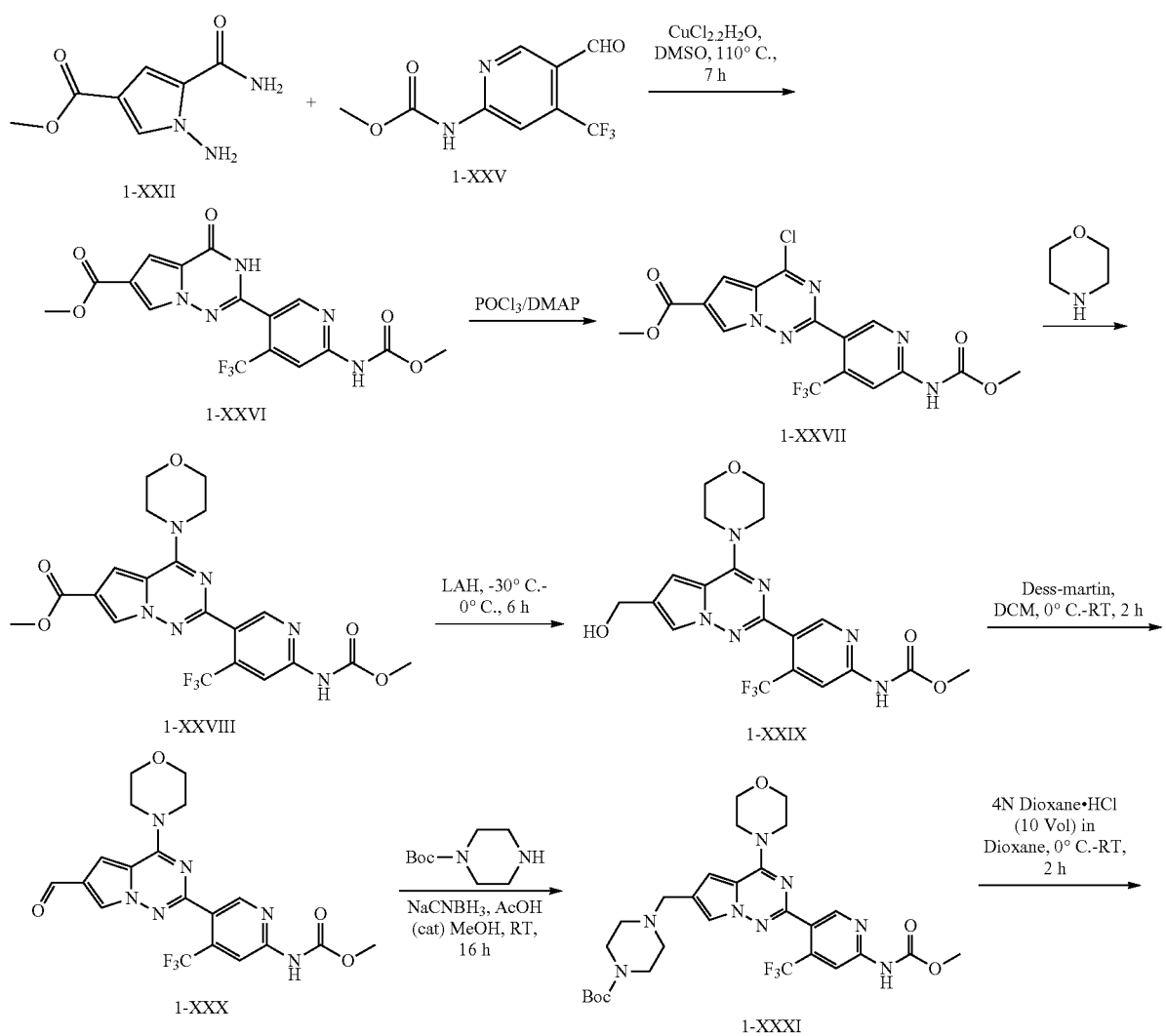
Scheme 6

-continued

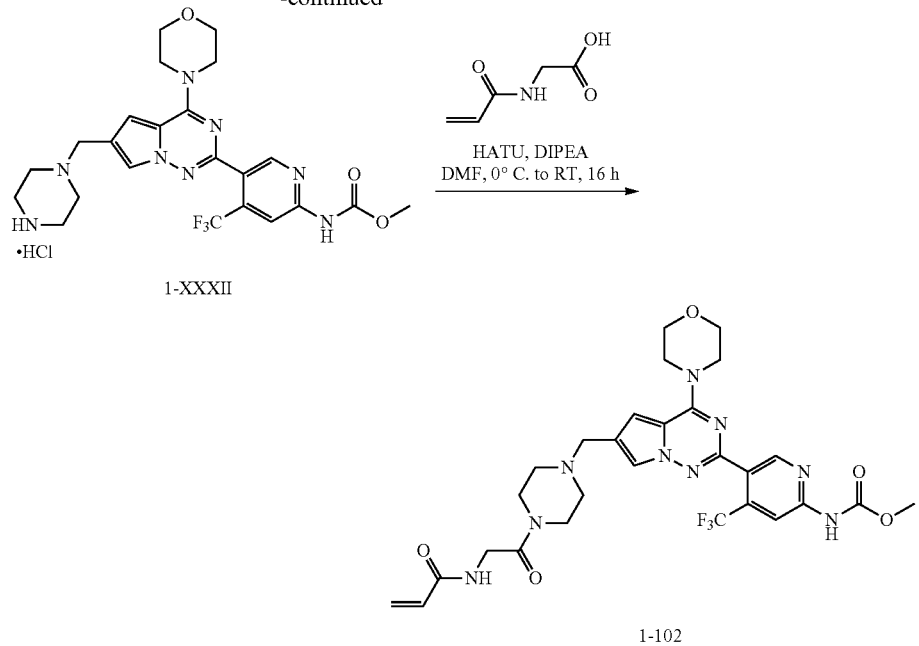

1-XXXII 1-102

Example 4: General Method for Screening of the ARCS

The ARCS of the present disclosure can be synthesized by one skilled in the art using general chemical synthetic principles and techniques. Alternatively, the ARCSs can be produced using known combinatorial methods to produce large libraries of ARCSSs. The ARCS of the present disclosure can also be synthesized as shown in Examples 1 to 3. The ARCS which binds to the biological target of the target cell covalently can then be screened by gel assay, western blot, ELISA, antibody array, or a NanoBRET assay.

Example 5: Transfection Protocol and Readout for NanoBRET Screening of ARCS

Human embryonic kidney 293-H (HEK 293, Gibco 293-H, #11631017) cell lines are maintained in Dulbecco's Modified Eagle Medium, high glucose, pyruvate (DMEM, Gibco, #11995065) supplemented with 10% fetal bovine serum (FBS, Gibco, #10082147) and 1× penicillin-streptomycin (100× solution, Gibco, #15140148) at 37° C. and 5% $CO_2$ in a water-saturated incubator. Cell are trypsinized using 0.05% or 0.25% Trypsin-EDTA solution (Trypsin-EDTA, phenol red, Gibco, #25200056 (0.25%) or #25300054). Opti-MEM media supplemented with 10% fetal bovine serum (Opti-MEM I reduced serum media, no phenol red, Gibco, #11058021) is used for culturing cells overnight for NanoBRET readout experiments.

HEK293 cells are cultivated appropriately prior to assay. The medium from cell flask is removed via aspiration, washed 1× with PBS followed by aspiration, trypsinized, and cells are allowed to dissociate from the flask. Trypsin is neutralized using growth medium and cells are pelleted via centrifugation at 200×g for 5 minutes. The medium is aspirated and the cells are resuspended into a single cell suspension using Opti-MEM I supplemented with 10% FBS. The cell density is adjusted to $2\times10^5$/mL in Opti-MEM I supplemented with 10% FBS in a sterile, conical tube. The cells are transfected and aliquoted directly in a 96-well plate for the NanoBRET assay the next day, and therefore, the cells are cultured overnight in Opti-MEM. The cells are also transfected in bulk and dispensed into a 96-well plate to allow cells to adhere to the plate overnight, thereby enabling washout studies.

The lipid:DNA complexes are prepared as follows:

A 10 µg/mL solution of DNA is prepared in Opti-MEM without serum. This solution contains the following ratios of carrier DNA and DNA encoding NanoLuc fused to the biological target. Serial dilution steps may be warranted to accurately dilute the NanoLuc fusion DNA. Added, in order, the following reagents to a sterile polystyrene test tube: 1 mL of Opti-MEM without phenol red; 9.0 µg/mL of carrier DNA; 1.0 µg/mL of NanoLuc fusion DNA (for some targets, the amount is less). The reagents are mixed thoroughly.

30 µL of FuGENE HD is added into each mL of DNA mixture to form lipid:DNA complex. Care is taken such that FuGENE HD does not touch the plastic side of the tube and pipetted directly into the liquid in the tube. It is mixed by pipetting up and down 5-10 times and incubated at room temperature for 20 minutes to allow complexes to form. 1 part (e.g. 1 mL) of lipid:DNA complex is mixed with 20 parts (e.g. 20 mL) of HEK293 cells in suspension at $2\times10^5$/mL and mixed gently by pipetting up and down 5 times in a sterile, conical tube. Larger or smaller bulk transfections are scaled accordingly, using this ratio. 100 µL cells+lipid:DNA complex is dispensed into a sterile, tissue-culture treated 96-well plate (20,000 cells/well), and incubated at least 16 hours to allow expression. The cells are incubated in a 37° C.+5% CO2 incubator for >16 hrs. A serially diluted inhibitor or test compound is prepared at 100× final concentration in 100% DMSO. The serially diluted inhibitor stock is prepared in PCR plates. 1 µL per well of 100× serially diluted inhibitor/test compound is added to the cells in 96-well plates that have been transiently transfected overnight and mixed by tapping the plate by hand. The plate is incubated at 37° C.+5% CO2 incubator overnight. A 1× solution of substrate mix (500× stock) and appropriate concentration of tracer is prepared in Opti-Mem. The cells are washed by setting a plate washer to the 96 well plate 5× in PBS pH 7.4 by adding 200 μL PBS each time. The cells are incubated at 37° C. for 2 hours. 100 μL of the 1× Substrate-Tracer solution is added and the 96 well plate is gently tapped to mix. The plate on plate reader is read every hour for the next 6 hours. The binding assays of some ARCS are shown below. Compound 1-XXXII formed a covalent bond with PI3-kinase from about 5% to 20%. ARCS selected from the group consisting of Compounds 1-101, 1-102, 1-113, 1-114, 1-119, 1-120, 1-125 and 1-126 formed a covalent bond with PI3-kinase from about 80% to 100%. Compounds 1-171 and 1-172 formed a covalent bond with PI3-kinase from about 50% to 80%. The activity of PI3-kinase is inhibited by Compound 1-XXXII from about 5% to 20%. The activity of PI3-kinase is inhibited by ARCS selected from the group consisting of Compounds 1-101, 1-102, 1-113, 1-114, 1-119, 1-120, 1-125 and 1-126 from about 80% to 100%. The activity of PI3-kinase is inhibited by Compounds 1-171 and 1-172 from about 50% to 80%.

|  | Binding |
|---|---|
| 1-XXXII | + |
| 1-101 | +++ |
| 1-102 | +++ |
| 1-113 | +++ |
| 1-114 | +++ |
| 1-119 | +++ |
| 1-120 | +++ |
| 1-125 | +++ |
| 1-126 | +++ |
| 1-171 | ++ |
| 1-172 | ++ |

| Percent inhibition | | |
|---|---|---|
| + | ++ | +++ |
| <20% | 50-80% | >80% |

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

The invention claimed is:

1. A method for treating cancer in a subject in need thereof, comprising administering to the subject in need thereof an effective amount of a compound of Formula 1-50:

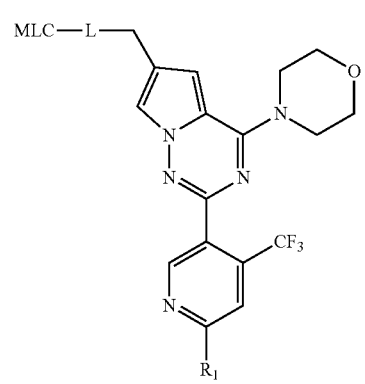

Formula 1-50 or a pharmaceutically acceptable salt thereof,
wherein:
L is selected from the group consisting of:

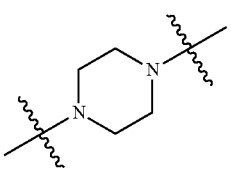

and

-continued
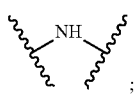;
R$_1$ is selected from the group consisting of:
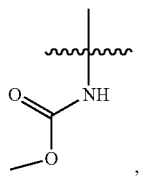,
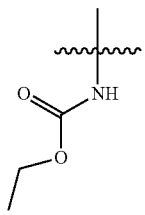,
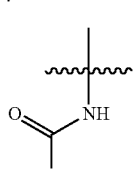 and
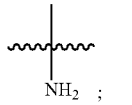;
and
CLM is selected from the group consisting of:
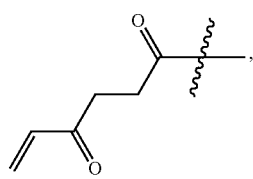, 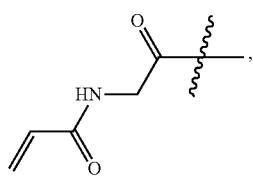,
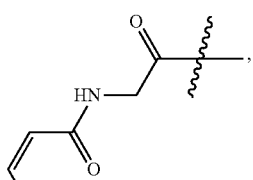,
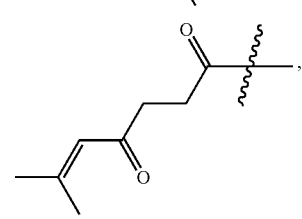,
-continued
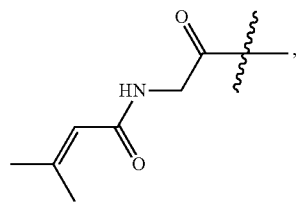
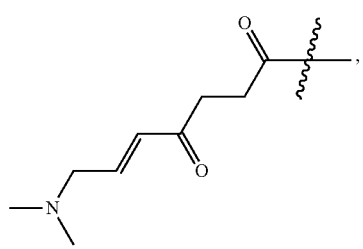
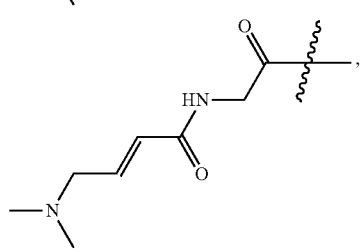
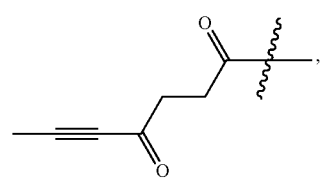
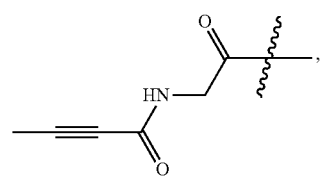
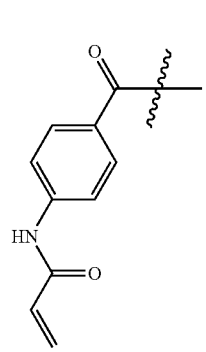
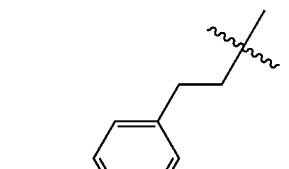 and 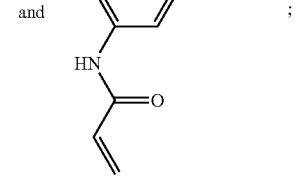;
and
wherein the cancer is leukemia, lung cancer, ovarian cancer, prostate cancer, breast cancer, or colon cancer.

2. The method of claim 1, wherein L is
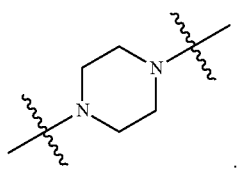
3. The method of claim 2, wherein $R_1$ is:
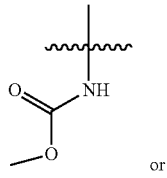
or
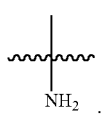
4. The method of claim 3, wherein CLM is selected from the group consisting of:
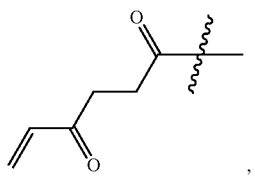
,
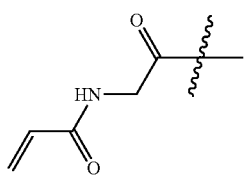
,
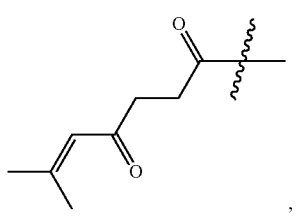
,
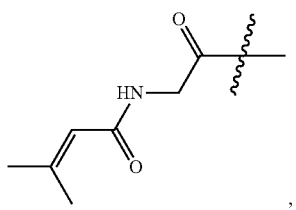
,
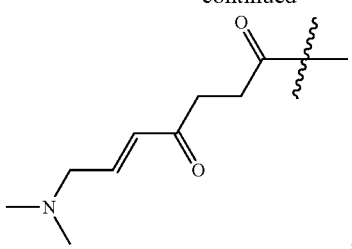
,
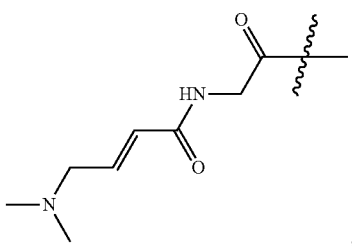
,
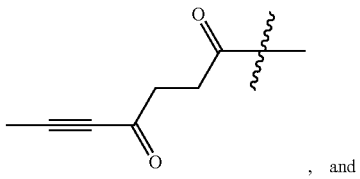
, and
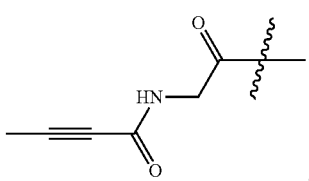
.
5. The method of claim 1, wherein the compound is selected from the group consisting of:
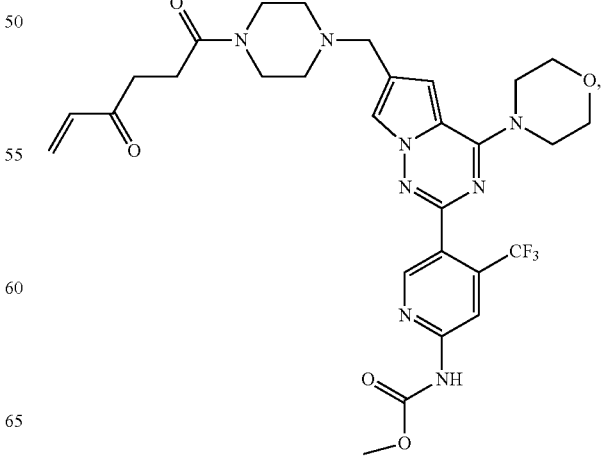

151
-continued
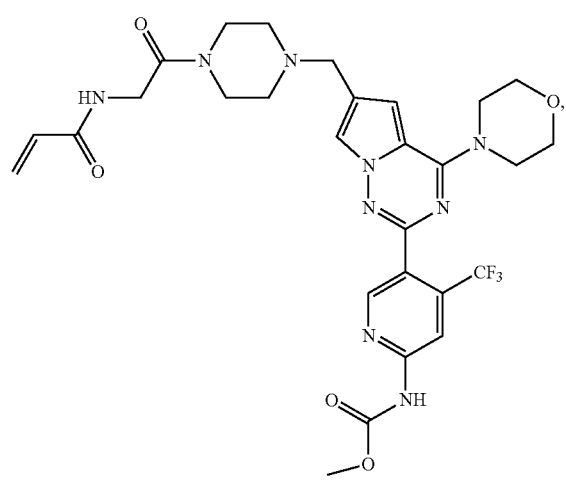
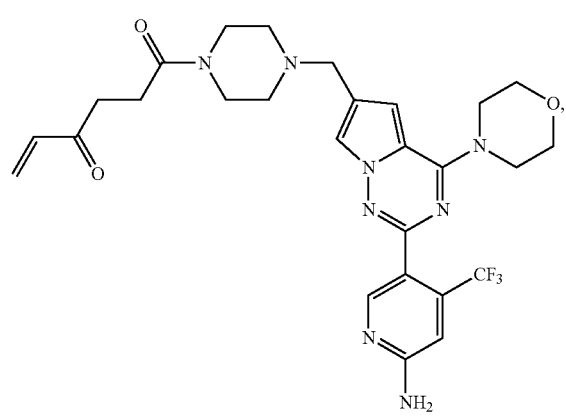
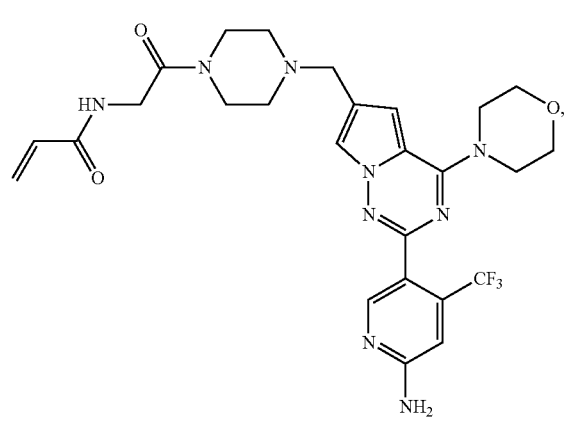
152
-continued
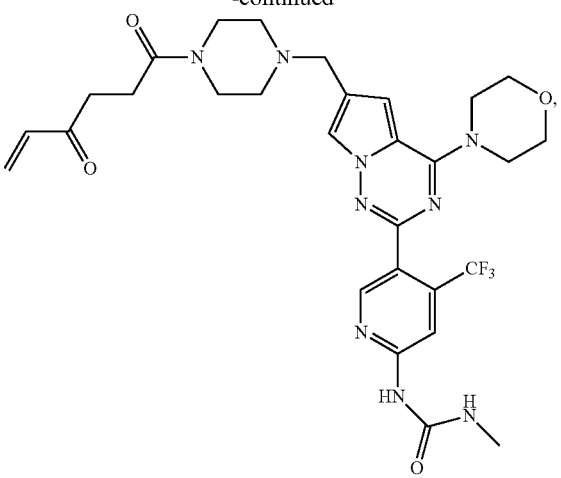
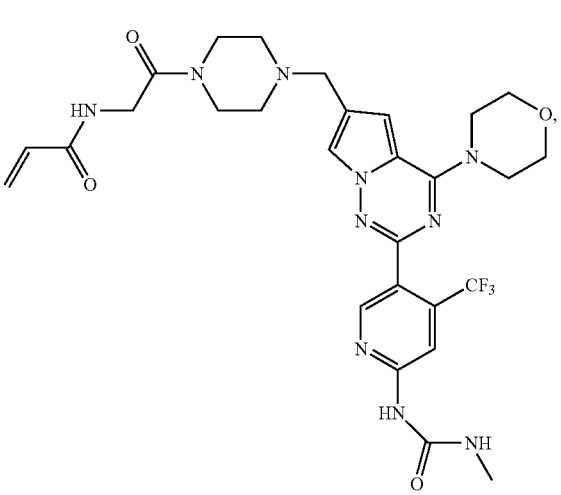
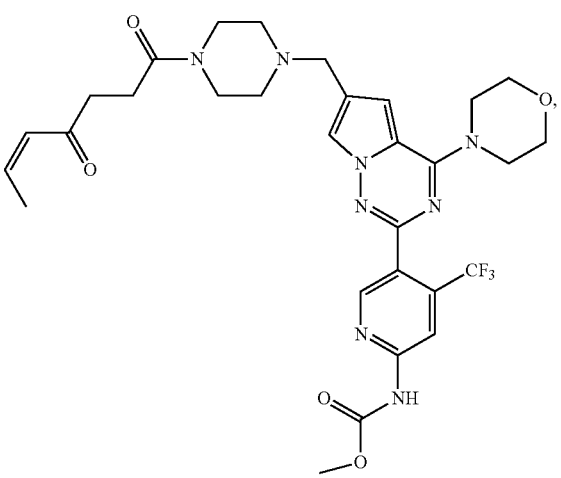

153
-continued
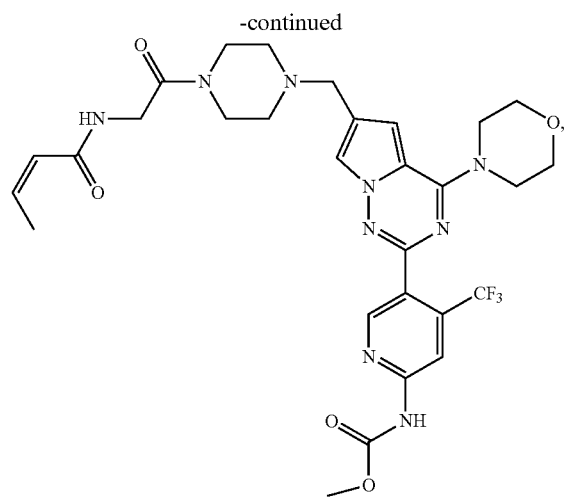
154
-continued
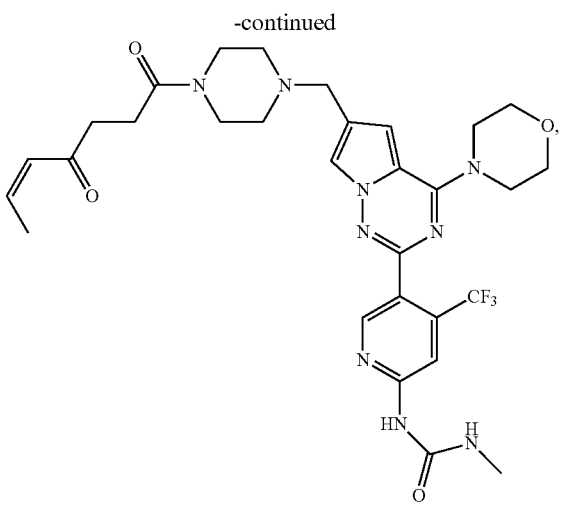
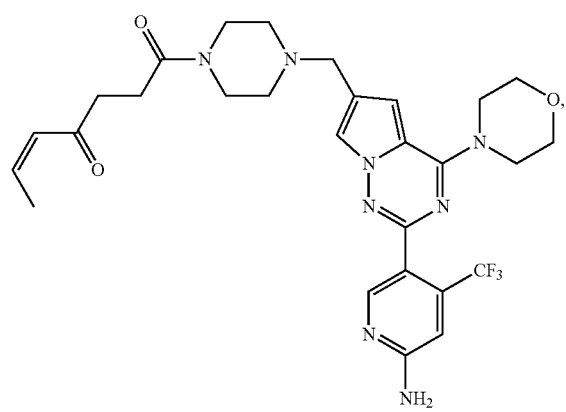
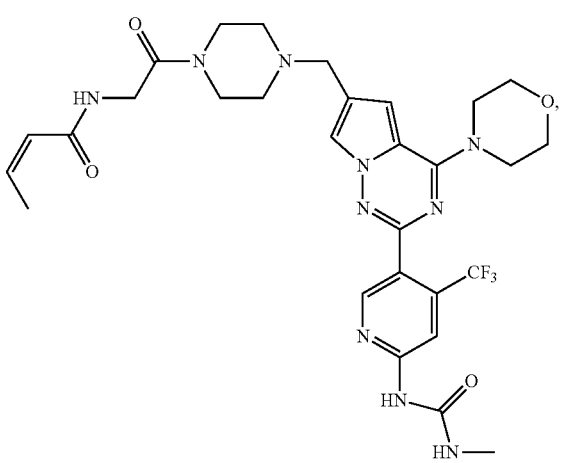
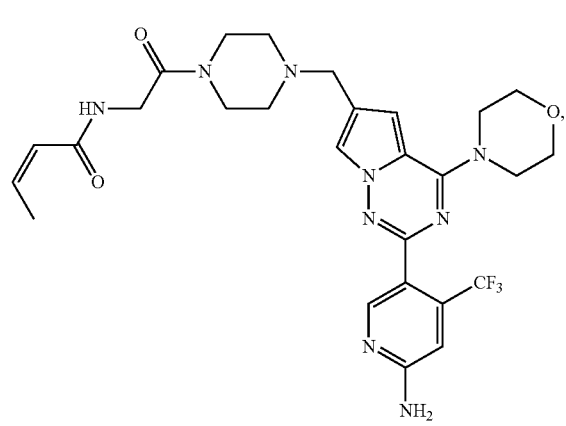
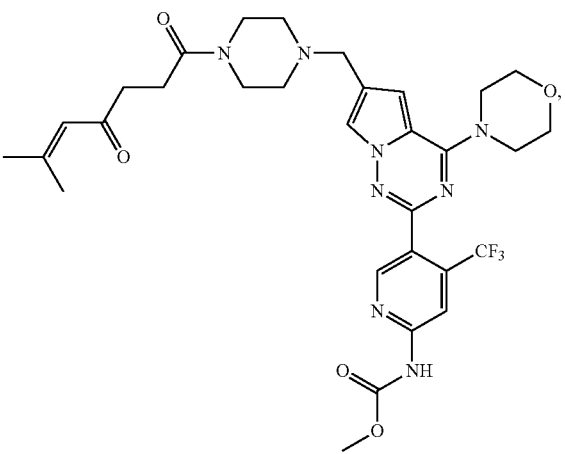

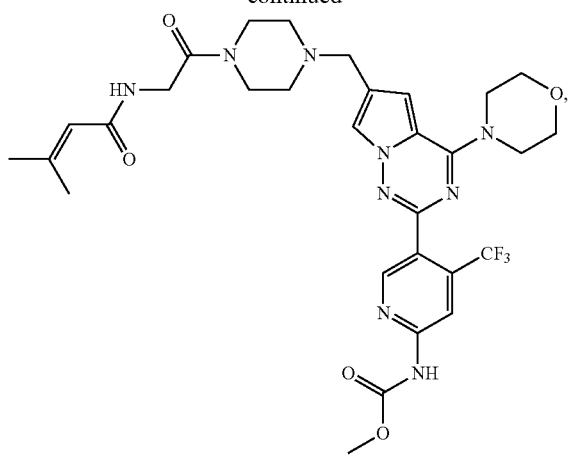
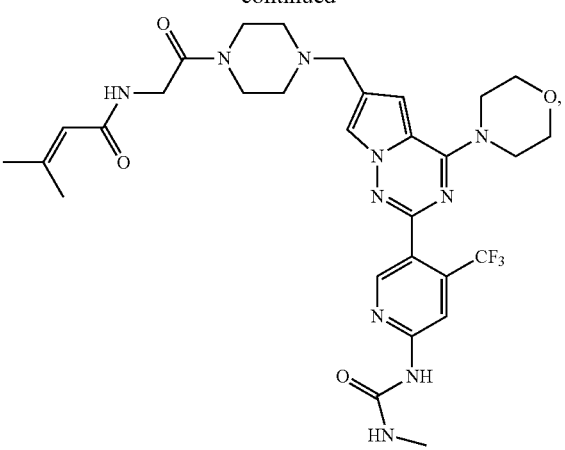

157
-continued
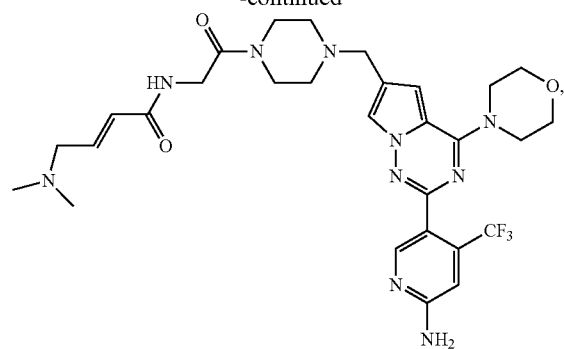
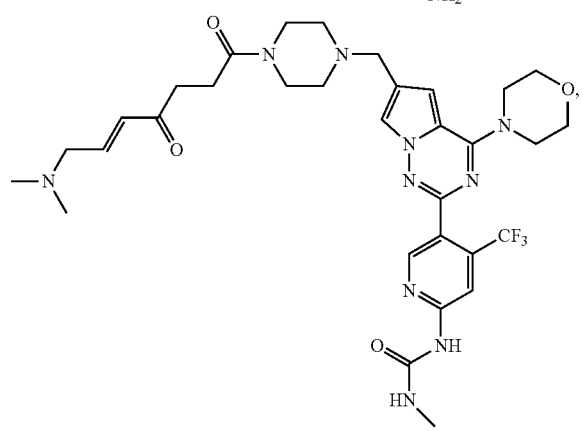
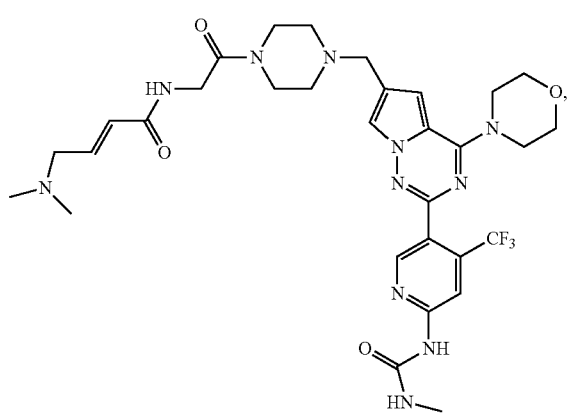
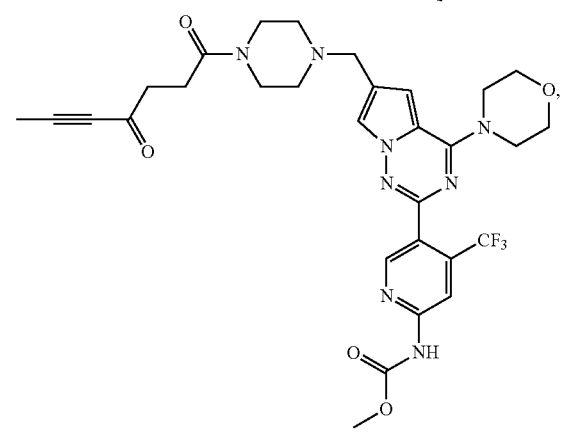
158
-continued
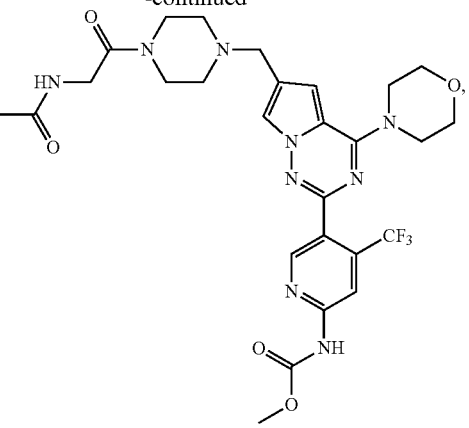
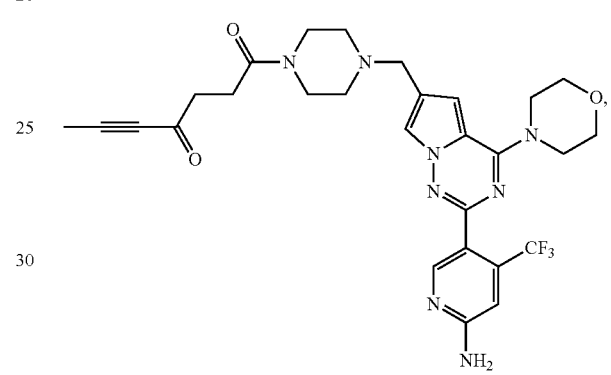
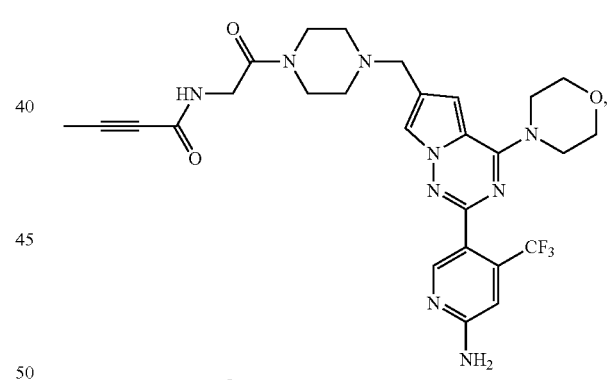
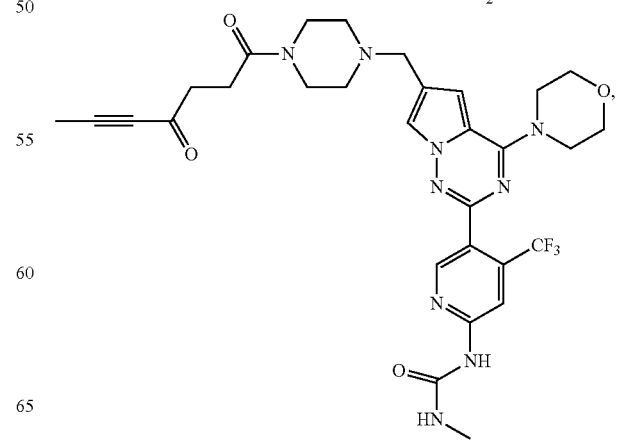

159
-continued
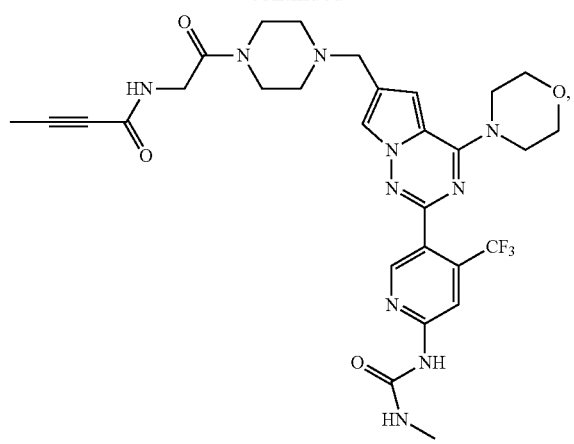
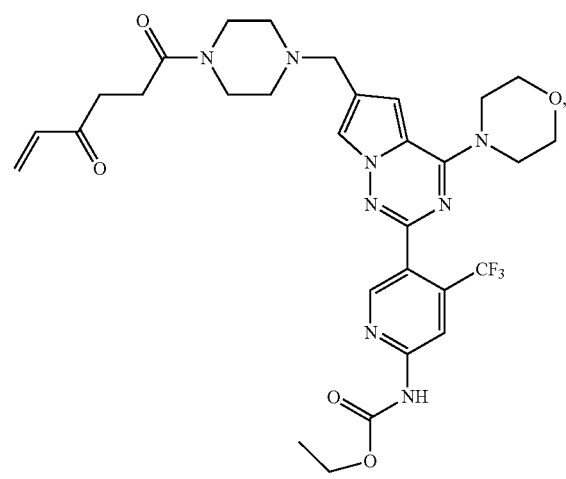
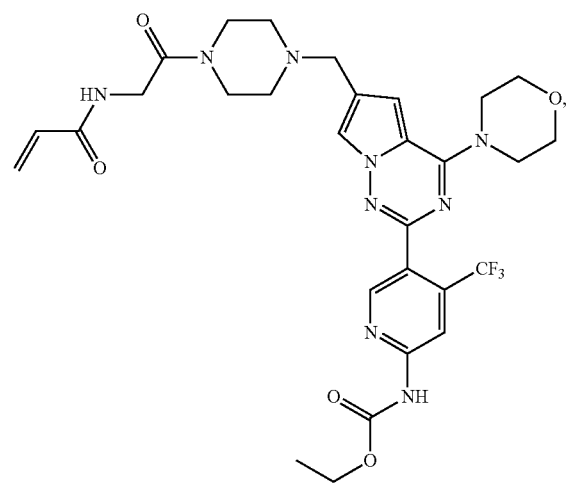
160
-continued
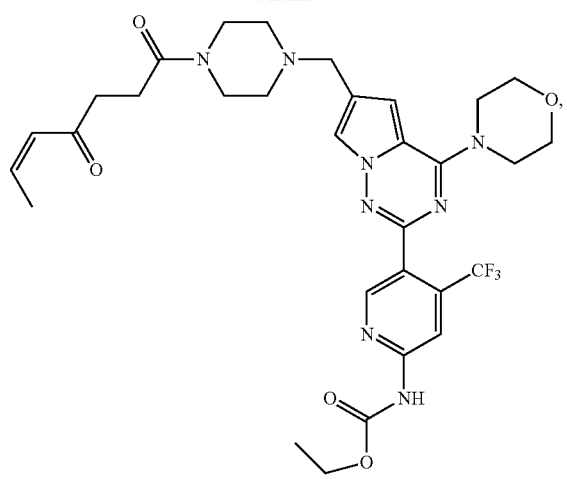
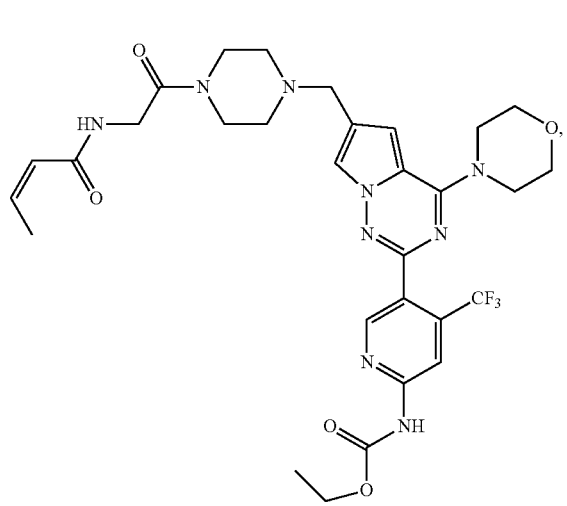

161
-continued
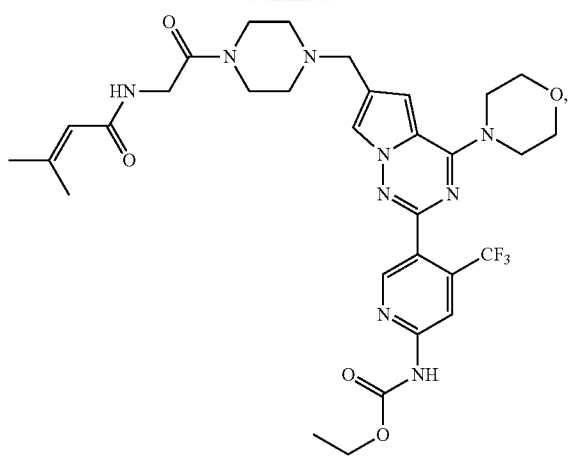
162
-continued
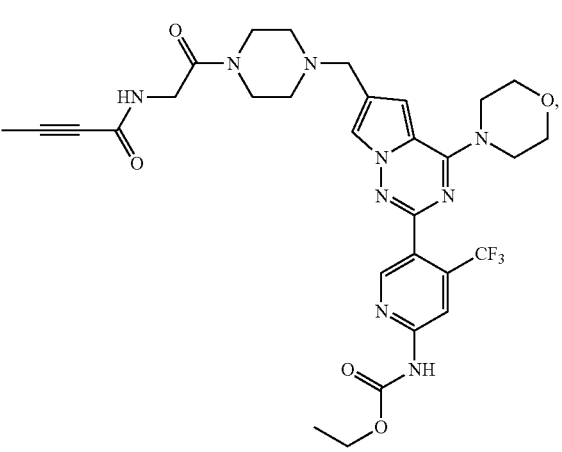
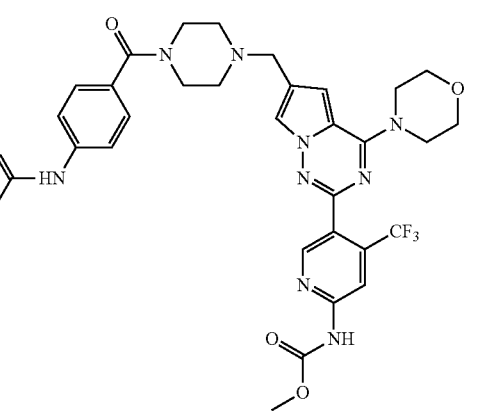
and
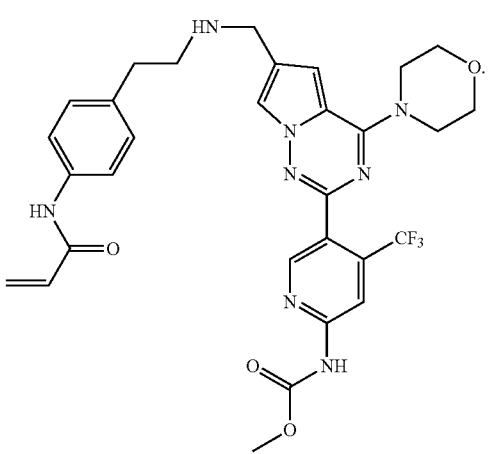 [SMILES: C=CC(=O)Nc1ccc(CCNCc2cc3c(N4CCOCC4)nc(-c4cnc(NC(=O)OC)cc4C(F)(F)F)nn3c2)cc1]

6. The method of claim 5 selected from the group consisting of:
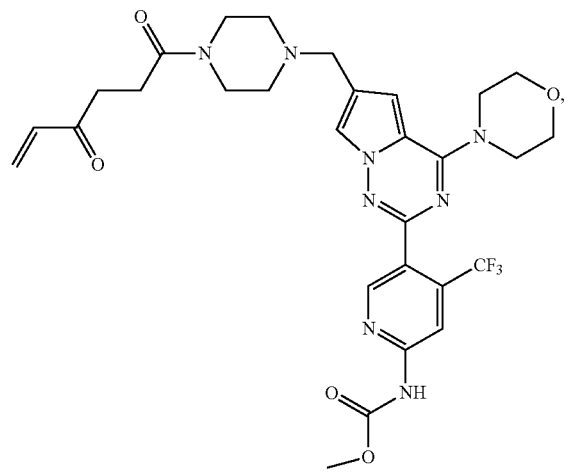
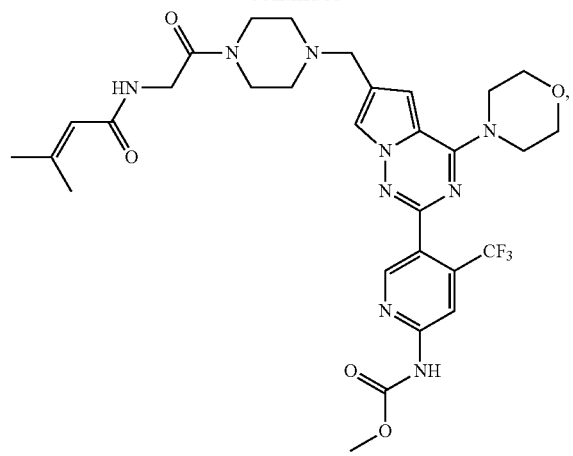
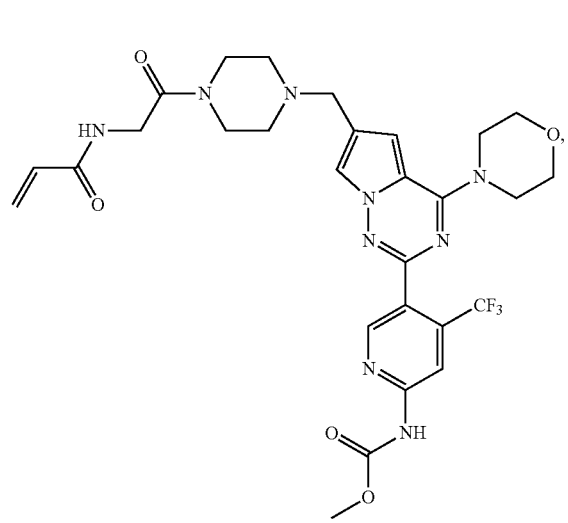
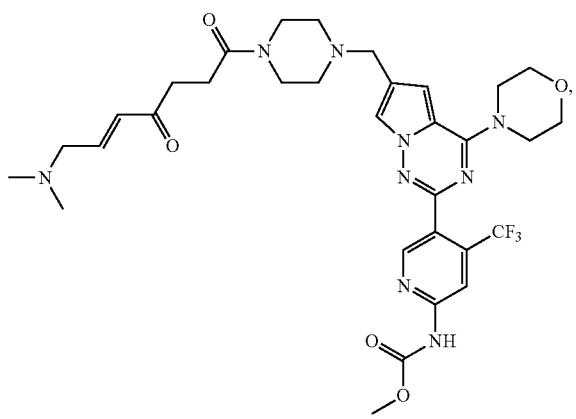
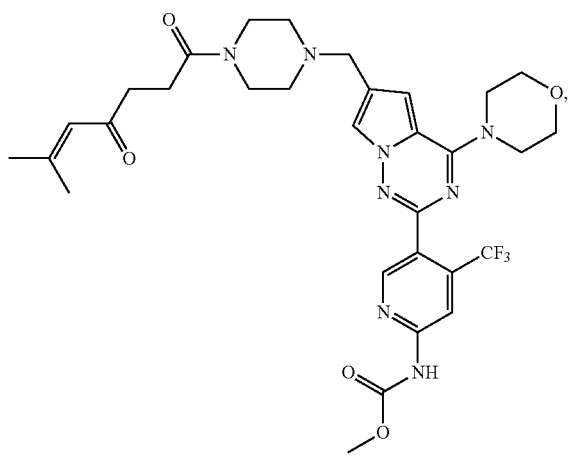
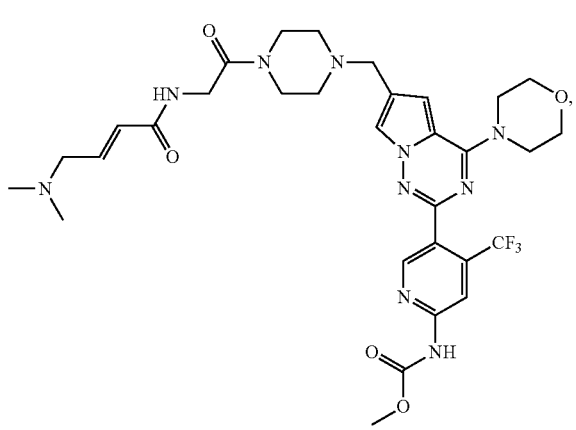

165
-continued
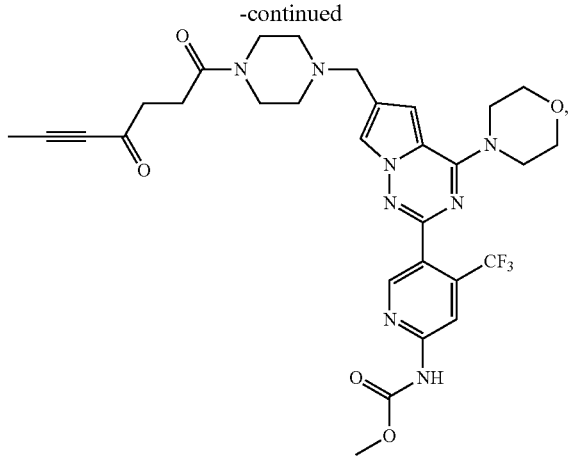
166
-continued
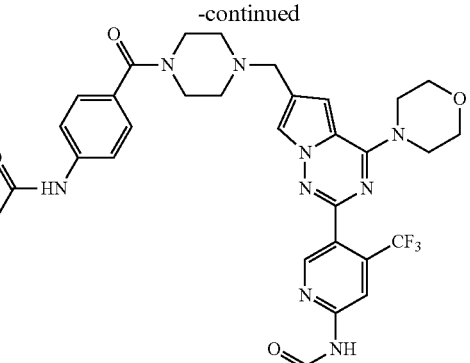
and
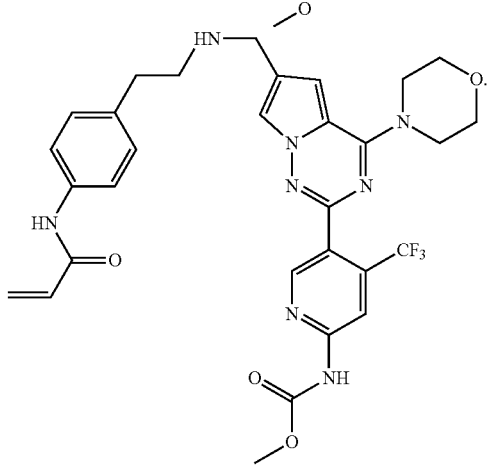
7. The method of claim 1, wherein the cancer is characterized by a mutation in the PIK3CA gene.
8. The method of claim 5, wherein the cancer is characterized by a mutation in the PIK3CA gene.
* * * * *